US006696259B1

(12) United States Patent
Ibanez et al.

(10) Patent No.: US 6,696,259 B1
(45) Date of Patent: Feb. 24, 2004

(54) ASSAYS USING GLIAL CELL LINE-DERIVED NEUROTROPHIC FACTOR RECEPTORS

(75) Inventors: Carlos F. Ibanez, Stockholm (SE); Miles Trupp, Greenbrae, CA (US); Mart Saarma, Helsinki (FI); Hannu Sariola, Helsinki (FI); Urmas Arumäe, Espoo (FI); Petro Suvanto, Vantaa (FI)

(73) Assignee: Licentia Ltd., Helsinki (FI)

( * ) Notice: Subject to any disclaimer, the term of this patent is extended or adjusted under 35 U.S.C. 154(b) by 0 days.

(21) Appl. No.: 08/861,990

(22) Filed: May 22, 1997

Related U.S. Application Data

(63) Continuation-in-part of application No. 08/747,842, filed on Nov. 13, 1996, now abandoned.
(60) Provisional application No. 60/006,619, filed on Nov. 13, 1995, provisional application No. 60/015,767, filed on Apr. 16, 1996, provisional application No. 60/021,965, filed on Jun. 27, 1996, provisional application No. 60/020,638, filed on Jun. 27, 1996, and provisional application No. 60/020,639, filed on Jun. 27, 1996.

(51) Int. Cl.[7] .............................................. G01N 33/68

(52) U.S. Cl. ............................ 435/7.21; 435/15; 435/6

(58) Field of Search .............................. 435/7.21, 15, 6

(56) References Cited

FOREIGN PATENT DOCUMENTS

| WO | WO 97/44356 | 11/1997 |
|---|---|---|
| WO | WO 98/36072 | 8/1998 |
| WO | WO 98/46622 | 10/1998 |
| WO | WO 98/53069 | 11/1998 |
| WO | WO 98/54213 | 12/1998 |

OTHER PUBLICATIONS

Rudinger, In "Peptide Hormones" (ed. J.A. Parsons) University Park Press, Baltimore, pp. 1–7, 1976.*
Durbec, et al., GDNF signalling through the Ret receptor tyrosine kinase, Nature, 1996, 381, 789–792.
Pichel, et al., "Defects in enteric innervation and kidney development in mice lacking GDNF", Nature, 1996, 382, 73–76.
Trupp, et al., "Functional receptor for GDNF encoded by the c–ret proto–oncogene", Nature, 1996, 381, 785–789.
Ibanez, C.F. "Biochemical characterisation of GDNF receptors and downstream responses", International Journal of Developmental Neuroscience, 1996, 14(1), 76, XP–001041850.
Trupp, M. et al., "Characterization of GDNF receptors on primary neurons and cell lines", Society for Neuroscience Abstracts, 1995, 21(1–3), 1302, XP–001041846.
Baloh, R.H. et al., "TRNR2, a novel receptor that mediates neurturin and GDNF signaling through ret", Neuron, 1997, 18, 793–802, XP 002065821.

Jing, S. et al., "GFRALPHA–2 and GFRALPHA–3 are two new receptors for ligands of the GDNF family", Journal of Bilogical Chemistry, 1997, 272(52), 33111–33117, XP 002065824.
Sanicola, M. et al., "Glial cell line–derived neurotrophic factor–dependent ret activiation can be mediated by two different cell–surface accessory proteins", Proceedings of the National Academy of Sciences of USA, 1997, 94(12), 6238–6243, XP002059966.
Suvanto, P. et al., "Cloning, mRNA distribution and chromosomal localisation of the gene for glial cell line derived neurotrophic factor receptor beta, a homologue to GDNFR–alpha", Human Molecular Genetics, 1997, 6(8), 1267–1273, XP 002196287.
Trupp, M., et al., "Multiple GPI–anchored receptors control GDNF–dependent and independent activation of the c–Ret receptor tyrosine kinase," Molecular and Cellular Neuroscience, 1998, 11, 47–63.
Sainio, et al., "Glial–cell–line–derived neurotrophic factor is required for bud initiation from ureteric epithelium", Development, 1997, 124, 4077–4087.
Acheson, et al., "A BDNF autocrine loop in adult sensory neurons prevents cell death", Nature, 1995, 374, 450–453.
Arenas, E. And Persson, H., "Neurotrophin–3 prevents the death of adult central noradrenergic neurons in vivo", Nature, 1994, 367, 368–371.
Arenas, et al., "GDNF Prevents Degeneration and Promotes the Phenotype of Brain Noradrenergic Neurons In Vivo", Neuron, 1995, 15, 1465–1473.
Asai, et al., "Mechanism of Activation of the ret Proto–oncogene by Multiple Endocrine Neoplasia 2A Mutations", Mol. & Cell. Biol., 1995, 15, 1613–1619.
Attisano, et al., "TGF–β receptors and actions", Biochimica et Biophysica Acta, 1994, 1222, 71–80.
Attisano, et al., "Identification of Human Activin and TGFβ Type 1 Receptors That Form Heteromeric Kinase Complexes with Type II Receptors", Cell, 1993, 75, 671–680.
Avantaggiato, et al., "Developmental Expression of the RET Protooncogene[1]", Cell Growth Differ., 1994, 5, 305–311.
Beck, et al., "Mesencephalic dopaminergic neurons protected by GDNF from axotomy–induced degeneration in the adult brain", Nature, 1995, 373, 339–341.
Borrello, et al., "The oncogenic versions of the Ret and Trk tyrosine kinases bind Shc and Grb2 adaptor proteins", Oncogene, 1994, 9, 1661–1668.

(List continued on next page.)

Primary Examiner—Gary Kunz
Assistant Examiner—Robert C. Hayes
(74) Attorney, Agent, or Firm—Woodcock Washburn LLP

(57) ABSTRACT

Receptors for Glial Cell Line-Derived Neurotrophic Factor (GDNF), their cellular expression, isolation, biochemical characterization, and sequences are disclosed. c-RET is disclosed as one receptor for GDNF; additional novel receptors are also disclosed. The preparation of monoclonal antibodies directed against GDNF is also disclosed.

2 Claims, 38 Drawing Sheets

OTHER PUBLICATIONS

Boulton, et al., "ERKs: A Family of Protein–Serine/Threonine Kinases That are Activated and Tyrosine Phosphorylated in Response to Insulin and NGF", *Cell*, 1991, 65, 663–675.

Brewer, G.J. and Cotman, C.W., "Survival and growth of hippocompal neurons in defined medium at low density: advantages of a sandwich culture technique or low oxygen", *Brain Research*, 1989, 494, 65–74.

Buj–Bello, et al., "GDNF is an Age–Specific Survival Factor for Sensory and Autonomic Neurons", *Neuron*, 1995, 15, 821–828.

Capecchi, M., "The New Mouse Genetics: Altering the Genome by Gene Targeting", *Trends Genet.*, 1989, 5, 70–76.

Chen, et al., "A WD–domain protein that is associates with and phosphorylated by the type II TGF–$\beta$ receptor", *Nature*, 1995, 377, 548–552.

Cowell, J.K., "A photographic representation of the variability in the G–banded structure of the chromosomes in the mouse karyotype, A guide to the identification of the individual chromosomes", *Chromosoma*, 1984, 89, 294–320.

Curran, et al., "Isolation and characterization of the c–fox(rat) cDNA and analysis of post–translational modification in vitro", *Oncogene*, 1987, 2, 79–84.

David, et al., "Requirement for MAP Kinase (ERK2) Activity in Interferon $\alpha$–and Interferon $\beta$–Stimulated Gene Expression Through STAT Proteins", *Science*, 1995, 269, 1721–1723.

Derynck, R., "TGF–$\beta$–receptor–mediated signaling", 1994, *TIBS*, 19, 548–553.

Dijke, et al., "Characterization of Type 1 Receptors for Transforming Growth Factor–$\beta$ and Activin", *Science*, 1994, 264, 101–104.

Dow, et al., "Second Locus for Hirschsprung Disease/Waardenburg Syndrome in a Large Mennonite Kindred", *Am. J. Med. Genet.*, 1994, 53, 75–80.

Durbec, et al., "Common origin and developmental dependence on c–ret of subsets of enteric and sympathetic neuroblasts", *Development*, 1996, 122, 349–358.

Eaton, et al., "Developmental Regulation of Early Serotonergic Neuronal Differentiation: The Role of Brain–Derived Neurotrophic Factor and Membrane Depolarization", *Dev. Biol.*, 1995, 170, 169–182.

Edery, et al., "Mutations of the RET proto–oncogene in Hirschsprung's disease", *Nature*, 1994, 367, 378–380.

Ernfors, P. And Persson, H., "Developmentally Regulated Expression of HDNF/NT–3 nRNA in Rat Spinal Cord Motoneurons and Expression of BDNF mRNA in Embryonic Dorsal Root Ganglion", 1991, *Eur. J. Neurosci.*, 3, 953–961.

Gash, et al., "Functional recovery in parkinsonian monkeys treated with GDNF", *Nature*, 1996, 380, 252–255.

Gille, et al., "Phosphorylation of transcription factor p62 $^{TCF}$ by MAP kinase stimulates ternary complex formation at c–fox promoter", *Nature*, 1992, 358, 414–417.

Gizang–Ginsberg, E. And Ziff, E., "Nerve growth factor regulates tyrosine hydroxylase gene transcription through a nucleoprotein complex that contains c–Fos", *Genes & Dev.*, 1990, 4, 477–491, Gong, et al., "GDNF and BDNF Protect a Catecholaminergic Cell Line (CATH.a) from Dopamine Induced Cell Death", *21 Abs. Soc. Neurosci.*, 1995, 1789.

Hammond, et al., "Neuronal Properties of Clonal Hybrid Cell Lines Derived from Central Cholinergic Neurons", *Science*, 1986, 234, 1237–1240.

Hartsough, M.T. and Mulder, K.M., "Transforming Growth Factor $\beta$ Activation of p44$^{mapk}$ in Proliferating Cultures of Epithelial Cells", *J. Biol. Chem.*, 1995, 270, 7117–7124.

von Heijne, G., "A new method for predicting signal sequence cleavage sites", *Nucleic Acids Res.*, 1986, 14, 4683–4690.

Heiskanen, et al., "Fiber–FISH: experiences and a refined protocol", *Genet. Anal. Biomol. Eng.*, 1996, 12, 179–184.

Henderson, et al., "GDNF: A Potent Survival Factor for Motoneurons Present in Peripheral Nerve and Muscle", *Science*, 1994, 266, 1062–1064.

Hengerer, et al., "Lesion–induced increase in nerve growth factor mRNA is mediated by c–fos", *Proc. Natl. Acad. Sci. USA*, 1990, 87, 3899–3903.

Hofstra, et al., "A mutation in the RET protooncogenes associated with multiple endocrine neoplasia type 2B and sporadic medullary thyroid carcinoma", *Nature*, 1994, 367, 375–376.

Huang, X., "On global sequence alignment", *Comp. Appl. BioSci.*, 1994, 10, 227–235.

Ikeda, et al., "Specific expression of the ret proto–oncogene in human neuroblastoma cell lines", *Oncogene*, 1990, 5, 1291–1296.

Ip, et al., "Similarities and Differences in the Way Neurotrophins Interact with the Trk Receptors in Neuronal and Nonneuronal Cells", *Neuron*, 1993, 10, 137–149.

Jalava, A., & Mai, S., "Fos and Jun form cell specific protein complexes at the neuropeptide tyrosine promoter", *Oncogene*, 1994, 9, 2369–2375.

Jing, et al., "GDNF–Induced Activation of the Ret Protein Tyrosine Kinase Is Mediated by GDNFR–$\alpha$, a Novel Receptor for GDNF", *Cell*, 1996, 85, 1113–1124.

Kinglsey, D.M., "The TGF–$\beta$ superfamily: new members, new receptors, and new genetic tests of function in different organisms", *Genes & Dev.*, 1994, 8, 133–146.

Kotzbauer, et al., "Neurturin, a relative of glial–cell–derived neurotrophic factor", *Nature*, 1996, 384, 467–470.

Le Douarin, N.M. and Teillet, M.A., "The migration of neural crest cells to the wall of the digestive tract in avian embryo", *J. Embryol. Exp. Morph.*, 1973, 30, 31–48.

Letsou, et al., "Drosophila Dpp Signaling Is Mediated by the punt Gene Product: A Dual Ligand–Binding Type II Receptor of the TGF$\beta$ Receptor Family", *Cell*, 1995, 80, 899–908.

Lemieux, N., et al., "A simple method for simultaneous R–or G–banding and fluorescence in situ hybridization of small single–copy genes", *Cytogenet. Cell. Genet.*, 1992, 59, 311–312.

Li, et al., "Rescue of adult mouse motoneurons from injury–induced cell death by glial cell line–derived neurotrophic factor", *Proc. Natl. Acad. Sci. USA*, 1995, 92, 9771–9775.

Lichter, et al., "Rapid detection of human chromosome 21 aberrations by in situ hybridization", *Proc. Natl. Acad. Sci. USA*, 1988, 85, 9664–9668.

Lin, et al., "GDNF: A Glial Cell Line–Derived Neurotrophic Factor for Midbrain Dopaminergic Neurons", *Science*, 1993, 260, 1130–1132.

Lo, L. And Anderson, D.J., "Postmigratory Neural Crest Cells Expressing c–RET Display Restricted Developmental and Proliferative Capacities", *Neuron*, 1995, 15, 527–539.

Lopez–Casillas, et al., "Structure and Expression of the Membrane Proteoglycan Betaglycan, a Component of the TGF–β Receptor System", *Cell*, 1991, 67, 785–795.

Lorenzo, et al., "Mulitple mRNA isoforms of the human RET proto–oncogene generated by alternate splicing", *Oncogene*, 1995, 10, 1377–1383.

Machwate, et al., "c–fos Protooncogene Is Involved in the Mitogenic Effect of Transforming Growth Factor–β in Osteoblastic Cells", *Mol. Endocrin.*, 1995, 9, 187–198.

MacKay, K. And Danielpouri, D., "Novel 150–and 180–kDa Glycoproteins That Bind Transforming Growth Factor (TGF) –β2 Are Present in Several Cell Lines", *J. Biol. Chem.*, 1991, 266, 9907–9911.

Mak, Y.F. and Ponder, B.A.J., "RET oncogene", *Curr. Opin. Genet. Dev.*, 1996, 6, 82–86.

Massague, J., "Receptors for the TGF–β Family", *Cell*, 1992, 69, 1067–1070.

Milbrandt, J., "Nerve growth factor rapidly induces c–fos mRNA in PC12 rat pheochromocytoma cells", *Proc. Natl. Acad. Sci. USA*, 1986, 83, 4789–4793.

Mount, et al., "Glial cell line–derived neurotrophic factor promotes the survival and morphologic differentiation of Purkinje cells", *Proc. Natl. Acad. Sci. USA*, 1995, 92, 9092–9096.

Mulligan, et al., "Germ–line mutations of the RET proto–oncogene in multiple endocrine neoplasia type 2A", *Nature*, 1993, 363, 458–460.

Myers, et al., "Characterization of RET proto–oncogene 3' splicing variants and polyadenylation sites: a novel C–terminus for RET", *Oncogene*, 1995, 11, 2039–2045.

Neveu, I. And Arenas, E., "Neurotrophins Promote the Survival and Development of Neurons in the Cerebellum of Hypothyroid Rats In Vivo", *J. Cell Biol.*, 1996, 133, 631–646.

Oppenheim, et al., "Developing motor neurons rescued from programmed and axotomy–induced cell death by GDNF", *Nature*, 1995, 373, 344–346.

Pachnis, et al., "Expression of the c–ret proto–oncogene during mouse embryogenesis", *Development*, 1993, 119, 1005–1017.

Partanen, A.M. and Thesleff, I., "Localization and Quantitation of $^{125}$I–Epidermal Growth Factor Binding in Mouse Embryonic Tooth and Other Emryonic Tissues at Different Developmental Stages", *Developmental Biol.*, 1987, 120, 186–197.

Pinkel, et al., "Cytogenetic analysis using quantitative, high–sensitivity, fluorescence hybridization", *Proc. Natl. Acad. Sci. USA*, 1986, 83, 2934–2938.

Poulsen, et al., "TGFβ2 and TGFβ3 Are Potent Survival Factors for Midbrain Dopaminergic Neurons", *Neuron*, 1994, 13, 1245–1252.

Qui, M. and Green, S.H., "NGF and EGF Rapidly Activate $p21^{ras}$ in PC12 Cells by Distinct, Convergent Pathways Involving Tyrosine Phosphorylation", *Neuron*, 1991, 7, 937–946.

Qui and Green, "PC12 Cell Neuronal Differentiation is Associated with Prolonged $p21^{ras}$ Activity and Consequent Prolonged ERK Activity", *Neuron*, 1992, 9, 715–717.

Roberts, et al., "Transforming growth factor–β: multifunctional regulator of differentiation and development", *Phil. Trans. R. Soc. Lond.*, 1990, 327, 145–154.

Renfranz, et al., "Region–Specific Differentiation of the Hippocampal Stem Cell Line HiB5 upon Implantation into the Developing Mammalian Brain", *Cell*, 1991, 66, 713–729.

Romeo, et al., "Point mutations affecting the tyrosine kinase domain of the RET proto–oncogene in Hirschsprung's disease", *Nature*, 1994, 367, 377–378.

Rosenzweig, et al., "Cloning and characterization of a human type II receptor for bone morphogenetic proteins", *Proc. Natl. Acad. Sci. USA*, 1995, 92, 7632–7636.

Salazar–Grueso, et al., "Embryonic mouse spinal cord motor neuron hybrid cells", *NeuroReport*, 1991, 2, 505–508.

Santoro, et al., "An Epidermal Growth Factor Receptor/ret Chimera Generates Mitogenic and Transforming Signals: Evidence for a ret–Specific Signaling Pathway", *Mol. And Cell. Biol.*, 1994, 14, 663–675.

Santoro, et al., "The ret proto–oncogene is consistently expressed in human pheochromocytomas and thyroid medullary carcinomas", *Oncogene*, 1990, 5, 1595–1598.

Schuchardt, et al., "Defects in the kidney and enteric nervous system of mice lacking the tyrosine kinase receptor Ret", *Nature*, 1994, 367, 380–383.

Shihabuddin, et al., "The Adult CNA Retains the Potential to Direct Region–Specific Differentiation of a Transplanted Neuronal Precursor Cell Line", *J. Neurosci.*, 1995, 15, 6666–6678.

Snyder, et al., "Multipotent Neural Cell Lines Can Engraft and Participate in Development of Mouse Cerebellum",*Cell*, 1992, 68, 33–51.

Suvanto, et al., "Localization of Glial Cell Line–derived Neurotrophic Factor (GDNF) mRNA in Embryonic Rat by In Situ Hybridization", *Eur. J. Neurosci.*, 1996, 8, 815–822.

Tahira, et al., "Characterization of ret proto–oncogene mRNAs encoding two isoforms of the protein product in a human neuroblastoma cell line", *Oncogene*, 1990, 5, 97–102.

Takahashi, et al., "R–banding and nonisotopic in situ hybridization: precise localization of the human type II collagen gene (COL2A1)", *Hum. Genet.*, 1990, 86, 14–16.

Takahashi, et al., "Activation of a Novel Human Transforming Gene, ret, by DNA Rearrangement", *Cell*, 1985, 42, 581–588.

Takahashi, et al, "Cloning and expression of the ret proto–oncogene encoding a tyrosine kinase with two potential transmembrane domains", *Oncogene*, 1988, 3, 571–578.

Thomas, et al., "Ras Is Essential for Nerve Growth Factor–and Phorbol Ester–Induced Tyrosine Phosphorylation of MAP Kinases", *Cell*, 1992, 68, 1031–1040.

Tomac, et al., "Protection and repair of the nigrostriatal dopaminergic system by GDNF in vivo", *Nature*, 1995, 373, 335–339.

Trupp, et al., "Peripheral Expression and Biological Activities of GDNF, a New Neurotrophic Factor for Avian and Mammalian Peripheral Neurons", *J. Cell Biol.*, 1995, 130, 137–148.

Treanor, et al., "Characterization of a multicomponent receptor for GDNF", *Nature*, 1996, 382, 80–83.

Treanor, et al., "Characterization of GDNF binding to putative GDNF receptor", *Soc. Neurosci.*, 1995, 21, 1301, Abstract No. 515–14.

Tsuzuki, et al., "Spatial and temporal expression of the ret proto–oncogene product in embryonic, infant and adult rat tissues", *Oncogene*, 1995, 10, 191–198.

Whittemore, S.R. and White, L.A., "Target regulation of neuronal differentiation in a temperature–sensitive cell line derived from medullary raphe", *Brain Res.*, 1993, 615, 27–40.

Wilkinson, D.C. and Green, J., Postimplantation Mammalian Embryos, A Practical Approach, Chapter 8, IRL Press, Oxford University Press, Copp. A.J. and Crockoft D.L., eds., pp. 155–170 (1990).

Wood, et al., "ras Mediates Nerve Growth Factor Receptor Modulation of Three Signal–Transducing Protein Kinases-:MAP Kinase, Raf–1, and RSK", *Cell*, 1992, 68, 1041–1050.

Wrana, et al., "Mechanism of activation of the TGF–β receptor", *Nature*, 1994, 370, 341–347.

Wurst, W. And Joyner, A., "Gene Targeting, A Practical Approach", Joyner, A.L., Ed., Chapter 2, IRL Press Oxford University Press, NY. NY. pp. 33–61 (1993).

Yan, et al., "Two Different Signal Transduction Pathways Can Be Activated by Transforming Growth Factor β1 in Epithelial Cells", *J. Biol. Chem.*, 1994, 269, 13231–13237.

Yan, et al., "In vivo neurotrophic effects of GDNF on neonatal and adult facial motor neurons", *Nature*, 1995, 373, 341–344.

\* cited by examiner

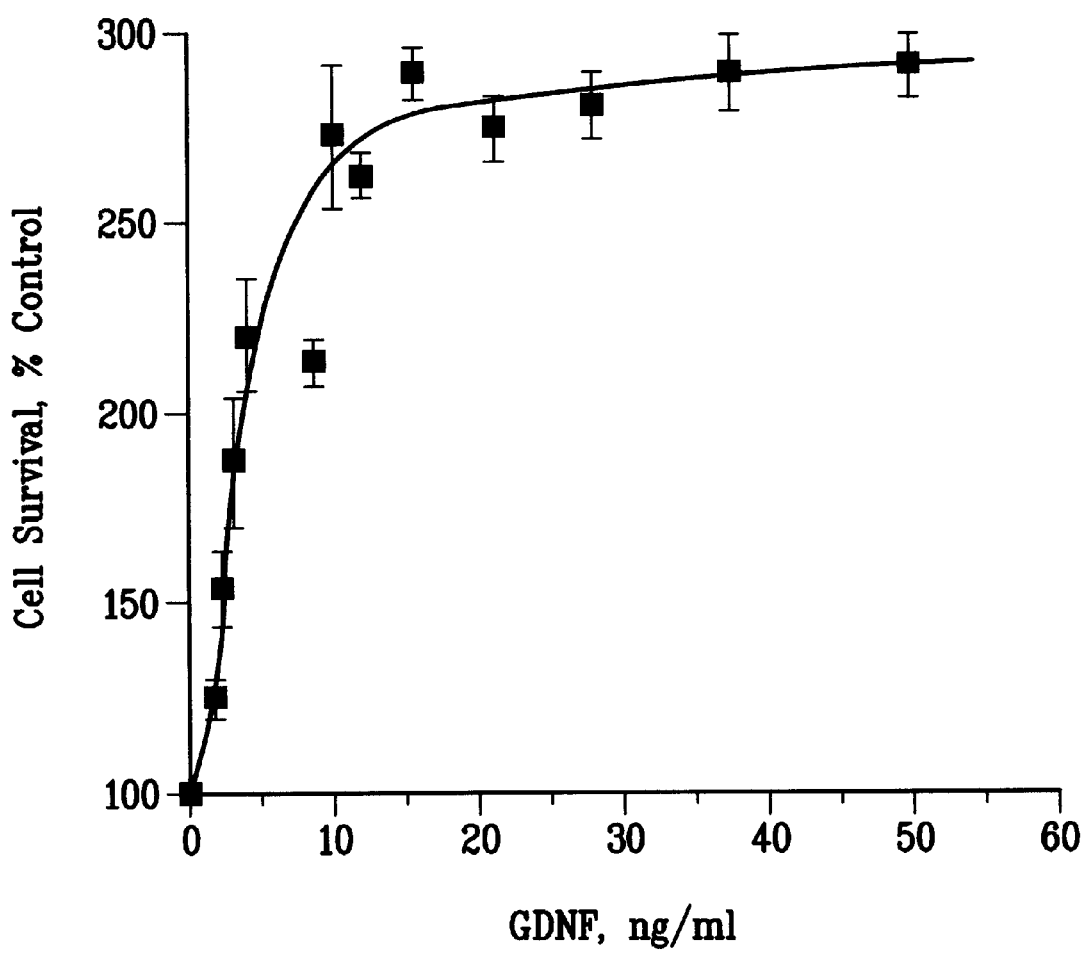

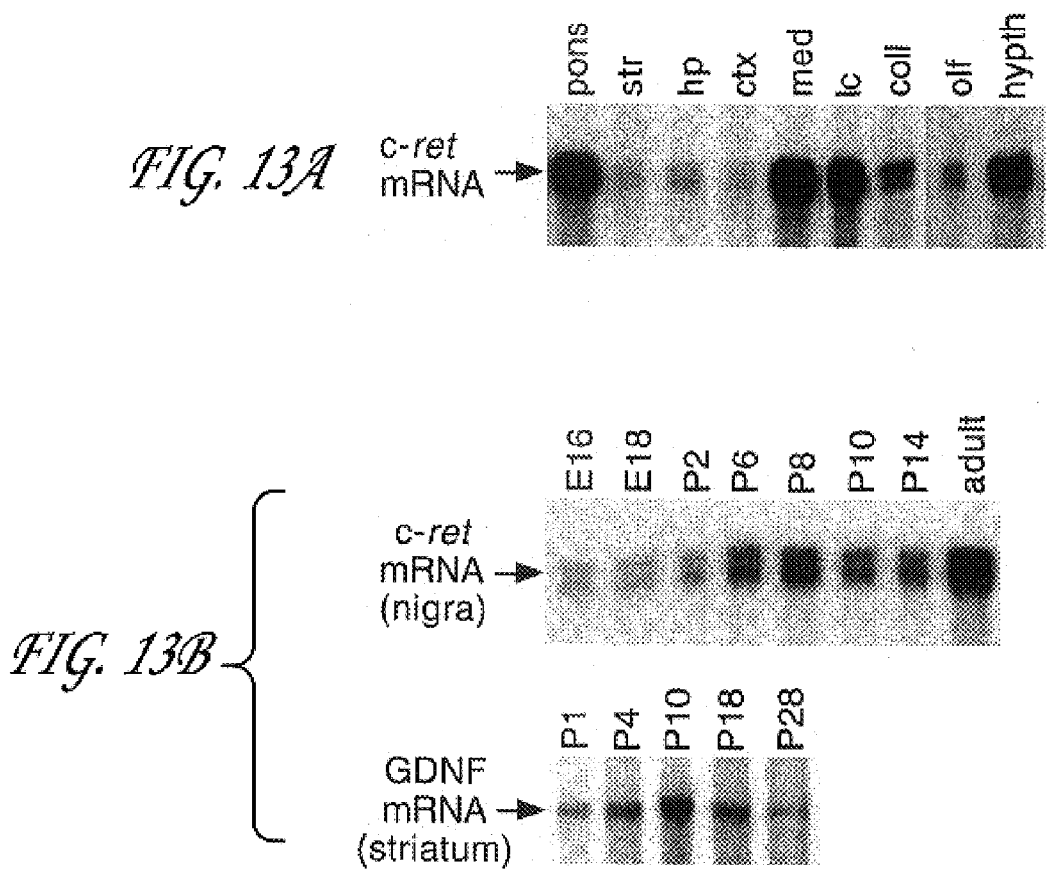
*FIG. 13A*
*FIG. 13B*
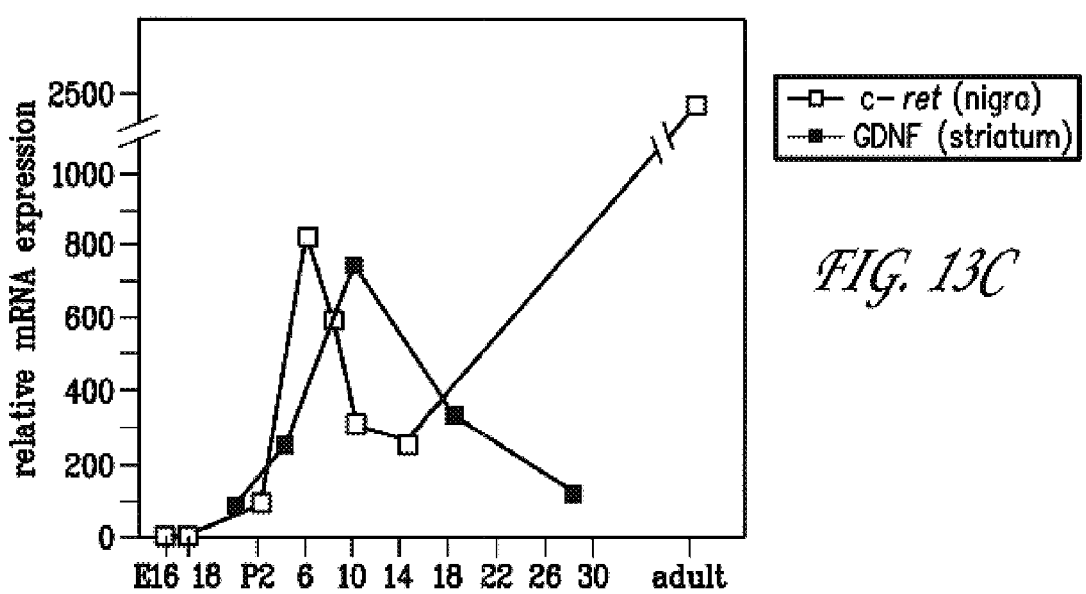
*FIG. 13C*

FIG. 14A
FIG. 14D
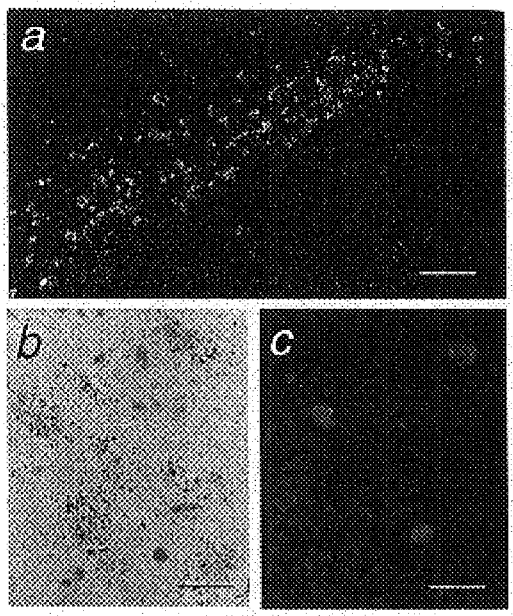
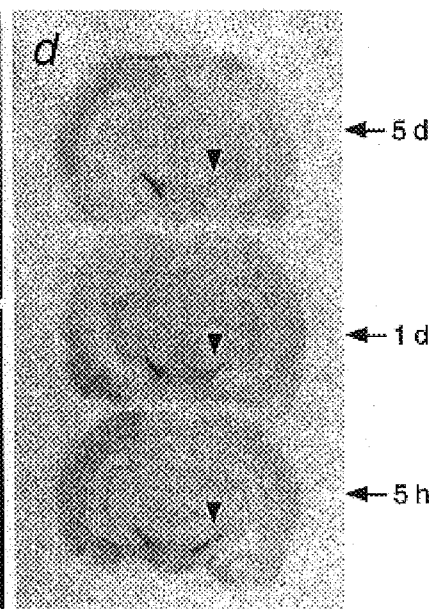
FIG. 14B  FIG. 14C
FIG. 14E  FIG. 14F
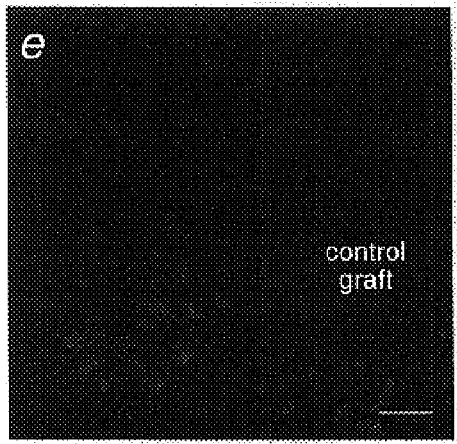
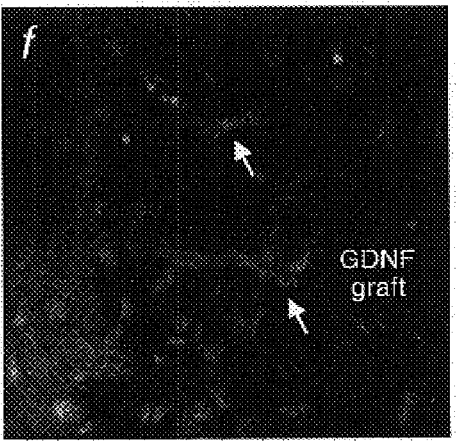
FIG. 14G  FIG. 14H

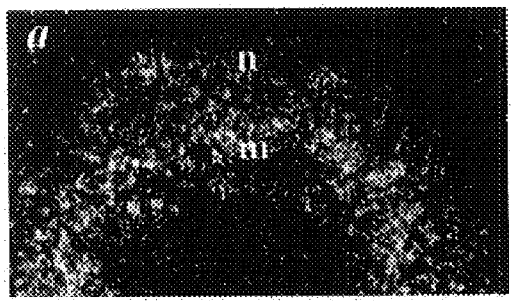
FIG. 19A
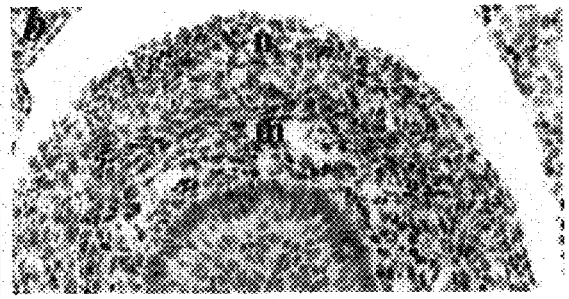
FIG. 19B
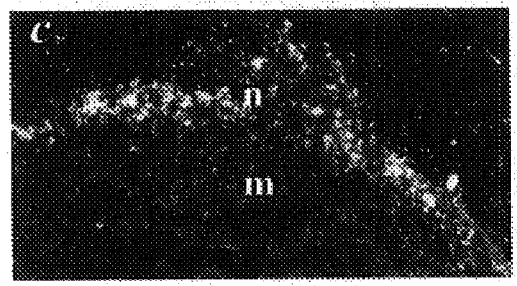
FIG. 19C
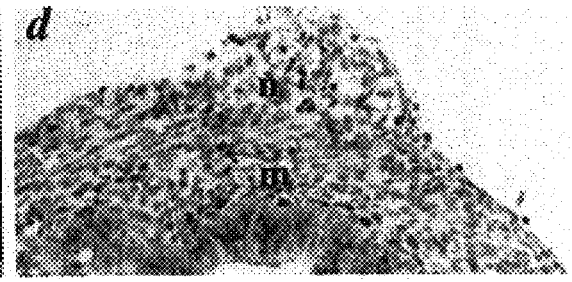
FIG. 19D
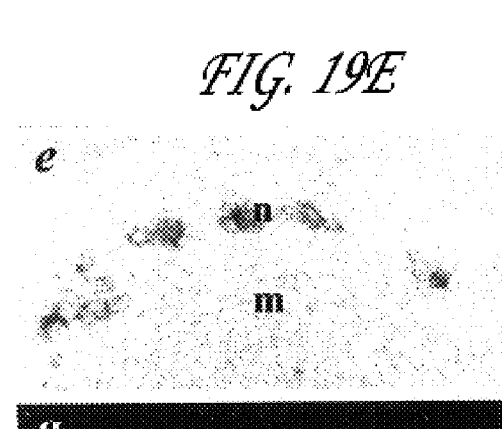
FIG. 19E
FIG. 19G
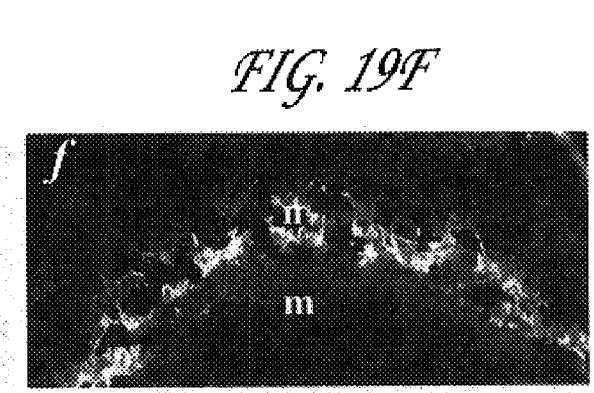
FIG. 19F
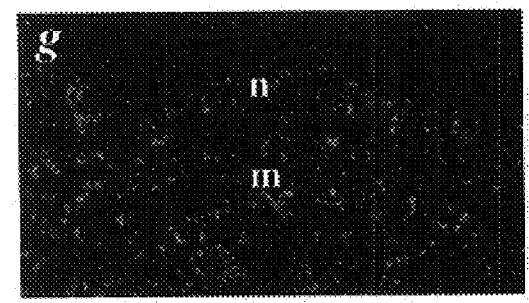
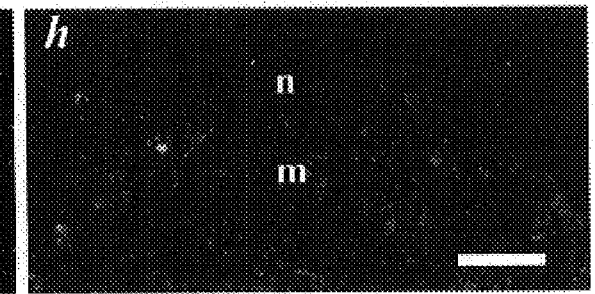
FIG. 19H FIG. 20A
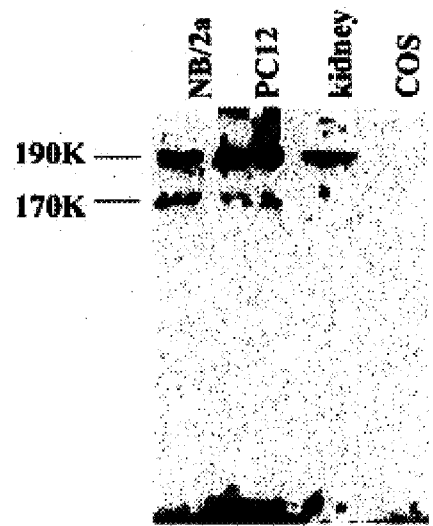
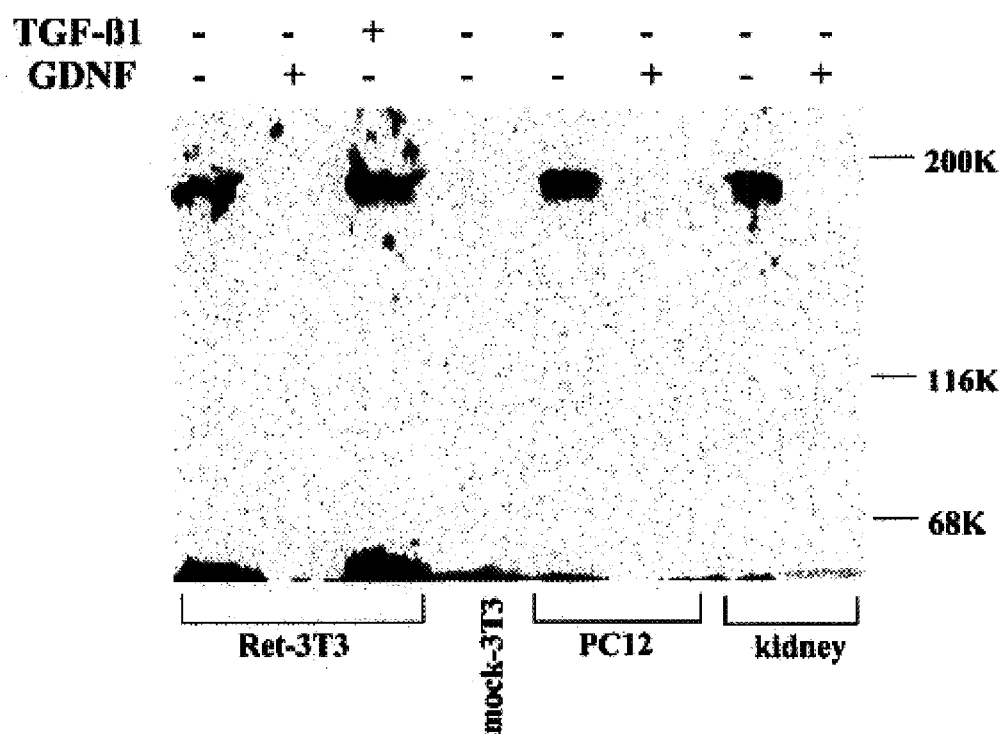
FIG. 20B

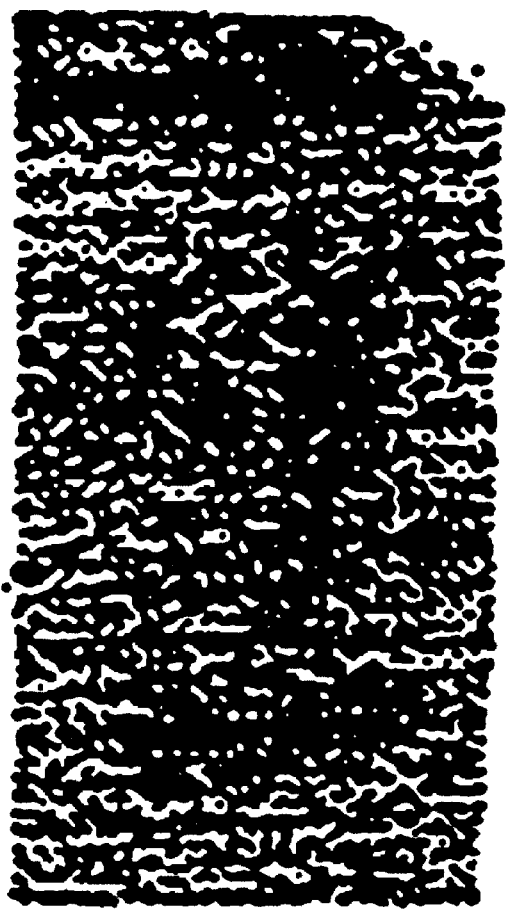

```
  1 MILANAFCLF FFLDETLRSL ASPSSLQGSE LHGWRPQVDC VRANELCAAE
 51 SNCSSRYRTL RQCLAGRDRN TMLANKECQA ALEVLQESPL YDCRCKRGMK
101 KELQCLQIYW SIHLGLTEGE EFYEASPYEP VTSRLSDIFR LASIFSGTGT
151 DPAVSTKSNH CLDAAKACNL NDNCKKLRSS YISICNREIS PTERCNRRKC
201 HKALRQFFDR VPSEYTYRML FCSCQDQACA ERRRQTILPS CSYEDKEKPN
251 CLDLRSLCRT DHLCRSRLAD FHANCRASYR TITSCPADNY QACLGSYAGM
301 IGFDMTPNYV DSNPTGIVVS PWCNCRGSGN MEEECEKFLR DFTENPCLRN
351 AIQAFGNGTD VNMSPKGPSL PATQAPRVEK TPSLPDDLSD STSLGTSVIT
401 TCTSIQEQGL KANNSKELSM CFTELTTNIS PGSKKVIKLN SGSSRARLSA
451 ALTALPLLML TLAL SEQ ID NO:2
```

```
GDNFR-β   1 MILANAFCLFFFLDETLRSLASPSSLQGSELHGWRPQVDCVRANELCAAE  50
            |:||. :  : :||  :.. .|.:.           .:|||:|.:  |   |
GDNFR-α   1 MFLATLYFALPLLDLLMSAEVSGGD...........RLDCVKASDQCLKE  39

51 SNCSSRYRTLRQCLAGRDRN.....TMLANKECQAALEBLQESPLYDCRC  95
            .||.:|||||||:||::  |       .: |..||..|:|.|.:...||:|||
         40 QSCSTKYRTLRQCVAGKETNFSLTSGLEAKDECRSAMEALKQKSLYNCRC  89

96 KRGMKKELQCLQIYWSYHLGLTEGEEFYEASPYEPVTSRLSDIFRLASIF 145
            |||||||  .||.||||:.  :|  :|:::.|.||||||.|||||||| ..::
         90 KRGMKKEKNCLRIYWSMYQSL.QGNDLLEDSPYEPVNSRLSDIFRAVPFI 138

146 SGTGTDPAVSTKSNHCLDAAKACNLNDNCKKLRSSHISICNREISPTERC 195
            |:.     :...    .|:|:||||||||||:|.|||.||.||. |. ..:| .| |
        139 SDVFQQVEHISKGNNCLDAAKACNLDDTCKKYRSAYITPCTTSMS.NEVC 187

196 NRRKCHKALRQFFDRVPSEYTYRMLFCSCQDQACAERRRQTILPSCSYED 245
            ||||||||||||||:||....| |||||||.| ||.|||||||||:| ||||:
        188 NRRKCHKALRQFFDKVPAKHSYGMLFCSCRDIACTERRRQTIVPVCSYEE 237

246 KEKPNCLDLRSLCRTDHLCRSRLADFHANCRASYRTITSCPADNYQACLG 295
            :|:||||.|..  |:|:..:|||||||| .||.:. |.:..|  :||..||
        238 RERPNCLSLQDSCKTYNICRSRLADFFTNCQPESRSVSNCLKENYADCLL 287

296 SYAGMIGFDMTPNYVDSNPTGIVVSPWCNCRGSGNMEEECEKFLRDFTEN 345
            .|.|:||  |||||||  .::  |.|||:|..|||   |.| |||. |.:|
        288 AYSGLIGTVMTPNYVDS..SSLSVAPWCDCSNSGNDLEDCLKFLNFFKTN 335

346 PCLRNAIQAFGNGTDVNMSPKGPSLPATQAPRVEKTPSLPDDLSDSTS.. 393
            .||:||||||||||.||.|...:|.:...| |. ..  .    ..|:...|
        336 TCLKNAIQAFGNGSDVTMWQPAPPVQTTTTATTTTAFRVKNKPLGPAGSEN 385

394 .LGTSVITTCTSIQEQGLKAN..NSKELSMCFTELTTNISPGSKKVIKLN 440
            :.|  |:...|...:|.|  ||.|  .|...|:::  .::..:  :|... |. .
        386 EIPTHVLPPCANLQAQKLKSNVSGSTHLCLSDSDFGKDGLAGASSHITTK 435

441 SGSSRARLSAALTALPLIMLTLAL*........... 465 SEQ ID NO: 2
            |  .  |.  |...|..||:|||| ||
        436 SMA..APPSCSLSSLPVLMLT.ALAALLSVSLEATS 468 SEQ ID NO: 1
```

```
humalpha  MFLATIYFALPLIDLLLSA..........EVSGGDRLDCVKASDQCLKEQSCSTKYRTLRQCVAGKETN          59
ratalpha  MFLATIYFALPLIDLLLMSA.........EVSGGDRLDCVKASDQCLKEQSCSTKYRTLRQCVAGKETN          59
ratbeta   MILANAFCLFFFLDETLRSLASPSSLQGSELHGWRPQVDCVRANELCAAESNCSSRYRTLRQCLAGRDRN          70
humbeta   MILANAFCLFFFLDETLRSLASPSSLQGPELHGWRPPVDCVRANELCAAESNCSSRYRTLRQCLAGRDRN          70 humalpha  FSLASGLEAKDECRSAMEALKQKSLYNCRCKRGMKKEKNCLRIYWSMYQSL.QGNDLLEDSPYEPVNSRL         128
ratalpha  FSLTSGLEAKDECRSAMEALKQKSLYNCRCKRGMKKEKNCLRIYWSMYQSL.QGNDLLEDSPYEPVNSRL         128
ratbeta   .....TMLANKECQAALEBLQESPLYDCRCKRGMKKELQCLQIYWSYHLGLTEGEEFYEASPYEPVTSRL         135
humbeta   .....TMLANKECQAALEBLQESPLYDCRCKRGMKKELQCLQIYWSYHLGLTEGEEFYEASPYEPVTSRL         135 humalpha  SDIFRVVPFISDVFQQVEHIPKGNNCLDAAKACNLDDICKKYRSAYITPCTTSVS.NDVCNRRKCHKALR         198
ratalpha  SDIFRAVPFISDVFQQVEHISKGNNCLDAAKACNLDDTCKKYRSAYITPCTTSMS.NEVCNRRKCHKALR         198
ratbeta   SDIFRLASIFSGTGTDPAVSTKSNHCLDAAKACNLNDNCKKLRSSYISICNREISPTERCNRRKCHKALR         205
humbeta   SDIFRLASIFSGTGADPVVSAKSNHCLDAAKACNLNDNCKKLRSSYISICNREISPTERCNRRKCHKALR         205 humalpha  QFFDKVPAKHSYGMLFCSCRDIACTERRQTIVPVCSYEREKPNCLSLQDSCKTNYICRSRLADFFTNC          268
ratalpha  QFFDKVPAKHSYGMLFCSCRDIACTERRQTIVPVCSYEERERPNCLSLQDSCKTNYICRSRLADFFTNC         268
ratbeta   QFFDRVPSEYTYRMLFCSCQDQACAERRQTILPSCSYEDKEKPNCLDLRSICRTDHLCRSRLADFHANC         275
humbeta   QFFDRVPSEYTYRMLFCSCQDQACAERRQTILPSCSYEDKEKPNCLDLRGVCRTDHLCRSRLADFHANC         275 humalpha  QPESRSVSSCLKENYADCLLAYSGLIGTVMTPNYIDSS...SLSVAPWCDCSNSGNDLEECLKFLNFFKDN        336
ratalpha  QPESRSVSNCLKENYADCLLAYSGLIGTVMTPNYVDSS...SLSVAPWCDCSNSGNDLEDCLKFLNFFKDN        336
ratbeta   RASYRITTSCPADNYQACLGSYAGMIGFDMTPNYMDSNPTGIVSPWCNCRGSGNMEEECEKFLRDFTEN         345
humbeta   RASYQITVTSCPADNYQACLGSYAGMIGFDMTPNYVDSSPTGIVSPWCNCRGSGNMEEECEKFLRDFTEN         345 humalpha  TCLKNAIQAFGNGSDVTVWQPAFPVQTTATTTALRVKNKPLGPAGSENEIPTHVLPPCANLQAQKLKS          406
ratalpha  TCLKNAIQAFGNGSDVTMWQPAPPVQTTATTTAFRVKNKPLGPAGSENEIPTHVLPPCANLQAQKLKS          406
ratbeta   PCLRNAIQAFGNGTDVNMSPKGPSLPATQAPRVEKTPSLPDDLSDSTS...LGTSVITTCTSIQEQGLKA        412
humbeta   PCLRNAIQAFGNGTDVNVSPKGPSFQATQAPRVEKTPSLPDDLSDSTS...LGTSVITTCTSVQEQGLKA        412 humalpha  NVSGNTHLCISNGNYEKEGL.GASSHITTKSMA..APPSCGLSPLLVRVVTALSTLL..SLTETS*         465    SEQ ID NO.: 8
ratalpha  NVSGSTHLCLSDSDFGKDGLAGASSHITTKSMA..APPSCSLSSLPVLMLTALAALLSVSLEATS*         465    SEQ ID NO.: 1
ratbeta   NNSKELSMCFTE..LTTNISPGSKKVIKLNSGSSL............................          445    SEQ ID NO.: 2
humbeta   NNSKELSMCFTE..LTTNIIPGSNKVIKPNSGSSRARPSAALTVLSVLMLKQAL*                   464    SEQ ID NO.: 9
```

1: control plasmid
2: comtrol plasmid + cold
3: GDNFR-α
4: GDNFR-α + cold
5: GDNFR-β
6: GDNFR-β + cold
7: c-Ret + GDMFR-α
8: c-Ret + GDMFR-α + cold
9: c-Ret + GDMFR-β
10: c-Ret + GDMFR-β + cold
11: c-Ret
12: c-Ret + cold 1: RN33B
2: COS transfected with Ret and GDNFR-α
3: COS transfected with Ret and GDNFR-β

FIG. 31
COS cells transfected with c-Ret
and GDNFR-α or GDNFR-β cDNAs
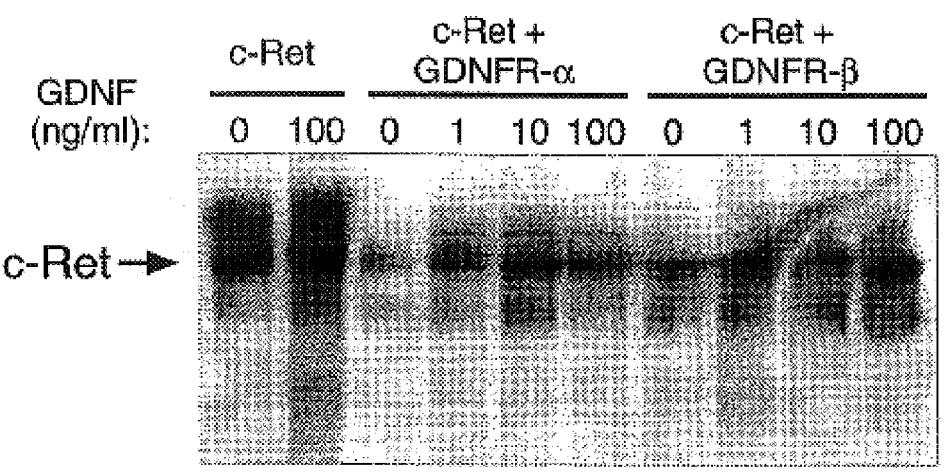
Neuro-2A cells transfected with
GDNFR-α or GDNFR-β cDNAs
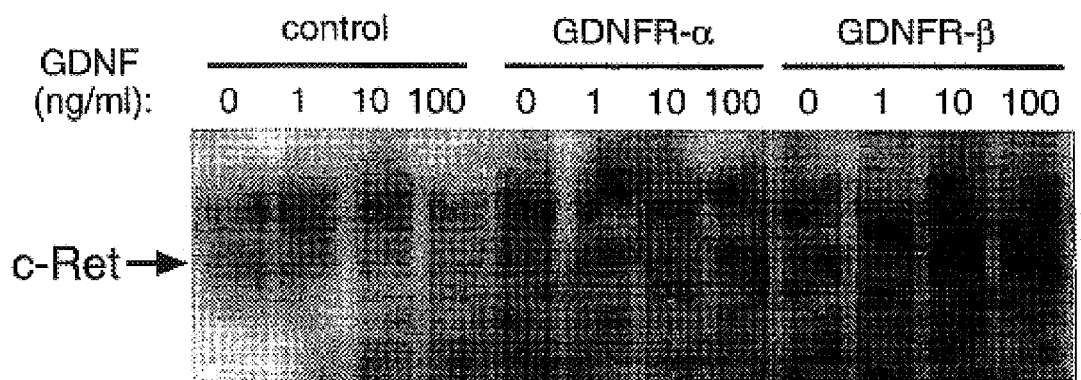

FIG. 32

```
   1  ATGATCTTGG CAAACGCCTT CTGCCTCTTC TTCTTTTTAG ACGAAACCCT
  51  CCGCTCTTTG GCCAGCCCTT CCTCCCTGCA GGGCTCTGAG CTCCACGGCT
 101  GGCGCCCCCA AGTGGACTGT GTCCGGGCCA ATGAGCTGTG TGCGGCTGAA
 151  TCCAACTGCA GCTCCAGGTA CCGCACCCTT CGGCAGTGCC TGGCAGGCCG
 201  GGATCGCAAT ACCATGCTGG CCAATAAGGA GTGCCAGGCA GCCCTGGAGG
 251  TCTTGCAGGA AAGCCCACTG TATGACTGCC GCTGCAAGCG GGGCATGAAG
 301  AAGGAGCTGC AGTGTCTGCA GATCTACTGG AGCATCCATC TGGGGCTGAC
 351  AGAGGGTGAG GAGTTCTATG AAGCTTCCCC CTATGAGCCT GTGACCTCGC
 401  GCCTCTCGGA CATCTTCAGG CTCGCTTCAA TCTTCTCAGG GACAGGGACA
 451  GACCCGGCAG TCAGTACCAA AAGCAACCAC TGCCTGGATG CCGCCAAGGC
 501  CTGCAACCTG AATGACAACT GCAAGAAGCT TCGCTCCTCT TATATCTCCA
 551  TCTGCAACCG TGAGATCTCT CCCACCGAAC GCTGCAACCG CCGCAAGTGC
 601  CACAAGGCTC TGCGCCAGTT CTTTGACCGT GTGCCCAGCG AGTATACCTA
 651  CCGCATGCTC TTCTGCTCCT GTCAGGACCA GGCATGTGCT GAGCGTCGCC
 701  GGCAAACCAT CCTGCCCAGT TGCTCCTATG AGGACAAGGA GAAGCCCAAC
 751  TGCCTGGACC TGCGCAGCCT GTGTCGTACA GACCACCTGT GCCGGTCCCG
 801  ACTGGCAGAT TTCCACGCCA CTGTCGAGC CTCCTACCGG ACAATCACCA
 851  GCTGTCCTGC GGACAACTAC CAGGCATGTC TGGGCTCCTA TGCTGGCATG
 901  ATTGGGTTTG ATATGACACC CAACTATGTG GACTCCAACC CCACGGGCAT
 951  CGTGGTGTCT CCCTGGTGCA ATTGTCGTGG CAGTGGGAAC ATGGAAGAAG
1001  AGTGTGAGAA GTTCCTCAGG GACTTCACGG AAAACCCATG CCTCCGGAAT
1051  GCCATTCAGG CCTTTGGTAA TGGCACAGAT GTGAACATGT CTCCCAAAGG
1101  CCCCTCACTC CCAGCTACCC AGGCCCCTCG GGTGGAGAAG ACTCCTTCAC
1151  TGCCAGATGA CCTCAGTGAC AGCACCAGCC TGGGGACCAG TGTCATCACC
1201  ACCTGCACAT CTATCCAGGA GCAAGGGCTG AAGGCCAACA ACTCCAAAGA
1251  GTTAAGCATG TGCTTCACAG AGCTCACGAC AAACATCAGT CCAGGGAGTA
1301  AAAAGGTGAT CAAACTTAAC TCAGGCTCCA GCAGAGCCAG ACTGTCGGCT
1351  GCCTTGACTG CCCTCCCACT CCTGATGCTG ACCTTGGCCT TGTAGGCCTT
1401  TGGAACCCAG CACA SEQ ID NO: 5
```

```
5'  ATGATCTTGGCAAACGCCTTCTGCCCTCTTCTTCTTTCTAGACGAGACCCTCCGCTCTTGGCCAGCCCTTCCTCCCTGCA      80
    GGGCCCCGAGCTCCACGGCTCCTGGCGCTGGGGCGCCCCCAGTGACTGTCCGGCCAATGAGCTGTGCCGCCGAATCCAACTGCA  160
    GCTCTCGCTACCGCACTCTGCGCGCAGTGCCTGGCCAGCCCGCTGCGCGACCGCCAACACCATGCTGCCAACAAGGAGTGCCAGGCG  240
    GCCTTGGAGGTCTTGCAGGAGAGCCCGCTGTACGACGGCAAGCGGGCATGAAGAAGGAGCTGCAGTGTCTGGA  320
    GATCTACTGGAGCATCCACCTGGGCTGAGGGTGAGAGTTCTACGAAGCCTCCCCGGTTGAGCCGGTGACCTCC  400
    GCCCTCCGGACATCTTCAGGCTTGCTCTTCAATCTTTCAGGACAGGGCAGAGACCCGGTGTCAGCGCCAAGAGCAACCAT  480
    TGCCTGGATGCTGCCAAGGCCTGCAACCTGAATGACAACTGCAAGAAGCTGCGCTCCTCCTACATCTCATCTGCAACCG  560
    CGAGATCTCGCCCCACCGAGCGCTGCTCTTCTGCTCCTGCCAAGACCAAGGCCGTGCGTGAGCGCCCTGCGCTGCCAGCG  640
    AGTACACCTACCGCCATGCTCTTCTGCTCCTGCCAAGAGAAGCCCAACTCGTCTGGATCTGACCACATCCTGCCCAGC  720
    TGCTCCTATGAGGACAAGGAGAGCCCAATTGCCAATGTCGAGCCTGTCACCAGCCGCTGTGTGCCACCTGTCGGTCCCG  800
    GCTGGCCGACTTCCATGCCAATGCCAATTGTCGAGCCTGTCACCAGCCGCTGCCCTGCGGACACTGCCACTCTGGTGTCC  880
    TGGGCTCTTATGCTGCATGATGATTGGGTTGACATGAGGAGGAGTGAGAAGTTCCTCAGGACTTCACCGAGAACCCATG   960
    CCCTGGTGCAGCTGTCGTGGGCAACATGAGCGGGAACATGAGCGGAAGTCTGAACGTGTCCCCAAAAGGCCCCTCCAGGCCACCC 1040
    CCTCCGGAACGCAGCCATCCAGCCCTTTGGCAGCGCCTTCTTTGCCAGATGACGCCTCAGTGACCTCCAGTTGCTTCATCACC 1120
    AGGCCCCTCGGGTGGAGAAGACGCCTTCTTGCCAGTGGCTGCCAGGGGGCCAGGGGCCAGGTACCAGGAAGAGTTAAGCATGTGCTTCACAGAGCTCACGAC 1200
    ACCTGCACGTCTGTCCAGGAGCTCCAGGAGTAACAAGGTGATCAACTAACTCAGGCCCCAGCAGAGCCCAGCCGACTCGGCTGCCTTGACCG 1280
    AAATATCATCCAGGAGTAACAAGGTGATCAACTAACTCAGGCCCTTGTAGGCTGTGGGAACACAGAGACCACACACCTTGC-3' 1360
    TGCTGTGTCCTGATGCTGAAATGGAAACAGGCCTTGTAGGCTGTGGGAACACAGAGACCACACACCTTGC-3' 1440
    AACAGCGCCTGACGAAATGGAAACAGAGACCACAGAGACCACACACCTTGC-3'                              1490

SEQ ID NO.: 10
```

FIG. 33

FIG. 37A  FIG. 37B  FIG. 37C
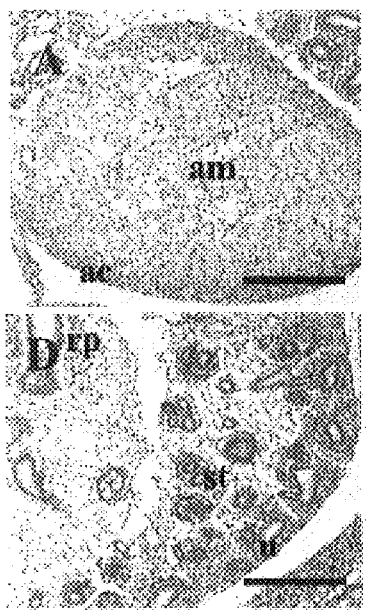 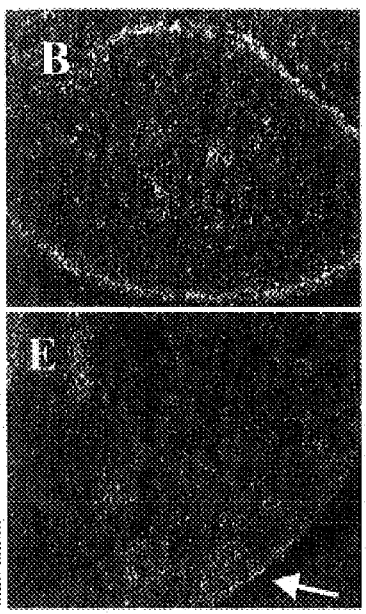 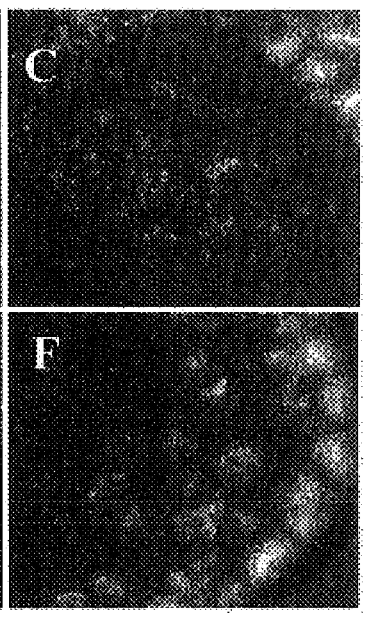
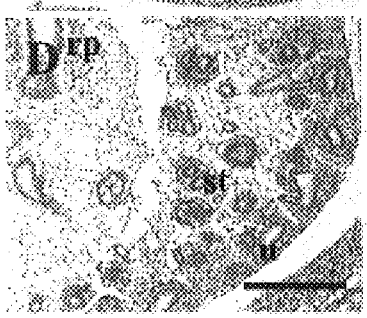 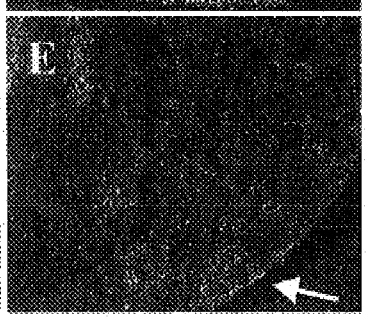 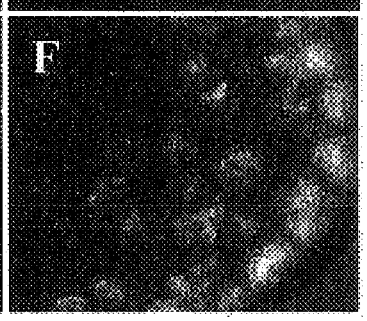
FIG. 37D  FIG. 37E  FIG. 37F FIG. 37G  FIG. 37H  FIG. 37I
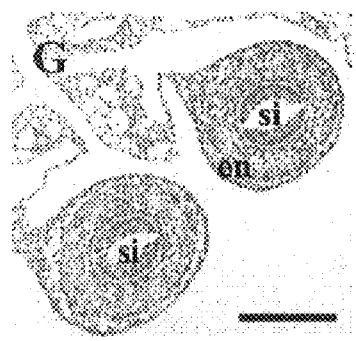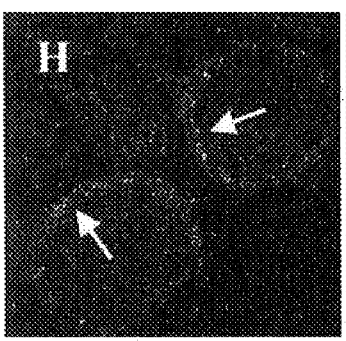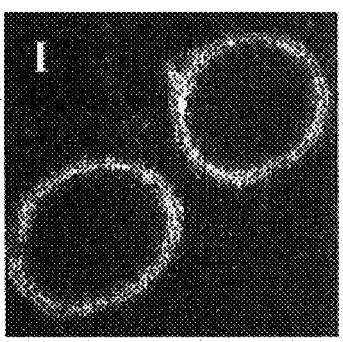
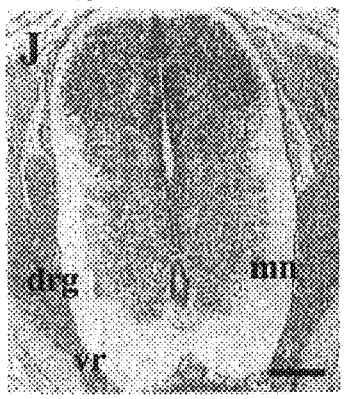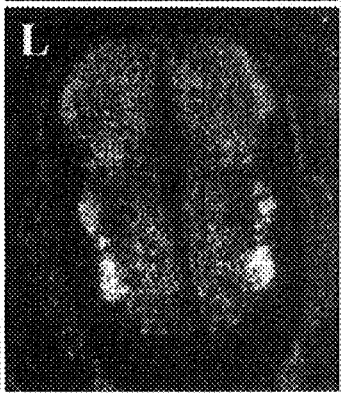
FIG. 37J  FIG. 37K  FIG. 37L

SEQUENCE LISTING

<160> NUMBER OF SEQ ID NOS: 11

<210> SEQ ID NO 1
<211> LENGTH: 468
<212> TYPE: PRT
<213> ORGANISM: Rattus sp.

<400> SEQUENCE: 1

Met Phe Leu Ala Thr Leu Tyr Phe Ala Leu Pro Leu Leu Asp Leu Leu
 1               5                  10                  15

Met Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Thr Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Ala Val Pro Phe Ile Ser Asp Val Phe Gln Gln
    130                 135                 140

Val Glu His Ile Ser Lys Gly Asn Asn Cys Leu Asp Ala Ala Lys Ala
145                 150                 155                 160

Cys Asn Leu Asp Asp Thr Cys Lys Lys Tyr Arg Ser Ala Tyr Ile Thr
                165                 170                 175

Pro Cys Thr Thr Ser Met Ser Asn Glu Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Arg
225                 230                 235                 240

Pro Asn Cys Leu Ser Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Asn Cys Leu Lys Glu Asn Tyr Ala Asp Cys Leu Leu Ala
        275                 280                 285

Tyr Ser Gly Leu Ile Gly Thr Val Met Thr Pro Asn Tyr Val Asp Ser

```
                    290                 295                 300
Ser Ser Leu Ser Val Ala Pro Trp Cys Asp Cys Ser Asn Ser Gly Asn
305                 310                 315                 320

Asp Leu Glu Asp Cys Leu Lys Phe Leu Asn Phe Phe Lys Asp Asn Thr
                325                 330                 335

Cys Leu Lys Asn Ala Ile Gln Ala Phe Gly Asn Gly Ser Asp Val Thr
                340                 345                 350

Met Trp Gln Pro Ala Pro Val Gln Thr Thr Ala Thr Thr Thr
                355                 360                 365

Thr Ala Phe Arg Val Lys Asn Lys Pro Leu Gly Pro Ala Gly Ser Glu
370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Ser Thr His Leu Cys Leu Ser
                405                 410                 415

Asp Ser Asp Phe Gly Lys Asp Gly Leu Ala Gly Ala Ser Ser His Ile
                420                 425                 430

Thr Thr Lys Ser Met Ala Ala Pro Pro Ser Cys Ser Leu Ser Ser Leu
                435                 440                 445

Pro Val Leu Met Leu Thr Ala Leu Ala Ala Leu Leu Ser Val Ser Leu
                450                 455                 460

Ala Glu Thr Ser
465

<210> SEQ ID NO 2
<211> LENGTH: 464
<212> TYPE: PRT
<213> ORGANISM: Rattus sp.

<400> SEQUENCE: 2

Met Ile Leu Ala Asn Ala Phe Cys Leu Phe Phe Leu Asp Glu Thr
 1               5                  10                  15

Leu Arg Ser Leu Ala Ser Pro Ser Ser Leu Gln Gly Ser Glu Leu His
                20                  25                  30

Gly Trp Arg Pro Gln Val Asp Cys Val Arg Ala Asn Glu Leu Cys Ala
            35                  40                  45

Ala Glu Ser Asn Cys Ser Ser Arg Tyr Arg Thr Leu Arg Gln Cys Leu
     50                  55                  60

Ala Gly Arg Asp Arg Asn Thr Met Leu Ala Asn Lys Glu Cys Gln Ala
65                  70                  75                  80

Ala Leu Glu Val Leu Gln Glu Ser Pro Leu Tyr Asp Cys Arg Cys Lys
                85                  90                  95

Arg Gly Met Lys Lys Glu Leu Gln Cys Leu Gln Ile Tyr Trp Ser Ile
                100                 105                 110

His Leu Gly Leu Thr Glu Gly Glu Glu Phe Glu Ala Ser Pro Tyr
            115                 120                 125

Glu Pro Val Thr Ser Arg Leu Ser Asp Ile Phe Arg Leu Ala Ser Ile
    130                 135                 140

Phe Ser Gly Thr Gly Thr Asp Pro Ala Val Ser Thr Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
                180                 185                 190
```

Glu Arg Cys Asn Arg Arg Lys Cys His Lys Ala Leu Arg Gln Phe Phe
            195                 200                 205

Asp Arg Val Pro Ser Glu Tyr Thr Tyr Arg Met Leu Phe Cys Ser Cys
210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Ser
            245                 250                 255

Leu Cys Arg Thr Asp His Leu Cys Arg Ser Arg Leu Ala Asp Phe His
            260                 265                 270

Ala Asn Cys Arg Ala Ser Tyr Arg Thr Ile Thr Ser Cys Pro Ala Asp
            275                 280                 285

Asn Tyr Gln Ala Cys Leu Gly Ser Tyr Ala Gly Met Ile Gly Phe Asp
            290                 295                 300

Met Thr Pro Asn Tyr Val Asp Ser Asn Pro Thr Gly Ile Val Val Ser
305                 310                 315                 320

Pro Trp Cys Asn Cys Arg Gly Ser Gly Asn Met Glu Glu Cys Glu
                325                 330                 335

Lys Phe Leu Arg Asp Phe Thr Glu Asn Pro Cys Leu Arg Asn Ala Ile
            340                 345                 350

Gln Ala Phe Gly Asn Gly Thr Asp Val Asn Met Ser Pro Lys Gly Pro
            355                 360                 365

Ser Leu Pro Ala Thr Gln Ala Pro Arg Val Glu Lys Thr Pro Ser Leu
            370                 375                 380

Pro Asp Asp Leu Ser Asp Ser Thr Ser Leu Gly Thr Ser Val Ile Thr
385                 390                 395                 400

Thr Cys Thr Ser Ile Gln Glu Gln Gly Leu Lys Ala Asn Asn Ser Lys
                405                 410                 415

Glu Leu Ser Met Cys Phe Thr Glu Leu Thr Thr Asn Ile Ser Pro Gly
            420                 425                 430

Ser Lys Lys Val Ile Lys Leu Asn Ser Gly Ser Ser Arg Ala Arg Leu
            435                 440                 445

Ser Ala Ala Leu Thr Ala Leu Pro Leu Leu Met Leu Thr Leu Ala Leu
            450                 455                 460

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 3
atggatccgc aacctgaatg acaactgc                                      28

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 4
ccgaattcag ttgggcttct ccttgtc                                       27

<210> SEQ ID NO 5
<211> LENGTH: 1414
<212> TYPE: DNA

<213> ORGANISM: Rattus sp.

<400> SEQUENCE: 5

| | | | | | |
|---|---|---|---|---|---|
| atgatcttgg | caaacgcctt | ctgcctcttc | ttcttttag | acgaaaccct | ccgctctttg | 60 |
| gccagcccctt | cctccctgca | gggctctgag | ctccacggct | ggcgccccca | agtggactgt | 120 |
| gtccgggcca | atgagctgtg | tgcggctgaa | tccaactgca | gctccaggta | ccgcaccctt | 180 |
| cggcagtgcc | tggcaggccg | ggatcgcaat | accatgctgg | ccaataagga | gtgccaggca | 240 |
| gccctggagg | tcttgcagga | aagcccactg | tatgactgcc | gctgcaagcg | ggcatgaag | 300 |
| aaggagctgc | agtgtctgca | gatctactgg | agcatccatc | tggggctgac | agagggtgag | 360 |
| gagttctatg | aagcttcccc | ctatgagcct | gtgacctcgc | gcctctcgga | catcttcagg | 420 |
| ctcgttcaat | tcttctcagg | acagggaca | gacccggcag | tcagtaccaa | aagcaaccac | 480 |
| tgcctggatg | ccgccaaggc | ctgcaacctg | aatgacaact | gcaagaagct | tcgctcctct | 540 |
| tatatctcca | tctgcaaccg | tgagatctct | tgagatctct | cccaccgaac | gctgcaaccg | 600 |
| cacaaggctc | tgcgccagtt | ctttgaccgt | gtgcccagcg | agtataccta | ccgcatgctc | 660 |
| ttctgctcct | gtcaggacca | ggcatgtgct | gagcgtcgcc | ggcaaaccat | cctgcccagt | 720 |
| tgctcctatg | aggacaagga | gaagcccaac | tgcctggacc | tgcgcagcct | gtgtcgtaca | 780 |
| gaccacctgt | gccggtcccg | actggcagat | ttccacgcca | actgtcgagc | ctcctaccgg | 840 |
| acaatcacca | gtcgtcctgc | ggacaactac | caggcatgtc | tgggctccta | tgctggcatg | 900 |
| attgggtttg | atatgacacc | caactatgtg | gactccaacc | ccacgggcat | cgtggtgtct | 960 |
| ccctggtgca | attgtcgtgg | cagtgggaac | atggaagaag | agtgtgagaa | gttcctcagg | 1020 |
| gacttcacgg | aaaacccatg | cctccggaat | gccattcagg | cctttggtaa | tgcacagat | 1080 |
| gtgaacatgt | ctcccaaagg | cccctcactc | ccagctaccc | aggcccctcg | ggtggagaag | 1140 |
| actccttcac | tgccagatga | cctcagtgac | agcaccagcc | tggggaccag | tgtcatcacc | 1200 |
| acctgcacat | ctatccagga | gcaagggctg | aaggccaaca | actccaaaga | gttaagcatg | 1260 |
| tgcttccacag | agctcacgac | aaacatcagt | ccagggagta | aaaaggtgat | caaacttaac | 1320 |
| tcaggctcca | gcagagccag | actgtcggct | gccttgactg | ccctcccact | cctgatgctg | 1380 |
| accttggcct | tgtaggcctt | tggaacccag | caca | | | 1414 |

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
atgatcttgg caaacgcctt ctg         23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
ttgcagttgt cattcaggtt gc         22

<210> SEQ ID NO 8
<211> LENGTH: 465

-continued

```
<212> TYPE: PRT
<213> ORGANISM: Homo sapiens

<400> SEQUENCE: 8

Met Phe Leu Ala Thr Leu Tyr Phe Ala Leu Pro Leu Leu Asp Leu Leu
  1               5                  10                  15

Leu Ser Ala Glu Val Ser Gly Gly Asp Arg Leu Asp Cys Val Lys Ala
             20                  25                  30

Ser Asp Gln Cys Leu Lys Glu Gln Ser Cys Ser Thr Lys Tyr Arg Thr
         35                  40                  45

Leu Arg Gln Cys Val Ala Gly Lys Glu Thr Asn Phe Ser Leu Ala Ser
     50                  55                  60

Gly Leu Glu Ala Lys Asp Glu Cys Arg Ser Ala Met Glu Ala Leu Lys
 65                  70                  75                  80

Gln Lys Ser Leu Tyr Asn Cys Arg Cys Lys Arg Gly Met Lys Lys Glu
                 85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Val Val Pro Phe Ile Ser Asp Val Phe Gln Gln
    130                 135                 140

Val Glu His Ile Pro Lys Gly Asn Asn Cys Leu Asp Ala Ala Lys Ala
145                 150                 155                 160

Cys Asn Leu Asp Asp Ile Cys Lys Lys Tyr Arg Ser Ala Tyr Ile Thr
                165                 170                 175

Pro Cys Thr Thr Ser Val Ser Asn Asp Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Lys
225                 230                 235                 240

Pro Asn Cys Leu Asn Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Ser Cys Leu Lys Glu Asn Tyr Ala Asp Cys Leu Leu Ala
        275                 280                 285

Tyr Ser Gly Leu Ile Gly Thr Val Met Thr Pro Asn Tyr Ile Asp Ser
    290                 295                 300

Ser Ser Leu Ser Val Ala Pro Trp Cys Asp Cys Ser Asn Ser Gly Asn
305                 310                 315                 320

Asp Leu Glu Glu Cys Leu Lys Phe Leu Asn Phe Phe Lys Asp Asn Thr
                325                 330                 335

Cys Leu Lys Asn Ala Ile Gln Ala Phe Gly Asn Gly Ser Asp Val Thr
            340                 345                 350

Val Trp Gln Pro Ala Phe Pro Val Gln Thr Thr Thr Ala Thr Thr Thr
        355                 360                 365

Thr Ala Leu Arg Val Lys Asn Lys Pro Leu Gly Pro Ala Gly Ser Glu
    370                 375                 380

Asn Glu Ile Pro Thr His Val Leu Pro Pro Cys Ala Asn Leu Gln Ala
385                 390                 395                 400
```

```
Gln Lys Leu Lys Ser Asn Val Ser Gly Asn Thr His Leu Cys Ile Ser
                405                 410                 415
Asn Gly Asn Tyr Glu Lys Glu Gly Leu Gly Ala Ser Ser His Ile Thr
            420                 425                 430
Thr Lys Ser Met Ala Ala Pro Pro Ser Cys Gly Leu Ser Pro Leu Leu
        435                 440                 445
Val Arg Val Val Thr Ala Leu Ser Thr Leu Leu Ser Leu Thr Glu Thr
    450                 455                 460
Ser
465

<210> SEQ ID NO 9
<211> LENGTH: 464
<212> TYPE: PRT
<213> ORGANISM: Homo sapiens

<400> SEQUENCE: 9

Met Ile Leu Ala Asn Ala Phe Cys Leu Phe Phe Leu Asp Glu Thr
  1               5                  10                  15
Leu Arg Ser Leu Ala Ser Pro Ser Ser Leu Gln Gly Pro Glu Leu His
             20                  25                  30
Gly Trp Arg Pro Pro Val Asp Cys Val Arg Ala Asn Glu Leu Cys Ala
         35                  40                  45
Ala Glu Ser Asn Cys Ser Ser Arg Tyr Arg Thr Leu Arg Gln Cys Leu
     50                  55                  60
Ala Gly Arg Asp Arg Asn Thr Met Leu Ala Asn Lys Glu Cys Gln Ala
 65                  70                  75                  80
Ala Leu Glu Val Leu Gln Glu Ser Pro Leu Tyr Asp Cys Arg Cys Lys
                 85                  90                  95
Arg Gly Met Lys Lys Glu Leu Gln Cys Leu Gln Ile Tyr Trp Ser Ile
            100                 105                 110
His Leu Gly Leu Thr Glu Gly Glu Phe Tyr Glu Ala Ser Pro Tyr
        115                 120                 125
Glu Pro Val Thr Ser Arg Leu Ser Asp Ile Phe Arg Leu Ala Ser Ile
    130                 135                 140
Phe Ser Gly Thr Gly Ala Asp Pro Val Val Ser Ala Lys Ser Asn His
145                 150                 155                 160
Cys Leu Asp Ala Ala Lys Ala Cys Asn Leu Asn Asp Asn Cys Lys Lys
                165                 170                 175
Leu Arg Ser Ser Tyr Ile Ser Ile Cys Asn Arg Glu Ile Ser Pro Thr
            180                 185                 190
Glu Arg Cys Asn Arg Arg Lys Cys His Lys Ala Leu Arg Gln Phe Phe
        195                 200                 205
Asp Arg Val Pro Ser Glu Tyr Thr Tyr Arg Met Leu Phe Cys Ser Cys
    210                 215                 220
Gln Asp Gln Ala Cys Ala Glu Arg Arg Gln Thr Ile Leu Pro Ser
225                 230                 235                 240
Cys Ser Tyr Glu Asp Lys Glu Lys Pro Asn Cys Leu Asp Leu Arg Gly
                245                 250                 255
Val Cys Arg Thr Asp His Leu Cys Arg Ser Arg Leu Ala Asp Phe His
            260                 265                 270
Ala Asn Cys Arg Ala Ser Tyr Gln Thr Val Thr Ser Cys Pro Ala Asp
        275                 280                 285
Asn Tyr Gln Ala Cys Leu Gly Ser Tyr Ala Gly Met Ile Gly Phe Asp
```

```
                  290                295                300
Met Thr Pro Asn Tyr Val Asp Ser Pro Thr Gly Ile Val Val Ser
305                 310                315                320

Pro Trp Cys Ser Cys Arg Gly Ser Gly Asn Met Glu Glu Cys Glu
                325                330                335

Lys Phe Leu Arg Asp Phe Thr Glu Asn Pro Cys Leu Arg Asn Ala Ile
                340                345                350

Gln Ala Phe Gly Asn Gly Thr Asp Val Asn Val Ser Pro Lys Gly Pro
                355                360                365

Ser Phe Gln Ala Thr Gln Ala Pro Arg Val Glu Lys Thr Pro Ser Leu
    370                375                380

Pro Asp Asp Leu Ser Asp Ser Thr Ser Leu Gly Thr Ser Val Ile Thr
385                390                395                400

Thr Cys Thr Ser Val Gln Glu Gln Gly Leu Lys Ala Asn Asn Ser Lys
                405                410                415

Glu Leu Ser Met Cys Phe Thr Glu Leu Thr Thr Asn Ile Ile Pro Gly
                420                425                430

Ser Asn Lys Val Ile Lys Pro Asn Ser Gly Pro Ser Arg Ala Arg Pro
                435                440                445

Ser Ala Ala Leu Thr Val Leu Ser Val Leu Met Leu Lys Gln Ala Leu
    450                455                460

<210> SEQ ID NO 10
<211> LENGTH: 1490
<212> TYPE: DNA
<213> ORGANISM: Homo sapiens

<400> SEQUENCE: 10
atgatcttgg caaacgcctt ctgcctcttc ttctttctag acgagaccct ccgctctttg      60 gccagcccctt cctccctgca gggccccgag ctccacggct ggcgccccccc agtggactgt    120 gtccgggcca atgagctgtg tgccgccgaa tccaactgca gctctcgcta ccgcactctg    180
cggcagtgcc tggcaggccg cgaccgcaac accatgctgg ccaacaagga gtgccaggcg    240
gccttggagg tcttgcagga gagcccgctg tacgactgcc gctgcaagcg gggcatgaag    300
aaggagctgc agtgtctgca gatctactgg agcatccacc tggggctgac cgagggtgag    360
gagttctacg aagcctcccc ctatgagccg gtgacctccc gcctctcgga catcttcagg    420
cttgcttcaa tcttctcagg gacaggggca gacccggtgg tcagcgccaa gagcaaccat    480
tgcctggatg ctgccaaggc ctgcaacctg aatgacaact gcaagaagct gcgctcctcc    540
tacatctcca tctgcaaccg cgagatctcg cccaccgagc gctgcaaccg ccgcaagtgc    600
cacaaggccc tgcgccagtt cttcgaccgg gtgcccagcg agtacaccta ccgcatgctc    660
ttctgctcct gccaagacca ggcgtgcgct gagcgccgcc ggcaaaccat cctgcccagc    720
tgctcctatg aggacaagga aagcccaac tgcctggacc tgcgtggcgt gtgccggact    780
gaccacctgt gtcggtcccg gctggccgac ttccatgcca attgtcgagc ctcctaccag    840
acggtcacca gctgccctgc ggacaattac caggcgtgtc tgggctctta tgctggcatg    900
attgggtttg acatgacacc taactatgtg gactccagcc ccactggcat cgtggtgtcc    960
ccctggtgca gctgtcgtgg cagcgggaac atggaggagg agtgtgagaa gttcctcagg    1020
gacttcaccg agaacccatg cctccggaac gccatccagg cctttggcaa cggcacggac    1080
gtgaacgtgt ccccaaaagg cccctcgttc aggccaccc aggcccctcg gtggagaag    1140 acgccttctt tgccagatga cctcagtgac agtaccagct ggggaccag tgtcatcacc    1200
```

```
acctgcacgt ctgtccagga gcaggggctg aaggccaaca actccaaaga gttaagcatg    1260
tgcttcacag agctcacgac aaatatcatc ccagggagta acaaggtgat caaacctaac    1320
tcaggcccca gcagagccag accgtcggct gccttgaccg tgctgtctgt cctgatgctg    1380
aaacaggcct tgtaggctgt gggaaccgag tcagaagatt tttgaaacta cgcagacaag    1440
aacagccgcc tgacgaaatg gaaacacaca cagacacaca cacaccttgc               1490
```

<210> SEQ ID NO 11
<211> LENGTH: 445
<212> TYPE: PRT
<213> ORGANISM: Rattus sp.

<400> SEQUENCE: 11

```
Met Ile Leu Ala Asn Ala Phe Cys Leu Phe Phe Leu Asp Glu Thr
 1               5                  10                  15

Leu Arg Ser Leu Ala Ser Pro Ser Ser Leu Gln Gly Ser Glu Leu His
                20                  25                  30

Gly Trp Arg Pro Gln Val Asp Cys Val Arg Ala Asn Glu Leu Cys Ala
            35                  40                  45

Ala Glu Ser Asn Cys Ser Ser Arg Tyr Arg Thr Leu Arg Gln Cys Leu
        50                  55                  60

Ala Gly Arg Asp Arg Asn Thr Met Leu Ala Asn Lys Glu Cys Gln Ala
 65                  70                  75                  80

Ala Leu Glu Val Leu Gln Glu Ser Pro Leu Tyr Asp Cys Arg Cys Lys
                85                  90                  95

Arg Gly Met Lys Lys Glu Leu Gln Cys Leu Gln Ile Tyr Trp Ser Ile
            100                 105                 110

His Leu Gly Leu Thr Glu Gly Glu Phe Tyr Glu Ala Ser Pro Tyr
        115                 120                 125

Glu Pro Val Thr Ser Arg Leu Ser Asp Ile Phe Arg Leu Ala Ser Ile
        130                 135                 140

Phe Ser Gly Thr Gly Thr Asp Pro Ala Val Ser Thr Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
        195                 200                 205

Asp Arg Val Pro Ser Glu Tyr Thr Tyr Arg Met Leu Phe Cys Ser Cys
    210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Ser
                245                 250                 255

Leu Cys Arg Thr Asp His Leu Cys Arg Ser Arg Leu Ala Asp Phe His
            260                 265                 270

Ala Asn Cys Arg Ala Ser Tyr Arg Thr Ile Thr Ser Cys Pro Ala Asp
        275                 280                 285

Asn Tyr Gln Ala Cys Leu Gly Ser Tyr Ala Gly Met Ile Gly Phe Asp
    290                 295                 300

Met Thr Pro Asn Tyr Val Asp Ser Asn Pro Thr Gly Ile Val Val Ser
305                 310                 315                 320
```

```
Pro Trp Cys Asn Cys Arg Gly Ser Gly Asn Met Glu Glu Cys Glu
                325                 330                 335

Lys Phe Leu Arg Asp Phe Thr Glu Asn Pro Cys Leu Arg Asn Ala Ile
                340                 345                 350

Gln Ala Phe Gly Asn Gly Thr Asp Val Asn Met Ser Pro Lys Gly Pro
            355                 360                 365

Ser Leu Pro Ala Thr Gln Ala Pro Arg Val Glu Lys Thr Pro Ser Leu
        370                 375                 380

Pro Asp Asp Leu Ser Asp Ser Thr Ser Leu Gly Thr Ser Val Ile Thr
385                 390                 395                 400

Thr Cys Thr Ser Ile Gln Glu Gln Gly Leu Lys Ala Asn Asn Ser Lys
                405                 410                 415

Glu Leu Ser Met Cys Phe Thr Glu Leu Thr Thr Asn Ile Ser Pro Gly
                420                 425                 430

Ser Lys Lys Val Ile Lys Leu Asn Ser Gly Ser Ser Leu
                435                 440                 445
```

ASSAYS USING GLIAL CELL LINE-DERIVED NEUROTROPHIC FACTOR RECEPTORS

The present application is a continuation-in-part of application Ser. No. 08/747,842, filed Nov. 13, 1996, now abondaned, which claims priority benefit of Provisional Application Ser. No. 60/006,619, filed Nov. 13, 1995; No. 60/015,767, filed Apr. 16, 1996; No. 60/021,965, filed Jun. 27, 1996; No. 60/020,638, filed Jun. 27, 1996; and No. 60/020,639, filed Jun. 27, 1996, all applications hereby incorporated by reference in their entireties.

FIELD OF THE INVENTION

The present invention relates to the identification of receptors for and functions of GDNF, and cell lines expressing the receptors.

BACKGROUND OF THE INVENTION

Glial cell line-derived neurotrophic factor (GDNF) is a trophic polypeptide. It is a disulfide bridge-linked homodimer of two 134-amino acids long glycosylated polypeptides, with a molecular weight of approximately 25–30 kD for each monomer. Prior to the molecular cloning of GDNF in 1993, investigators sought a trophic polypeptide which would alleviate the neuronal loss associated with Parkinson's disease, specifically dopaminergic neurons of the ventral mesencephalon. The survival of this subpopulation of neurons has been known for some time to be promoted by soluble factors present in the conditioned media of glial cell lines. It was from one of these cell lines that the GDNF protein was initially isolated based upon its ability to promote dopamine uptake in primary cultures prepared from embryonic ventral midbrain neurons (Lin et al., 260 Science 1120, 1993). Subsequently, GDNF was shown to promote survival of adult substantia nigra neurons in vivo following pharmacological treatments and lesions that mimic Parkinsonian syndromes (Beck et al., 377 *Nature* 339, 1995; Tomac et al., 373 *Nature* 335, 1995) Although GDNF was originally reported to be highly specific for dopaminergic neurons, several other potent activities of this molecule have subsequently been demonstrated, including survival and phenotypic responses in facial and spinal motor neurons (Henderson et al., 266 Science 30 1062, 1994; Oppenheim et al., 373 Nature 344, 1995; Yan et al., 373 Nature 341, 1995), noradrenergic neurons of the locus coeruleus (Arenas et al., Neuron, in press, 1995), cerebellar Purkinjie cells (Mount et al., 92 PNAS 9092, 1995), sympathetic and sensory neurons in peripheral ganglia (Trupp et al., 130 J. Cell Biol. 137, 1995) and for populations of peripheral neurons with target-derived and paracrine mode of action (Trapp, M. et. al., *J. Cell Biol.*, 130, 137–148 (1995); Pitchel, J., Sariola, H., Hoffer, B. & Westphal, H. (unpublished observation); Buj-Bello, A., Buchman, V. L., Horton, A., Rosenthal, A.& Davies, A. M. *Neuron*, 15, 821–828 (1995). As many of these neurons are affected in neurodegenerative diseases, GDNF may have potent therapeutical applications. Particularly, exogenously administered GDNF maintains dopaminergic neurons of the substantia nigra in experimentally induced Parkinsons disease in rodents (Beck et al. (1995) *Nature*, 373, 339–341; Tomac et al. (1995) Nature, 373, 335–339) and leads to functional recovery in Parkinsonian rhesus monkeys (Gash et al. (1996) *Nature*, 380, 252–255). GDNF treatment also rescues about half of the experimentally axotomized murine motoneurons (Oppenheim et al. (1995) *Nature*, 373, 344–346; Li et al. (1995) *Proc. Natl, Acad. Sci. U.S.A.*, 92, 9771–9775) suggesting that GDNF may be used in treatment of motoneuronal diseases. The studies of the mechanism of GDNF action in normal and pathogenic conditions have been, however, basically hampered as its receptor was not known.

Based upon structural similarities (primarily seven conserved cysteine amino acid residues), GDNF appears to be a distant member of the transforming growth factor-beta (TGF-13) superfamily of multifunctional cytokines, which includes TGF-βs, activins, bone-morphogenetic proteins (BMPs) and growth and differentiation factors (GDFS) (Roberts et al., 327 *Philos.Trans.R.Soc.Land.* 145,1990). TGF-β and related ligands are known to suppress proliferation in epithelial and immune cells, to function as morphogens in early development, to induce ectopic expression of skeletal tissue, and to promote survival and differentiation of neurons. TGF-β superfamily proteins interact with numerous receptor subunits on the surface of responsive cells (Attisano et al., 1222 *Mol. Cell Res.* 71, 1994; Derynck, 19 *Trends Biochem. Sci.* 548, 1994). Different receptor types have been described based on the molecular weights of affinity labeled complexes. Among these are the type I, type II and type III receptors, which represent binding proteins of 55 kD, 70 kD and 300 kD, respectively. Type III receptors are abundantly expressed transmembrane proteoglycans of approximately 300 kD with a short cytoplasmic tail, and are thought to function in recruitment of ligand to an oligomeric receptor complex (Lopez-Casillas et al., 67 Cell 785, 1991). Indeed, a type III receptor is required on some cell lines for TGF-β2 binding to the signaling receptors. Type I and type II receptors are transmembrane proteins with an intracellular serine-threonine kinase domain and can therefore transmit downstream signals upon ligand binding (Attisano et al., 75 Cell 671, 1993; Derynck, 1994 supra). Type II receptors are constitutively activated kinases which upon ligand binding recruit type I receptors to a signaling complex. In this complex, type I receptors are phosphorylated by type II receptors on a juxtamembrane domain rich in serine residues, this phosphorylation is thought to result in the activation of the ser-thr kinase activity of type I receptors and in downstream signaling (Wrana et al., 370 Nature 341, 1994). According to this model, TGF-β superfamily proteins can not bind to type I receptors in the absence of type II receptors, although in some cases, type I receptors are necessary for efficient binding to type II receptors (Letsou et al., 80 Cell 899, 1995). Multiple cDNA clones of type I, II and III receptors for TGF-βS, activins and BMPs have been isolated by either expression or homology cloning, including seven mammalian type I receptors, four type II receptors and one type III betaglycan receptor. Additional membrane proteins binding different members of this family include glycosylphosphatidyl inositol (GPS)-linked 150 kD and 180 kD proteins of unknown structure and function (MacKay and Danielpour, 266 *J. Biol. Chem.* 9907, 1991), and endoglin, a 180 kD disulphide linked dimer which binds TGF-β1 but not TGF-β2.

The isolation and characterization of GDNF receptors is a prerequisite for the understanding of the full range of biological actions of GDNF and the signaling events that take place upon GDNF binding to responsive cells. Until now, progress in this area has been hampered by the lack of cell lines responsive to GDNF, that is, cell lines comprising GDNF receptors.

SUMMARY OF THE INVENTION

Receptors for GDNF are disclosed herein, as are cell lines expressing the same. Methods for identifying and isolating these receptors are also disclosed.

In one aspect, the present invention relates to isolated receptors which bind GDNF.

In another aspect, the present invention relates a method for determining compounds or compositions which bind GDNF receptors.

In yet another aspect, the present invention relates to methods for identifying homologs of GDNF by screening for compounds or compositions which have similar biological effects, such as tyrosine phosphorylation, increase in c-fos mRNA, and increases in cell survival.

In still another aspect, the present invention relates to methods for identifying analogs of GDNF by screening for compounds or compositions which are antagonistic for the biological effects of GDNF, such as are listed above.

In a further aspect, the present invention relates to compounds having the sequence as set forth in SEQ ID NOS:2 and 9.

In yet a further aspect, the present invention relates to nucleic acids having the sequence as set forth in SEQ ID NOS:5 and 10.

BRIEF DESCRIPTION OF THE DRAWINGS

FIG. 9. GDNF increased the survival of RN46A cells. RN46A cells were differentiated in media ±0–50 ng/ml GDNF for 8 days. The data represent the means ± SEM of three independent experiments (1,500–3,000 cells counted per condition). ANOVA indicated that the GDNF had a significant effect on survival at all concentrations compared to media alone (overall ANOVA: df=6,203; F=1 1.39, p,0.001; unequal N LSD post hoc test, p.0.001).

FIGS. 13 a–c. c-ret mRNA expression in adult brain and in developing substantia nigra. (a) Ribonuclease protection analysis (RPA) of c-ret mRNA expression in different regions of the adult rat brain. (b) RPA of c-ret mRNA expression during development of the rat ventral mesencephalon (nigra), and of GDNF mRNA expression in the developing striatum. (c) mRNA expression is indicated in arbitrary units where 100 corresponds to the level of expression in the respective regions in newborn animals.

FIGS. 14 a–h. c-RET is expressed in GDNF-responsive substantia nigra dopaminergic neuron. (a) Dark field autoradiogram of c-ret mRNA expression analyzed by in situ hybridization in the adult substantia nigra. Scale bar, 40 μm. (b) Bright field autoradiogram showing substantia nigra neurons containing c-ret mRNA. Scale bar, 7.5 μm. (c) Immunohistochemical analysis of c-RET protein expression in the adult substantia nigra. Scale bar, 27 μm. (d) autoradiogram showing in situ hybridization for c-ret mRNA in the adult rat brain after a unilateral lesion with 6-OHDA. The injection of this toxic dopamine analogue in the medial forebrain bundle ensures that only cells which actively take up and retrogradely transport dopamine will be compromised. Note the disappearance of the labeling for c-ret mRNA in the lesioned substantia nigra (arrowhead) 1 day and 5 days following the lesion. (e)Immunohistochemical analysis of c-RET protein expression in the adult substantia nigra after lesion with 6-OHDA and grafting of mock transfected fibroblasts (control graft). Note the nearly complete absence of c-RET-LI caused by the lesion. Scale bar, 20 μm. (f) Grafting of GDNF-expressing fibroblasts rescues c-RET-LI. Note c-RET positive fibers surrounding and entering the GDNF producing graft (arrows). Same magnification as in (e). (g) Immunohistochemical analysis of cRET protein expression in the adult locus coeruleus after lesion with 6-OHDA and grafting of mock transfected fibroblasts (control graft). Scale bar, 23 μm. (h) Rescue of cell bodies expressing c-RET-LI by GDNF in of 6-OHDA lesioned locus coeruleus. Same magnification as in (g). Graft is on the right in (e) and (f), and above in (g) and (h).

FIGS. 19 a–h. GDNF binds in situ to c-ret-positive developing enteric neurons. (a, b) Dark-field (a) and corresponding bright-field (b) microphotographs of GDNF antisense cRNA hybridization to paraffin sections through E15 rat gut. (c, d) Dark-field (c) and corresponding bright-field (d) microphotograph of in situ binding of $^{125}$I-GDNF to E15 rat gut explants. (e) c-ret antisense cRNA hybridization to a cryosection through E15 rat gut. (f) Immunostaining of E15 rat gut cryosection with anti-peripherin antibodies. (g) GDNF sense cRNA hybridization to E15 rat gut section. (h) In situ binding of $^{125}$I-GDNF to E15 rat gut explants in the presence of 250-fold excess of unlabeled GDNF. - - - , muscle layer; n, intestinal nerve plexus. Bar, 100 μm.

FIGS. 20a–b. Crosslinked GDNF-c-RET-complexes are obtained from GDNF-responsive cell lines and from c-ret-transfected cells (a) $^{125}$I-GDNF was crosslinked with EDAC to PC12 cells, NB2/a cells, dissociated E20 rat kidney cells, and COS cells, and the resulting complexes were precipitated by anti-GDNF antibodies. (b) EDAC-crosslinked $^{125}$I-GDNF-c-RET complexes were immunoprecipitated with anti-c-RET antibodies from the extracts of PC12 cells, stably c-ret-transfected (Ret.-3T3) or mock-transfected (mock-3T3) 3T3 cells, as well as from dissociated E15 kidney cells in the presence (+) or absence (−) of 500-fold excess of unlabeled GDNF or TGF-β1. The ~50K bands in all gels are the crosslinked dimers of GDNF.

FIG. 24. Autoradiographic film of the ligand blot $^{125}$I-GDNF with proteins from adult rat brain (lane 2) and liver (lane 3). 50-fold excess of unlabeled GDNF (lane 1) significantly reduces the binding.

FIG. 25. Amino acid sequence of GDNFR-β (SEQ ID NO:2).

FIGS. 26 a–b. Comparison of amino acid sequences of a) rat GDNFR-α (SEQ ID NO:1) and GDNFR-β (SEQ ID NO:2) and b) rat GDNFR-α (SEQ ID NO:1), human GDNFR-α (SEQ ID NO:8), rat GDNFR-β (SEQ ID NO:2), and human GDNFR-β (SEQ ID NO:9).

FIGS. 31A–B. Effect of co-transfection of GDNFR-α and GDNFR-β with c-Ret in COS cells upon phosphorylation of c-RET (a) and effect of transfection of GDNFR-α and GDNFR-β in Neuro-2A cells upon phosphorylation of c-RET.

FIG. 32. The cDNA sequence for rat GDNFR-β (SEQ ID NO:5).

FIG. 33. (a) the cDNA sequence of human GDNFR-β (SEQ ID NO:10). The translation termination site and the sequences of the primers used to amplify the 5' end of the gene are marked in bold. The first and last 6 nucleotides of the sequence (nucleotides 469–1490) derived from I.M.A.G.E. EST clones are underlined.

DETAILED DESCRIPTION

Figure 1A:
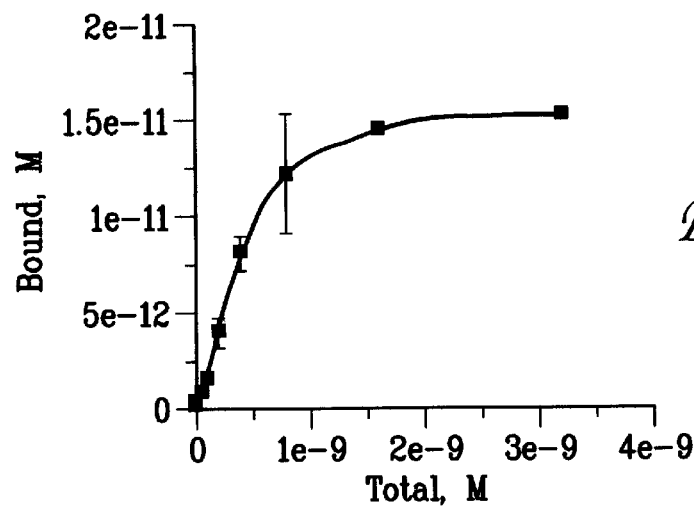
FIGS. 1A–C. Binding of $^{125}$I-GDNF to receptors on chick sympathetic neurons. (a) Saturation steady-state binding of $^{125}$I-GDNF to E10 embryonic chick sympathetic neurons. Data are expressed as mean ±SD of triplicate determinations. (b) Scatchard transformation of the data plotted in (a). (c) Hill transformation of the data plotted in (a) nH: Hill coefficient.

A prerequisite for the understanding of the full range and mechanisms of action of GDNF is the characterization of GDNF receptors and their signaling pathways. Although receptors for other members of the TGF-β superfamily are well characterized, GDNF receptors remained undefined until this disclosure. Disclosed herein is the biochemical characterization of GDNF receptors and their downstream responses in sympathetic neurons and responsive cell lines. Using affinity labeling, multiple GDNF binding subunits that mediate cooperative binding of GDNF to embryonic sympathetic neurons are identified. Screening of over thirty cell lines initially revealed high expression of GDNF binding proteins of 55 kD, 70 kD, 135 kD and 300 kD in conditionally immortalized neuronal precursors from the raphe nucleus. As the data demonstrate, GDNF receptors were highly induced after neuronal differentiation of these cells, which then became sensitive to the survival-promoting effects of GDNF. Different combinations of these subunits were also seen in glioma, myoblast and Sertoli cells. A different receptor pattern was found in a motor neuron hybrid cell line, where the predominant component was a GPI-anchored protein of 155 kD.

Despite the striking similarity with the receptor pattern of other TGF-β superfamily members, immunoprecipitation experiments indicated that GDNF receptor subunits of 55 kD, 70 kD, 135 kD, and 300 kD are novel proteins. The 55 kD binding protein has been confirmed to be GDNFR-α described as being cloned from the substantia nigra (Treanor et al. *Nature*, 382:80–83, 1995) and from the retina (Jing et al. *Cell,* 85:1113–1124,1996). GDNFR-α is attached to the cell membrane by a glycosylphosphatidyl inositol linkage (GPI) and, thus, cannot transmit intracellular signals on its own. The 70 kD binding protein has now been cloned and sequenced from the rat and human and has been designated as "GDNFR-β."

We assign the locus of GDNFR-β to human chromosomes 8p21–22 and mouse chromosome 14D3-E1. The 155 kD subunit was subsequently determined to be the product of the c-ret proto-oncogene, c-RET, a receptor tyrosine kinase crucial for the development of parts of the excretory and nervous systems. GDNF stimulated ERK tyrosine phosphorylation and c-fos mRNA expression with different time-courses in raphe nucleus and motor neuron cell lines, suggesting that different complements of GDNF receptor subunits can form distinct signaling complexes.

Concomitantly, c-RET was identified as receptor for GDNF on additional cell lines. GDNF rescues c-RET-positive dopaminergic and noradrenergic neurons in lesion models of Parkinson's disease, suggesting that cRET may mediate the anti-Parkinsonian effects of GDNF in the adult brain.

c-ret proto-oncogene (Takahashi et al. (1985) *Cell,* 42, 581–588) encodes a protein that is structurally related to receptor tyrosine kinases (Takahashi et al. (1988) *Oncogene,* 3,571–578). Its extracellular part contains an unusual cadherin-like domain and also a cysteine-rich domain, the biological roles for which are not understood. By alternative splicing, several isoforms of c-ret mRNA have been described (Tahira et al. (1990) *Oncogene,* 5, 97–102; Myers et al., (1995) *Oncogene,* 11, 2039–2045; Lorenzo et al. (1995) *Oncogene,* 10, 1377–1383), but their biological meaning is currently not understood. In several cell lines, c-ret-encoded proteins with molecular weights of 160 kD and 140 kD are described, representing the fully and partially glycosylated isoforms of 120 kD core protein, respectively (Takahashi et al., 1988). As with other receptor tyrosine kinases, c-RET is activated by homodimerization followed by phosphorylation of its tyrosine residues.

In the excretory system, c-ret is expressed in the nephric duct, the ureteric bud and the growing tips of the collecting ducts (Pachnis et al., (1993), supra). Mice homozygous for a null mutation in the c-ret gene die soon after birth, with kidneys either absent or rudimentary and displaying severe defects in the enteric nervous system (Schuchardt et al., *Nature* 367, 380–3 (1994). Based on this evidence, it had been proposed that the cognate c-ret ligand may be a growth factor important for morphogenesis and neurogenesis.

During murine embryogenesis, c-ret mRNA is expressed primarily in the nervous and excretory systems. c-ret mRNA is found in dorsal root, sympathetic, enteric and cranial ganglia (Pachnis et al., *Development* 119, 1005–17 (1993), as well as in post migratory neural crest cells and in various tumors of neural crest origin, including pheochromocytoma, medullary thyroid carcinoma and neuroblastoma (Ikeda, I., el al. *Oncogene* 5, 1291–6 (1990); Santoro, M., et al. *Oncogene* 5, 1595–1598 (1990). In the developing central nervous system, sites of c-ret expression include the ventral portion of the neural tube, the retina and motor neurons in spinal cord and hindbrain (Pachnis et al., (1993), supra). However, the pattern of expression of c-ret in the adult nervous system has not previously been reported.

The absence of a known ligand for c-RET has basically hampered the studies of intracellular pathways that c-RET can mediate. Comparative analysis of the growth-promoting activity of the epidermal growth factor receptor/c-RET chimera expressed in fibroblastic or hematopoietic cells revealed a biological phenotype clearly distinguishable from that of epidermal growth factor receptor (Santoro et al. (1994) *Mol. Cell. Biol.* 14, 663–675). We disclose herein that both NGF and GDNF promote survival of PC12 cells, whereas only NGF induces their differentiation, suggesting only a partial overlap in the signaling pathways of c-RET and trka, a receptor for NGF. Binding of an adaptor protein Grb2 to oncogenic forms of c-RET has been demonstrated (Borrello et al. (1994) *Oncogene*, 9, 1661–1668). However, the details of the pathways are completely unknown. Now, having GDNF as a ligand, it is possible to address the intracellular signaling of c-RET upon GDNF binding.

Like c-RET, GDNF is abundantly expressed in the muscle layer of the gastrointestinal tract and in the condensing mesenchyme of the kidney (Suvanto et al. (1996) *Eur. J. Neurosci.*, 8, 816–822). Further, as disclosed herein, GDNF specifically binds c-RET-positive cells in developing gut, GDNF can be cross linked to c-RET in several cell lines and in developing kidney, GDNF specifically induces tyrosine phosphorylation of c-RET, and ectopical expression of c-RET in 3T3 cells confers a biological response of these cells to GDNF. Thus, c-RET is activated by GDNF and mediates its functions.

As disclosed further herein, GDNFR-α and GDNFR-β mediate GDNF-induced c-RET autophosphorylation in transfected cells. The presence of the similarly behaving GDNF presenting proteins may lower the amount of GDNF needed to activate c-RET. By Northern hybridization, we disclose that the transcript level of human GDNFR-β mRNA is high in the adult brain, intestine and placenta and in fetal brain, lung and kidney. Studied by in situ hybridization, GDNFR-β mRNA shows in E17 rat embryo different distribution than that of GDNFR-α mRNA, especially in adrenal gland, kidney and gut. In the developing nervous system, GDNFR-β mRNA expression is restricted to certain neuronal populations, while GDNFR-α mRNA is widely expressed also in non-neuronal cells. The distinct tissue distribution of GDNFR-β mRNA and its ability to mediate GDNF signal in transfected cells suggest a role in signal transduction of GDNF and, possibly, related neurotrophic factors in vivo. The fact that GDNFR-β mRNA is present in some organs (such as adrenal cortex) where GDNF is not available points out to a possibility that some other ligand (like GDNF homolog such as neurturin and persefin; Kotzbauer et al., *Nature*, 384:467–470, 1996 and Kotzbauer et al., *Differentiation and Degeneration, Keystone Symposia on Molecular and Cellular Biology*, Taos, N.Mex., Mar. 27–Apr. 2, 1996, p. 136, respectively) may use GDNFRβ in their signal transduction. Likewise GDNFR-β may also be used in the activation of other signaling receptors than Ret.

GDNF and the genes responsible for its signal transduction are of great clinical interest due to their potential use in therapy for motoneuron and Parkinson's diseases. In addition, these genes are intensively studied as possible candidate disease genes for congenital or inherited disorders affecting the survival of the neurons in substantia nigra and in the gastrointestinal tract.

The product of the c-ret proto-oncogene plays important roles in human disease. Rearrangements and mutations in the c-ret gene are associated with several tumors e.g. familial medullary thyroid carcinoma, multiple endocrine neoplasia type 2, etc., but also with Hirschsprung disease, a disorder that is characterized by the absence of enteric neurons in the hindgut, resulting in obstipation and megacolon in infants and adults (reviewed in Mak, Y. F. and Ponder, B. A. J. (1996) *Curr. Op. Genet. Dev.*, 6, 82–86). Identification of GDNF as a ligand for c-RET further enables the analysis of the molecular basis of these diseases. Particularly, the mutations in GDNF gene can now be studied as possible cause for the Hirschsprung disease in the cases where c-ret locus is not mutated.

At present, there is no candidate disease assigned to the human locus of GDNFR-β gene i.e., 8p21–22, but since it probably participates in the signal transduction of GDNF in neurons, the new receptor GDNFR-β is likely to be of great interest in investigations concerning neurodegenerative diseases. In addition, the gene for GDNF-β is a potent candidate disease gene for congenital disorders that resemble the phenotypes of GDNF or RET Knock-out mice (e.g. Hirschsprung disease, kidney aplasia and dysplasis), and we are screening for mutations in these developmental orders.

The phrases "GDNF receptor" and "receptor for GDNF" as used herein each refer to a single subunit which binds GDNF as well as combinations of the receptor subunits which bind GDNF.

The term "effect" as used herein means an alteration or change. An effect can be positive, such as causing an increase in some material, or negative, e.g., antagonistic or inhibiting.

The term "homolog" as used herein refers to a compound or composition having a similar biological effects as GDNF, such as are disclosed herein.

The term "analog" as used herein refers to a compound or composition having an antagonistic effect on the biological effects of GDNF.

The term "isolated" as used herein in reference to a GDNF receptor means a compound which has been separated from its native environment or, if recombinantly expressed, from its expression environment.

The phrase "substantially pure" as used herein in reference to a compound means an isolated compound which has been separated from other components which naturally accompany it. Typically, a compound is substantially pure when it is at least 75%, more preferably at least 90%, and most preferably 99% of the total material as measured, for example, by volume, by wet or dry weight, or by mole percent or mole fraction.

The phrase "non-permissive culture conditions" as used herein refers to conditions which do not normally support survival of the cells being cultured in vitro, e.g., temperature, media components, etc.

The phrase "an excess" as used in reference to the addition of labeled GDNF in a competitive assay refers to an amount of labeled GDNFsufficient to facilitate the detection of a competing compound—for example, an amount of labeled GDNF which is twice the amount of the compound to be tested.

The term "bind" as used herein refers to the interaction between the GDNF ligand and its receptor, the binding being of a sufficient strength and for a sufficient time to allow the detection of said binding under the conditions of the assays disclosed herein.

The term "about" in reference to a numerical value means ±10% of the numerical value, more preferably ±5%, most preferably ±2% .

Any claims to sequences herein encompass those insubstantial alterations which can be made to a sequence without effecting function, i.e., substantially the same sequences. For example, a change in a nucleotide within a codon that results in the same amino acid as originally encoded by the codon is "substantially the same sequence." Also, a conservative amino acid substitution within the sequence that does not affect function is also "substantially the same sequence."

The specific examples presented below demonstrate that:
1) GDNF receptor is present in multiple neuronal and non-neuronal cell types;
2) GDNF receptor is composed of multiple subunits which cooperate to achieve high affinity binding;
3) members of the ERK/MAP kinase family are components of the GDNF signaling mechanism; and
4) c-RET is a functional receptor for GDNF.

1. Novel GDNF Receptor Expression in Multiple Neuronal and Non-neuronal Cell Types Heretofore unidentified receptors are identified herein as GDNF receptors. These novel GDNF receptors were found in cells lines of different origins, although they appeared to be most abundant in neuronal cells. Preferably, the cell lines are selected from the group consisting of RN33B, RN46A, and C6 (see Table I), with RN33B being most preferred. The identification of GDNF receptors in many of these cell types suggests novel cellular populations responsive to GDNF in vivo. GDNF has been shown to promote survival and phenotype of distinct subpopulations of neurons, in particular dopaminergic and noradrenergic central neurons, as well as spinal and facial motor neurons. Given the activities of GDNF in various monoaminergic neurons, the discovery of GDNF receptors in cell lines derived from the medullary raphe indicate that serotonergic neurons may also respond to GDNF in vivo. The endogenous expression of GDNF by these cells suggests that this factor may act in a paracrine/autocrine fashion within the raphe nucleus. Expression of GDNF receptors in Sertoli TM4 cells suggests non-neuronal roles for GDNF in developing testis. In vivo, the temporal expression of GDNF mRNA in testis correlates with the expansion of the Sertoli cell population (Trupp et al., supra) which, together with the discovery of GDNF receptors on the TM4 cell line, suggest an autocrine action of GDNF during Sertoli cell maturation. Similarly, the presence of GDNF receptors in rat myoblast L6 cells, together with the expression of in developing muscle in vivo (Henderson et al., supra; Trupp et al., supra), indicates a potential paracrine role of GDNF during myogenesis. Despite the presence of receptors and biological activities of GDNF on embryonic sympathetic neurons, PC12 cells which had been differentiated into sympathetic-like neurons with NGF did not express GDNF receptors under initial experimental conditions. As discussed below, however, GDNF receptors were ultimately identified on PC12 cells.

GDNF receptors are absent in the pons noradrenergic cell line CATH.a. Given the robust effects of GDNF on adult central noradrenergic neurons from the locus coeruleus, the absence of GDNF receptors in CATH.a is intriguing. Recently, however, Gong et al. reported that GDNF can prevent the degeneration of CATH.a cells induced by 6-OH-dopamine treatment (Gong et al., 21 Abs. Soc. Neurosci., 1789, 1995), suggesting that GDNF receptors may be induced in these cells after 6-OH-dopamine lesion. Indeed, in vivo studies have shown that GDNF elicits a more profound induction of the phenotype of noradrenergic neurons following 6-OH-dopamine injection than in the non-lesioned locus coeruleus. Further, Treanor et al. recently reported upregulation of GDNF binding in sections of the substantia nigra after medical forebrain bundle transaction (Treanor et al., 21 Abs. Soc. Neurosci. 1301, 1995), suggesting that the receptor upregulation may be a general mechanism of control of GDNF responsiveness in the central nervous system.

GDNF receptor upregulation was also observed during in vitro differentiation of raphe nucleus cells. These lines have recently been shown to retain the ability to respond to local microenvironmental signals after transplantation into the adult brain, where they differentiate in a direction that is consistent with that of endogenous neurons in the transplantation site (Shihabuddin et al., 15 J. Neurosci. 6666, 1995). In vitro, however, a shift to the non-permissive temperature differentiates them along default pathways into glutamatergic (RN33B) or serotonergic (RN46A) phenotypes, respectively. Differentiation in culture has also been shown to upregulate expression of receptors for other trophic factors in these cells, including the neurotrophin receptors $p75^{LNGFR}$ and trkB (Whittemore and White, 615 British Res. 27, 1993). Although they can give rise to different neuronal types depending upon the site of transplantation, RN33B cells are not able to generate glial elements, suggesting these cells represent neuronally restricted multipotent precursors (Shihabuddin et al., supra). In this respect, it is interesting to note the absence of GDNF receptors in two pluripotent neuronal stem cell types (Renfranz et al., 66 Cell 713, 1991; Snyder et al., 30 68 Cell 33, 1992) suggesting that these cells are less restricted than the raphe nucleus cell lines. Taken together, these observations suggest that GDNF receptor expression may initially appear in newly differentiated post-mitotic neurons and increase progressively during neuronal maturation.

2. Multiple GDNFR Receptor Subunits

The data demonstrate that novel GDNF receptor is composed of multiple subunits which cooperate to achieve high affinity binding. The cooperative binding of GDNF to embryonic sympathetic neurons may thus be an indication of a multi-step mechanism of receptor assembly. Because binding assays were performed at 4° C., binding cooperativity is unlikely to have resulted from substantial lateral mobility of transmembrane receptor proteins, suggesting that GDNF binding induces conformational changes on receptor complexes that are partially preformed on the membrane. The nearly identical affinities of the different GDNF receptor subunits obtained by cross linking also support the notion of cooperative binding of GDNF to a partially pre-assembled receptor complex.

The structural similarities between GDNF and members of the TGF-β superfamily suggest that receptors for GDNF might conform to some of the prototypes described for receptors of members of the TGF-β family. Indeed, the pattern of GDNF binding proteins described herein is strongly reminiscent of type I, type II and type III TGF-β receptors.

Despite the overall similarities between GDNF and TGF-β superfamily receptors, no GDNF receptors could be detected in several cell lines known to express various TGF-β and activin receptor subunits, including the mink lung epithelial cell line MvlLu. In agreement with this observation, no binding of GDNF has been detected in COS cells transfected with different combinations of known type I and type II TGF-β superfamily receptors (Ibanez, C., unpublished; P. ten Dijke, personal communication), including the recently isolated type II receptor for BMPs (Rosenzweig et al., 92 PNAS USA 7632, 1995) and a novel brain-specific type I receptor (Ryden et al., 21 Abs. Soc. Neurosci 1754, 1995). Moreover, no GDNF receptor complexes could be recovered after immunoprecipitation with antipeptide antisera against any of the cloned TGF-β superfamily receptors, indicating that GDNF receptor components are novel proteins.

3. c-RET is a Receptor for GDNF

GDNF receptors were found in a motor neuron-neuroblastoma hybrid cell line, but not in a basal forebrain cell which was also a hybrid with the same neuroblastoma, suggesting that the receptors detected on MN–1 cells represent physiologically relevant motor neuron GDNF receptors. In contrast to raphe nucleus cells, GDNF expression could not be detected in the motor neuron cell line, consistent with a target-derived mode of action for muscle-derived GDNF in vivo (Henderson et al., 266 Science 1062, 1994; Trupp et al., supra). GDNF binds to and induces tyrosine phosphorylation of the these receptor which were identified as the product of c-ret. c-ret was also able to mediate GDNF binding and survival/growth responses to GDNF upon transfection into naive fibroblasts. Moreover, dopaminergic neurons of the adult substantia nigra were found to express high levels of c-ret mRNA, and c-RET expressing dopaminergic and noradrenergic neurons in the CNS responded to the protective effects of exogenous GDNF in vivo. Together, these data indicate that the product of the c-ret proto-oncogene encodes a functional receptor for GDNF which may mediate the neurotrophic effects of this factor on dopaminergic, noradrenergic and motor neurons.

The results disclosed herein indicate that the c-RET receptor tyrosine kinase is a signal transducing receptor for GDNF. This finding is surprising, given that all receptors for members of the TGF-β superfamily characterized so far are receptor serine-threonine kinases (Derynck, R. *Trends Biochem Sci* 19, 548–553 (1994); Attisano et al., *J.Bba-Mol Cell Res*, 222, 71–80 (1994)). GDNF is in fact a very divergent member of the TGF-β superfamily, with which it shares primarily the spacing between conserved cysteine residues in the amino acid sequencer. Its ability to interact with a receptor tyrosine kinase indicates a further functional divergence from other members of the TGF-β superfamily. Conversely, these findings could suggest that other TGF-β superfamily members may also utilize receptor tyrosine kinases.

The following results disclosed herein also implicate the c-ret proto-oncogene product as a functional receptor for GDNF:

i) GDNF binds to COS cells ectopically expressing the c-ret proto-oncogene;

ii) GDNF can be chemically crosslinked to the product of the c-ret proto-oncogene ectopically expressed in COS cells or from NB2/a and PC12 cells;

iii) the c-ret proto-oncogene product ectopically expressed in COS cells, but also in NB2/a cells, becomes rapidly phosphorylated on tyrosine residues upon GDNF binding;

iv) GDNF promotes biological effects i.e. mitogenic or trophic in cells expressing c-ret proto-oncogenic products.

GDNF specifically binds to RET-expressing (FIGS. 19 *c, d, h*) enteric neurons and the tips of ureteric buds in developing kidney. These tissues were absent or severely reduced in c-ret-deficient mice (Schuchardt et al. (1994) *Nature*, 367,380–383; Durbec et al. (1996) *Development*, 122, 349–358). The data disclosed herein further demonstrate GDNF-c-RET complexes from GDNF-responsive and c-ret-transfected cells and from embryonic kidney cells. Finally, GDNF time and dose-dependently activates c-RET, and introduction of c-ret into GDNF-nonresponsive cells results in GDNF-responsiveness.

4. Downstream Signaling Pathways Activated by GDNF Receptor

Investigation of GDNF signal transducing mechanisms in raphe nucleus and motor neuron cell lines has been conducted. The downstream responses elicited by GDNF in these cells demonstrate that the GDNF binding proteins identified herein represent functional GDNF receptors. The initial biochemical characterization of GDNF signal transduction pathways has identified members of the ERK/MAP kinase family as components of the GDNF signaling mechanism. ERK/MAP kinase activation by phosphorylation is the final step in a cascade of kinases that is set in motion after activation of the Ras pathway by various growth factors, including TGF-β (Yan et al., 269 *J. Biol. Chem.* 13231, 1994; Hartsough and Mulder, 270 *J. Biol. Chem.* 7117, 1995) and nerve growth factor (Thomas et al., 68 Cell 1031, 1992; Wood et al., 68 *Cell* 10 II, 1992). More recently, ERK2 has also been shown to form part of the signal transduction pathway activated by several cytokines, such as interferons and interleukins, which are not known to activate Ras (David et al., 269 *Science* 1721, 1995). Whether or not Ras activation is one of the steps in the signaling transduction mechanism of GDNF is an area of further interest.

Interesting differences were found between the patterns of ERK phosphorylation induced by GDNF in raphe nucleus RN33B cells and in motor neuron MN–1 cells. GDNF treatment stimulated very rapid (maximum at 5 min) and transient (undetectable after 60 min) tyrosine phosphorylation of ERKI and ERK2 in RN33B cells, but relatively slower (maximum at 15 min) and more sustained (still detectable after 120 min) phosphorylation of ERK2, but not ERKI, in MN–1 cells. That these differences may have functional significance is suggested by recent observations made in PC12 cells treated with different growth factors. Exposure of PC12 cells to NGF or fibroblast growth factor (FGF) results in neuronal differentiation and in sustained elevation of Ras activity and ERK tyrosine phosphorylation (Qiu and Green, 7 *Neuron* 977, 1991). In contrast, treatment with epidermal growth factor, which stimulates DNA synthesis and proliferation of PC12 cells, results in only transient (<1 hr) activation of Ras and ERKs (Qiu and Green, 1991). Thus, different time-courses of ERK activation underlie different biological responses in PC12 cells. Taken together, the different patterns of GDNF receptors and GDNF-induced ERK phosphorylation in RN33B and MN–1 cells suggest that different GDNF receptor subunits can cooperate to assemble distinct signaling complexes in different cell types. Whether different GDNF signal transduction pathways underlie the different biological effects of GDNF is an area of further interest.

Upon activation, ERKs translocate to the nucleus where they phosphorylate and thereby regulate the activity of transcription factors which, in turn, control gene expression. Phosphorylation of $p67^{SRF}$ and $p62^{TCF}$ transcription factors recruits them to the serum response element (SRE) in the c-fos gene promoter and stimulates c-fos gene transcription (Gille et al., 358 Nature 414, 1992). Transcription of c-fos is rapidly and transiently induced after various stimuli, including exposure of PC12 cells to NGF (Millbrandt, 83 *PNAS USA* 4789, 1986) and of osteoblastic cells to TGF-β (Machwate et al., 9 *Mol.Endocrin.* 187, 1995).

c-fos forms part of the AP-1 transcription factor complex, which is thought to be involved in the regulation of multiple genes, including growth factor, neuropeptide and neurotransmitter synthesizing enzyme genes (Gizang-Ginsberg and Ziff, 4 *Genes Dev.* 477, 1990); Hengerer et al., 87 *PNAS USA* 3899, 1990; Jalava and Mai, 9 *Oncogene* 2369, 1994).

The stimulation of c-fos transcription by GDNF indicates a role for AP-1 complexes in GDNF-induced gene expression. Thus, c-fos could mediate the increase in the tyrosine hydroxylase (TH) expression observed upon GDNF treatment of central noradrenergic neurons, or the GDNF-induced upregulation of vasoactive intestinal peptide (VIP) and preprotachykinin-A (PPTA) mRNAs in cultured sympathetic neurons from the superior cervical ganglion (Trupp et al., 13 *J. Cell Biol.* 137, 1995).

The effects of GDNF on the survival of differentiated serotonergic raphe nucleus cells indicate that the GDNF receptors identified on these cells are able to elicit relevant biological responses. The fact that cessation of proliferation, differentiation, and GDNF responsiveness were concomitant with increased GDNF receptor expression in these cells, suggests that GDNF may be a survival factor for developing serotonergic raphe neurons in vivo. The data of this patent disclosure suggest a role for ERKs and c-fos in GDNF-mediated neuron survival. This can be directly established using dominant negatives or antisense oligonucleotides.

The GDNF receptor subunits and complexes disclosed herein have wide-range applicability. The identification and isolation of GDNF receptor facilitates rational drug design for drugs useful in treating, for example, neuronal disorders, particularly those involving neuronal cell death. As was discussed previously, GDNF has been shown to promote survival of adult substantia nigra neurons in vivo following pharmacological treatments and lesions that mimic Parkinsonian syndromes, as well as survival responses in other neuronal cell lines. The drugs can be tested for binding affinity to GDNF receptor, and for their influence on the downstream effect of GDNF disclosed below—i.e., the phosphorylation of ERK2 and ERKI. As GDNF receptor has also been identified on malignant cell lines, design of drugs for use in cancer therapy is also evident. Further, considering structural similarity with BMP, the development of drugs to be used in treating bone-related diseases, i.e., osteoporosis, and for promoting the healing of fractures is also contemplated.

Accordingly, isolated receptors according to the present invention can be used, inter alia, to screen for compounds or compositions which are analogs and homologs of GDNF. The potential analogs and homologs can be screened initially in competitive binding assays employing either isolated receptor or cell lines expressing the receptor—i.e., NB2/a cells—and $^{125}$I-labeled GDNF. Methods such as those disclosed in Example 13 can be used. Analog or homolog activity can then be ascertained by further identifying those compounds or compositions which, for example, effect a decrease or increase, respectively, in the tyrosine phosphorylation of the RET proto-oncogene. Methods such as those disclosed in Example 17 can be used. Alternatively, GDNF can be used to screen for and identify other receptors using the above-reference procedures, or variations thereof.

The isolation of GDNF receptor also facilitates the development of antibodies, both polyclonal and monoclonal, against the receptor. These antibodies can be used to purify the receptors themselves, identify other cells expressing GDNF receptor, thereby prompting other therapeutic applications, identify other Type I-interactive receptors, as well as be used as drugs themselves. The antibodies can initially be produced using the ligand/receptor complexes disclosed herein as the immunogens. Antibodies specific for the ligand can be eliminated from the polyclonal serum by absorption with the ligand. Hybridomas for monoclonal production can be selected on the basis of binding of ligand, with the expansion of only those clones which do not bind the ligand uncomplexed with the receptor. The antibodies can be prepared by methods well known to those skilled in the art.

Alternatively, monoclonal and polyclonal antibodies against GDNF receptor and GDNF proteins can be used for the characterization and/or isolation of GDNF receptor molecular clones. Further, anti-GDNF antibodies can potentially be used in a screen for homologs, or in the production of anti-idiotype antibodies which mimic GDNF.

The isolation of GDNF receptor also facilitates the isolation and/or production of nucleic acids for the expression of recombinant GDNF receptor, both in vitro and in vivo, for diagnostic and therapeutic applications. The term "nucleic acids" as used herein includes, for example, genomic DNA, mRNA, and cDNA. Upon sequencing at least a portion of the GDNF receptor, oligonucleotide primers for isolating genomic DNA for GDNF receptor and receptor mRNA can be developed.

cDNA can be prepared from isolated mRNA. The isolation and production of nucleic acids can be accomplished utilizing methods well known to those skilled in the art using standard molecular biology techniques such as are set forth in Maniatis et al., *Molecular Cloning: A Laboratory* Manual, Cold Spring Harbor Laboratory, Cold Spring Harbor, N.Y., 1982, incorporated herein by reference. Recombinantly produced receptors can be used in crystallography studies for rational drug design. Recombinant extracellular domain can be produced and used as a drug in ligand sink applications, e.g., for ligands with antagonistic properties.

The nucleic acids as set forth above can be utilized for gene therapy, using both in vivo and ex vivo techniques. The nucleic acids can also be used to clone other related receptors using, for example, low stringency screens and reversed transcriptase PCR; and to produce cells overexpressing the receptors to screen for other ligands, e.g., by panning, and other materials serving as receptor agonists, antagonists, or partial agonists and antagonists. Alternatively, recombinantly produced receptor itself can be used for the screening assays. Additionally, cells expressing chimeric receptors can be produced using other TGF-β receptor family members to elucidate signal pathways. Intracellular targets of GDNF receptor can be identified using, for example, the yeast two-hybrid system. (Chen, et al., 377 *Nature* 548, 1995, incorporated herein by reference.)

The nucleic acids set forth above can also be used to develop transgenic and/or gene targeted animals. For example, transgenic animals can be developed for testing the effects of the overexpression of GDNF receptor. Procedures can be utilized such as are described in Hogan et al., *Manipulating the Mouse Embryo: A Laboratory Manual*, Cold Spring Harbor Laboratory, Cold Spring Harbor, N.Y., 1986, and Capecchi, M. R., *Trends Genet*, 5: 70–76, 1989, both incorporated herein by reference.

Alternatively, cell lines and transgenic animals unable to express GDNFreceptor can be prepared to ascertain the effects of blocking signaling by GDNF. Procedures such as are set forth in Wurst et al., *Gene Targeting Vol.* 126, edited by A. L. Joyner, IRL Press, Oxford University Press, Oxford, England, pp. 33–61, 1993, incorporated herein by reference, can be utilized.

Other applications and modifications are within the spirit and scope of the invention as herein disclosed and will be readily apparent to those skilled in the art.

EXAMPLES

The following Examples are provided for purposes of elucidation and not limitation on the disclosure or claims.

Unless otherwise indicated, binding and biochemical studies were carried out with recombinant rat GDNF produced in Sf21 insect cells using a baculovirus expression system. The protein was produced and purified as previously described (Trupp et al., supra, incorporated herein by reference). GDNF protein was quantified after silver staining of SDS/PAGE gels using standard curves obtained with commercial samples of proteins of molecular weight similar to that of GDNF. Purified human TGF-β1 was generously provided by Jun-ichi Koumegawa, Kirin Brewery, Tokyo, Japan. Proteins were labeled with Na-$^{125}$I by the chloramine-T method to a specific activity of approximately $1\times10^8$ cpm/μg.

Unless otherwise indicated, binding assays were performed as follows. Cells were incubated with iodinated GDNF in Dulbecco's phosphate buffered saline and 2 mg/ml bovine serum albumin (BSA) on Millipore Hydrophilic Durapore 96-well filtration plates. Following two hours of vigorous shaking at 4° C., the cells were washed twice with ice-cold binding buffer under vacuum. Dried filters were liberated and bound $^{125}$I-GDNF quantified in a gamma counter. Non-specific binding was determined by addition of 500-fold excess of cold ligand to the binding mixtures.

For affinity labeling, iodinated proteins were bound to monolayer cultures of primary neurons or cell lines. Prior to binding, dissociated chick sympathetic neurons were cultured for 48 hours in the presence of NGF on polyornithine/laminin coated dishes. Plated cells were incubated with 10 ng/ml $^{125}$I-GDNF at 4° C. in binding buffer as described above. Ligand/receptor complexes were chemically cross-linked for thirty minutes at room temperature using either disuccinimidyl suberate (DSS) or 1-Ethyl-3(-3-dimethylaminopropyl)-carbodiimide hydrochloride (EDAC) (Pierce Chemical, Rockland, Ill.). Following quenching of the cross-linking reactions, cells were washed twice with 10 mM Tris/HCl buffered saline, 2 mM EDTA, 10% glycerol, 1% NP-40, 1% Triton x-100, 10 μg/ml leupeptin, 10 μg/ml antipain, 50 μg/ml aprotinin, 100 μg/ml benzamidine hydrochloride, 10 μg/ml pepstatin and 1 mM PMSF (proteinase inhibitors from Sigma). Cleared lysates were boiled for 5 min in SDS/β-mercaptoethanol buffer, fractionated by SDS/PAGE on 4–20% gradient electrophoresis gels, and visualized by autoradiography. Molecular weights indicated were obtained by subtracting the weight of a GDNF ligand monomer, e.g., 25–30 kD, more preferably 23 kD, from the estimated molecular weights of cross-linked complexes visualized by SDS/PAGE. For affinity measurements of cross-linked complexes, cells were incubated on plates as above in the presence of increasing amounts of unlabeled GDNF. These samples were fractionated by gradient SDS/PAGE, gels were then dried and specific bands excised according to molecular weights determined from autoradiograms, and count in a gamma counter. For immunoprecipitation of affinity labeled receptor complexes, after binding and cross-linking with iodinated ligands, cell lysates were cleared and incubated overnight at 4° C. with 5–10 μl of antipeptide rabbit antisera against difference type I, II and III TGF-β superfamily receptors (ten Dijke et al., 264 Science 101, 1994) (provided by Peter ten Dijke, Ludwig Institute for Cancer Research, Uppsala, Sweden). Immunocomplexes were collected with Protein A-Sepharose (Pharmacia, Sweden), washed in lysis buffer and boiled for 5 minutes before SDS/PAGE and autoradiography as above.

Example 1

GDNF Receptors on Embryonic Sympathetic Neurons

Figure 1B:
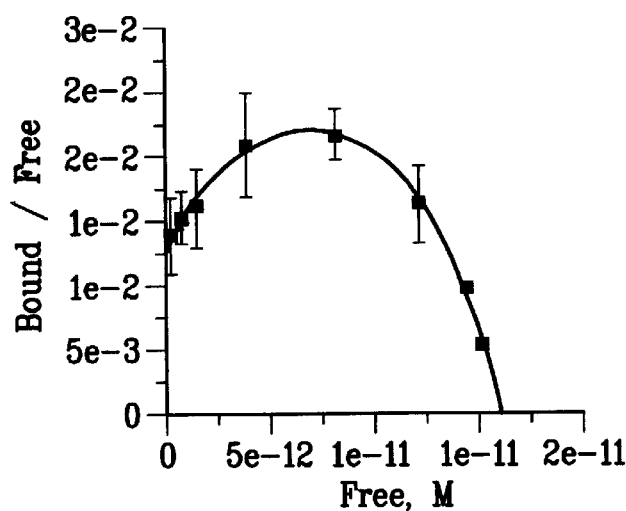
Figure 1C:
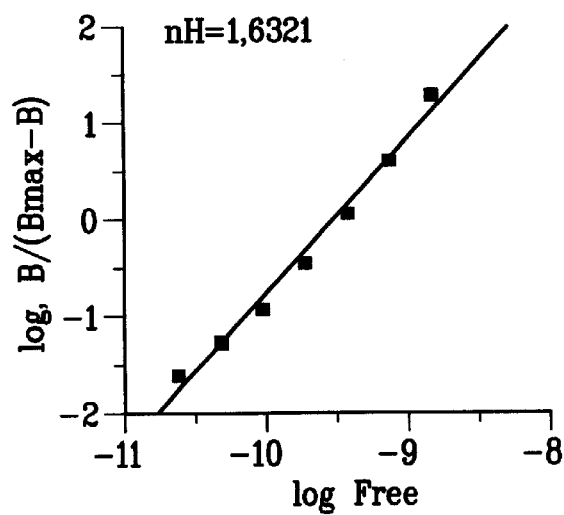

GDNF promotes survival of cultured embryonic chicken sympathetic neurons with similar efficacy and dose response curve as nerve growth factor (NGF) (Trupp et al., supra). Chicken sympathetic neurons, isolated and prepared as previously described (Trupp et al., supra). Saturation binding with iodinated GDNF was carried out on neurons isolated from embryonic day 10 (E10) chick paravertebral sympathetic ganglia mechanically dissociated in the presence of trypsin. The preparation was preplated for two hours on untreated tissue culture plastic in order to enrich in neurons and allow for re expression of receptors. Plots of saturation binding data produced a sigmoidal curve from which a Kd of 400 pM could be approximated (FIG. 1a). In agreement with the sigmoidal behavior of this curve, Scatchard transformation of the data produced an inverted U-shaped curve indicative of cooperative binding (FIG. 1b). The measure of cooperativity of binding can be ascertained from a Hill transformation which produced a positive slope of 1.63 (FIG. 1c), suggesting oligomerization of either ligand or receptor subunits.

Figure 2:
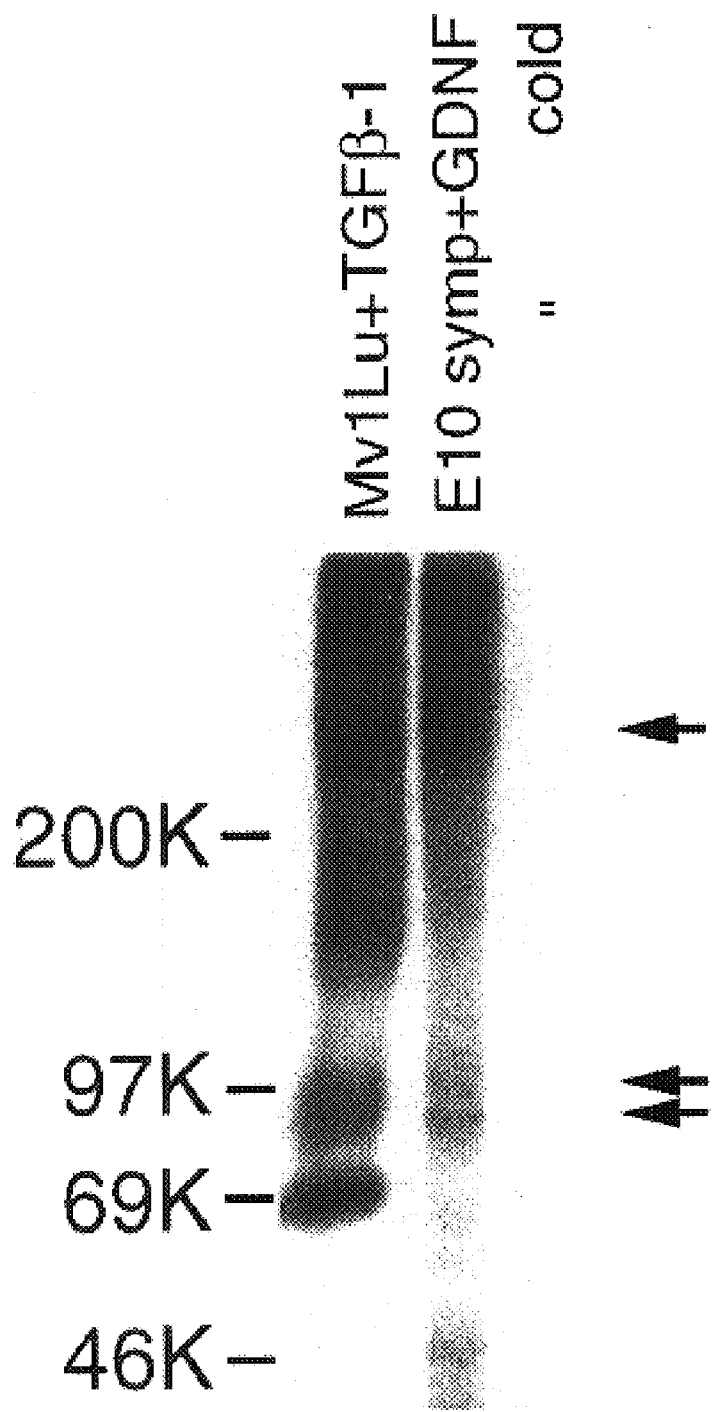
FIG. 2. Affinity labeling of GDNF receptors on chick sympathetic neurons. $^{125}$I-GDNF was cross-linked to E10 embryonic chick sympathetic neurons, receptor complexes were fractionated by SDS/PAGE and visualized by gel autoradiography (middle lane). A doublet at 100 kD and a 300 kD complex are indicated by arrows. Excess cold GDNF prevented cross-linking of $^{125}$I-GDNF (right lane). For comparison, crosslinking of $^{125}$I-TGF-β to mink lung epithelial cells MvILu is also shown (left lane). Molecular weight markers are indicated in kD.

In order to identify GDNF binding components on the membrane of sympathetic neurons, chemical cross-linking of $^{125}$I-GDNF to these cells was utilized, followed by visualization of the resulting complexes by SDS-PAGE. Gradient gel electrophoresis resolved binding proteins of 70 and 300 kD (molecular weights of GDNF receptor subunits reported hereafter were obtained by subtracting the weight of a GDNF ligand monomer, e.g., 23 kD, from the estimated molecular weights of cross-linked complexes visualized by SDS/PAGE), resulting in a pattern of bands which resembled that obtained after cross-linking of TGF-β1 to MvlLu mink lung epithelial cells (FIG. 2). This result suggested that, like TGF-β receptors, GDNF binding proteins may also form an oligomeric receptor system. A large excess of cold ligand displaced iodinated GDNF from the receptor complex indicating the specificity of the labeling.

Example 2

GDNF Receptors on Cell Lines

Over thirty cell lines were screened for expression of GDNF receptors using affinity labeling with iodinated GDNF (Table I, infra). Except as otherwise noted, all cell lines used in this study are available from and described by the American Type Culture Collection, Rockville, Md. A875 human neuroblastoma was provided by Mart Saarma, University of Helsinki, Finland. CATH.A, a noradrenergic cell line isolated from a tumor in the pons of transgenic mice expressing SV40 T antigen under the transcriptional control of a tyrosine hydroxylase promoter (Suri et al., 1993), was generated and provided by Dona Chikaraishi, Tufts University School of Medicine, Boston, Mass. The rat neural stem cell line C17-2 (Snyder et al., 68 Cell 33, 1992) was generated and provided by Evan Snyder, Harvard medical School, Boston, Mass. LAN5 human neuroblastoma was provided by Sven Pahlman, Uppsala University, Sweden. David Hammond, University of Chicago, produced and provided SN6 cells, a hybrid of mouse basal forebrain cholinergic neurons and the mouse neuroblastoma N18TG2 (Hammond et al., 1986). Human neuroblastoma SY5Y was a provided by David Kaplan, ABL-Basic Research Program, NCI-Frederick Cancer Research and Development Center, Frederick, Md. ST15A rat neural stem cell line was kindly provided by Ron McKay, National Instituted of Health, Md. The generation and characterization of raphe nucleus cell lines RN33B and RN46A has been described elsewhere (Whittemore and White, 1993). RN33B and RN46A cells were obtained from Dr. Scott Whittemore of the University of Miami. The motor neuron hybrid cell line 2FI.10.14 (referred to here as MN-1) has been previously described (Salazar-Grueso et al., 2 Neuroreport 505, 1991).

Figure 3:
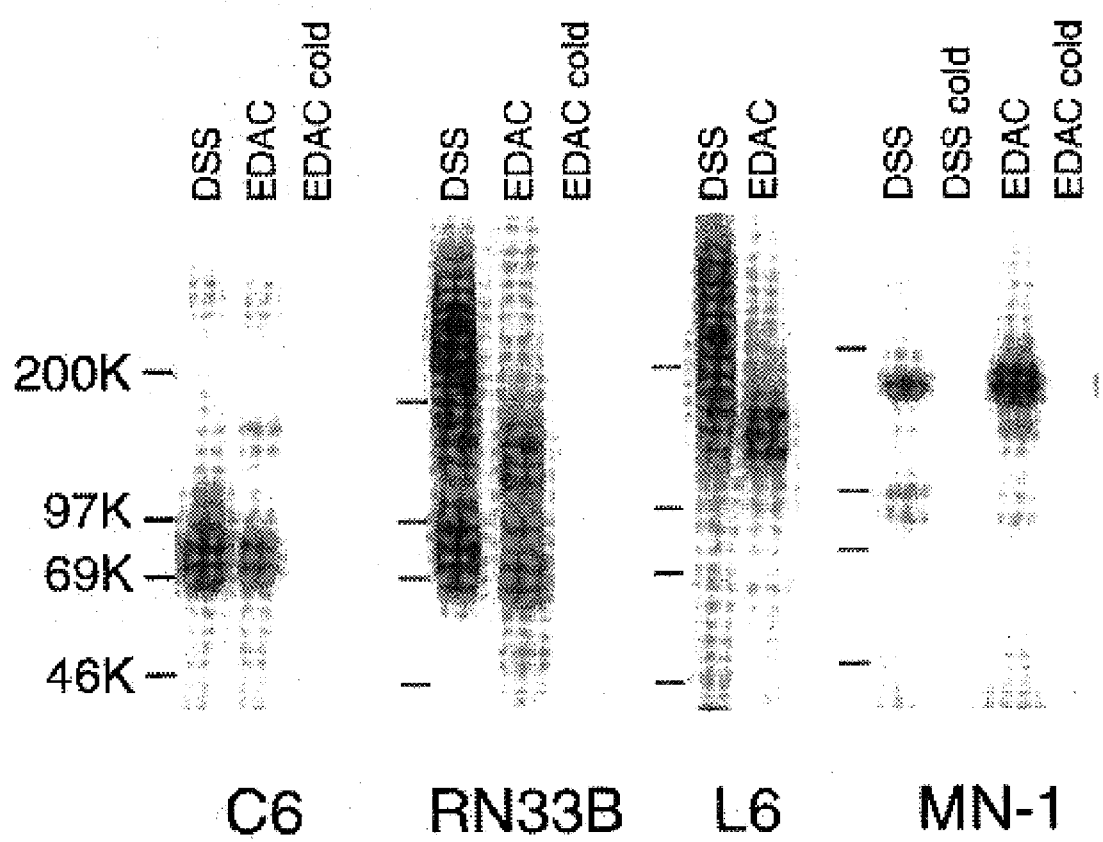
FIG. 3. Affinity labeling of GDNF receptors on cell lines. $^{125}$I-GDNF was cross-linked to C6 glioma, RN33B raphe nucleus, L6 myoblast and MN−1 motor neuron cell lines with either DSS or EDAC as crosslinker agents. Receptor complexes were fractionated by SDS/PAGE and visualized by gel autoradiography. Excess cold GDNF prevented cross-linking of $^{125}$I-GDNF (cold). Molecular weight markers are indicated in kD.

Multiple GDNF receptor subunits were detected in various glial, neuronal and non-neuronal cells (Table I). A large molecular weight band of 300 kD appeared to be the most prevalent species in several cell lines after cross linking with disuccymidyl suberate (DSS), and it was the only receptor which appeared to bind ligand in the absence of all other receptors (Table I). A similar pattern was seen in rat C6 glioma, mouse Sertoli TM4 cells, and in two cell lines derived from embryonic neuronal precursors of the rat raphe nucleus, which have previously been shown to express multiple neuronal markers, including glutamate- (RN33B) and serotonin- (RN46A) synthesizing enzymes (Whittemore and White, 615 Brain Res. 27, 1993; White et al., 14 J. Neuro., 1994; Eaton et al., 170 Dev. Biol. 169,1995). The consensus pattern in these cells after cross-linking with DSS consisted of the large molecular weight band of 300 kD, and two other receptor subunits with molecular weights at 50–55 kD and 65–70 kD, respectively (FIG. 3 and Table I). The 50–55 kD component often ran as a doublet or triplet. The smeary appearance and heterogeneous range of sizes displayed by the large molecular weight component suggests a post-translational modification, presumably glycosylation, and appears similar to that previously described for type III betaglycan TGF-β receptors. This species was somewhat smaller in the cells derived from the raphe nucleus, which could indicate either a distinct core protein or difference levels of glycosylation.

GDNF receptors could not be detected in pheochromocytoma PC12 cells under the present assay conditions of 4° C., even after NGF-induced differentiation into a sympathetic neuron-like phenotype (Table I, and data not shown). No or very low GDNF receptor expression could be seen in various neuroblastomas, and in two pluripotent neuronal stem cells (Table I).

TABLE I

| CELL LINE | DESCRIPTION | 55 kD | 70 kD | 135 kD | 155 kD | 300 kD |
|---|---|---|---|---|---|---|
| A875 | human melanoma | – | – | – | – | + |
| Balb.SFME | mouse embryonic cell | – | – | – | – | – |
| CATH.a | rat pons noradrenergic | – | – | – | – | – |
| Mv1Lu | mink lung epithelia cell | – | – | – | – | – |
| COS-7 | monkey kidney fibroblast | – | – | – | – | – |
| C2-C12 | mouse myoblast | – | – | – | – | – |
| C6 | rat glioma | + | + | + | – | + |
| C17-2 | rat CNS stem cell | – | – | – | – | – |
| FR-3T3 | rat fibroblast | – | – | – | – | – |
| HELA | human cervical carcinoma | – | – | – | – | – |
| LAN5 | human neuroblastoma | – | – | – | – | + |
| L6 | rat myoblast | – | – | + | – | + |
| MN-1 | mouse motor neuron | – | + | – | + | + |
| NB41A3 | TH+ mouse neuroblastoma | – | – | – | – | – |
| NRK-49F | rat kidney fibroblast | – | – | – | – | – |
| PC12 | rat pheochromocytoma | – | – | – | – | – |
| P19 | mouse embryo carcinoma | – | – | – | – | – |
| RN33B | rat raphe nucleus (glutamat) | + | + | + | – | + |
| RN46A | rat raphe nucleus (seroton) | + | + | + | – | + |
| SK-N-MC | human neuroepithelioma | – | – | – | – | – |
| SK-N-SH | DRH+ mouse neuroblastoma | – | + | – | – | + |
| SN6 | mouse basal forebrain (cholin) | – | – | – | – | – |
| ST15A | rat CNS stem cell | – | – | – | – | + |
| SW1353 | human chondrosarcoma | – | – | – | – | – |
| SYSY | human neuroblastoma | – | – | – | – | – |
| TM3 | mouse Leydig cell | – | – | – | – | – |
| TM4 | mouse Sertoli cell | + | + | + | – | + |
| U138MG | human glioblastoma | – | – | – | – | – |

Presence (+) or absence (–) of specific GDNF receptor complexes in the designated cell line.

Affinity labeling using the cross-linker ethyl-dimethyl-aminopropyl carbodiimide (EDAC) revealed the presence of an additional GDNF receptor component of 120–135 kD (FIG. 3), only seen after very long exposure of gels in DSS cross-linked complexes. Like DSS, EDAC also cross-linked GDNF to receptors of 50–55 kD and 65–70 kD; the high molecular weight subunit of 300 kD was, however, not as efficiently cross-linked by EDAC (FIG. 3).

The raphe nucleus cell lines are only conditionally immortalized and do not show signs of transformation. At the non-permissive temperature and in defined medium, they stop proliferating and differentiate into postmitotic neurons (Whittemore and White, 1993). GDNF binding was greatly increased in RN33B and RN46A cells following differentiation (not shown). The overall pattern and the relative amounts of GDNF receptor components did not change after differentiation.

Analysis of GDNF binding proteins on the rat myoblast cell line L6 revealed a different pattern of receptor subunits marked by the apparent absence of 50–55 kD and 65–70 kD receptors. Only the high molecular weight component of 200–400 kD could be seen after cross-linking with DSS (FIG. 3). Cross linking with EDAC, however, readily labeled the 120–135 kD subunit previously seen in C6, TM4 and raphe nucleus cell lines (FIG. 3). As in these other cell lines, this component also run as doublet in L6 myoblasts.

A distinct receptor complex was found on an embryonic mouse spinal cord motor neuron hybrid cell (FIG. 3). This line was obtained by fusion of E14 mouse spinal cord motor neurons and the N18TG2 mouse neuroblastoma, followed by selection of clones expressing high levels of choline acetyltransferase activity (Salazar-Grueso et al., 2 Neuroreport 505, 1991). Importantly, SN6, a hybrid cell line of embryonic mouse basal forebrain cholinergic neurons and the same N18TG2 neuroblastoma (Hammond et al., 234 Science 1237, 1986), showed no GDNF receptors (Table I), indicating that the GDNF binding proteins seen on the motor neuron cell (hereafter referred to as MN-1) are likely to represent GDNF receptor components present in spinal motor neurons. As with the L6 myoblasts, the predominant receptor in MN-1 cells was preferentially cross-linked with EDAC, although in these cells it was a larger protein of 155 kD (FIG. 3). This was subsequently identified to be a c-RET receptor (see Example 9 below). MN-1 cells also expressed 65–70 kD binding proteins and low amounts of the 300 kD receptor (FIG. 3 and Table 1).

Figure 4A:
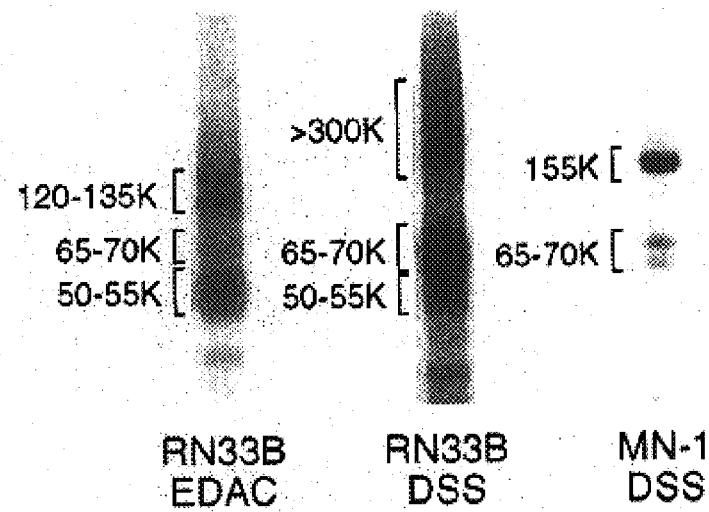
FIGS. 4A–C. Individual constituent affinities of GDNF receptor subunits in RN33B and MN−1 cells. (a) Sizes of different GDNF receptor complexes on RN33B and MN−1 cells after cross linking with EDAC or DSS. (b) and (c) $^{125}$I-GDNF was cross-linked to RN33B (b) or MN−1 (c) cells in the presence of increasing concentrations of cold GDNF. The percentage of $^{125}$I-GDNF binding to the indicated receptor subunit is plotted as a function of the concentration of cold GDNF used during binding.
Figure 4B:
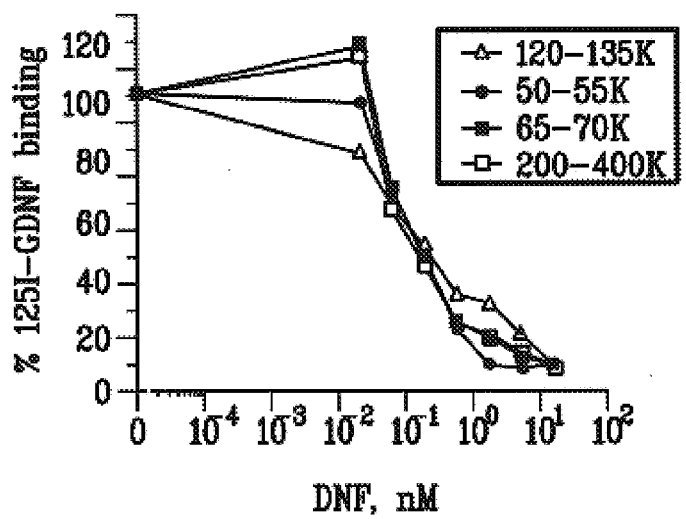
Figure 4C:
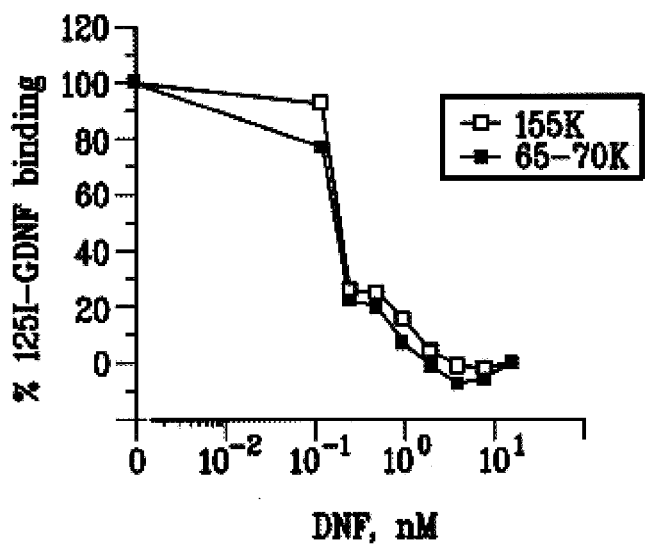

In order to dissect the individual constituent affinities of GDNF receptor subunits, displacement binding assays were performed, followed by cross-linking and SDS-PAGE. Receptor-ligand complexes were visualized by autoradiography, cut out from the gel and counted in a gamma counter. The resulting displacement curves indicated a Kd of approximately 0.2 nM for all components on RN33B and MN-1 cells (FIGS. 4 a–c). These data at present do not clearly establish whether all GDNF receptor subunits display similar binding affinities or, whether they are all required to assemble a high affinity receptor complex.

Example 3
Biochemical Characterization of GDNF Receptors

The overall similarity in the pattern of receptors between GDNF and TGF-β prompted an examination of whether any of the previously identified receptors for TGF-β superfamily members was part of the GDNF receptor complex. Cross-linked $^{125}$I-GDNF-receptor complexes from differentiated RN33B cells were subjected to immunoprecipitation with different anti-peptide antisera specific for all cloned TGF-β superfamily receptors, including type I receptors (ALK-1 to ALK-6), type II receptors TBRII, ActRII and BMPRII, the type III receptors betaglycan, and endoglin. In a parallel control experiment, $^{125}$I-TGF-β1 was cross-linked to type I, type II and type III receptors on the mink lung epithelial cell line MvILu followed by immunoprecipitation with antisera against TBRI (ALK-5), TBRII and betaglycan, respectively. Although type I, type II and type III TGF-β receptors were recovered in the control experiment, none of the GDNF receptor components in differentiated RN33B cells could be immunoprecipitated by any of the tested antisera (not shown). These data confirmed that the GDNF receptor subunits expressed on these cells are novel proteins.

Example 4
Endogenous GDNF Expression in Cell Lines Expressing GDNF Receptors Traditional models for the action of neurotrophic factors have described them as target-derived polypeptides that promote survival and differentiation of specific neuronal subpopulations. More recently, it has become evident that neurotrophic factors may also have paracrine and even autocrine modes of action (Ernfors and Persson, 3 *Eur. J. Neurosci.* 953, 1991; Acheson et al., 374 *Nature* 450, 1995). Expression of GDNF mRNA in cell lines expressing GDNF receptors was examined. Cells were homogenized in guanidine isothiocyanate (GITC) and β-mercaptoethanol. RNA extraction and GDNF RNAse protection assay were as previously described (Trupp et al., supra).

Figure 5A:
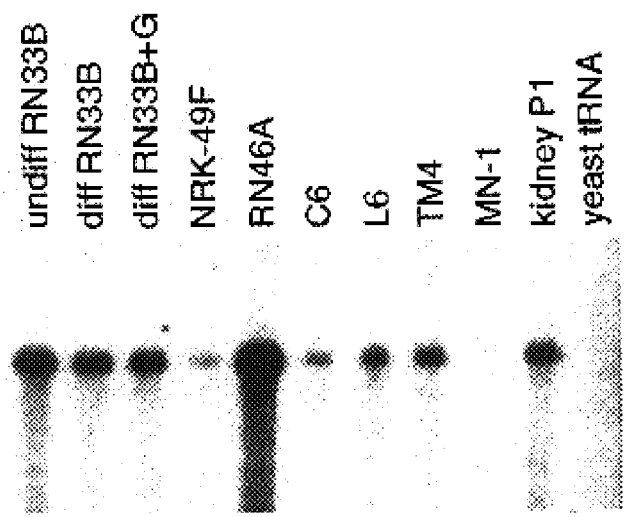
FIGS. 5A–B. Expression of GDNF mRNA in cell lines expressing GDNF receptors. (a) Autoradiogram of an RNAse protection assay using equal amounts of total RNA from the indicated cell lines. Kidney post natal day 1 and yeast tRNA were used as positive and negative controls, respectively. (b) Quantification of the level of GDNF mRNA in different cell lines relative to the level in PI kidney. undiff RN33B, undifferentiated RN33B cells; diff RN33B, differentiated RN33B cells; diff RN338+GDNF, RN33B cells differentiated in the presence of GDNF.
Figure 5B:
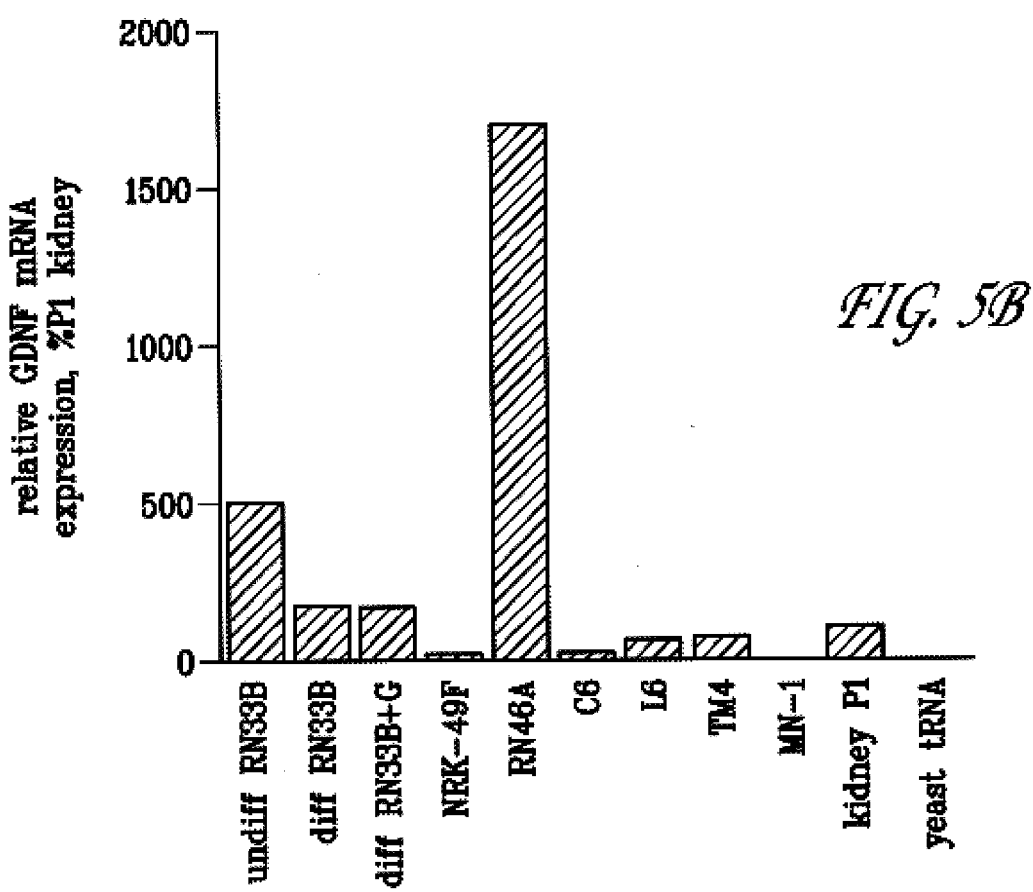

Unexpectedly, all cell lines, with the exception of the motor neuron line MN-1, expressed substantial levels of GDNF mRNA as assayed by RNAse protection analysis (FIG. 5). The highest GDNF mRNA expression was found in cells from raphe nucleus, which showed up to 5-fold higher expression than postnatal day 1 (P1) kidney, one of the richest sources of GDNF mRNA in the developing rat (Trupp et al., supra). Interestingly, upon differentiation of RN33B cells, GDNF mRNA expression decreased to about 30% of the level in undifferentiated cells (FIG. 5). GDNF treatment of differentiated RN33B cells did not alter the expression of GDNF mRNA (FIG. 5) or GDNF receptors (not shown).

Figure 6:
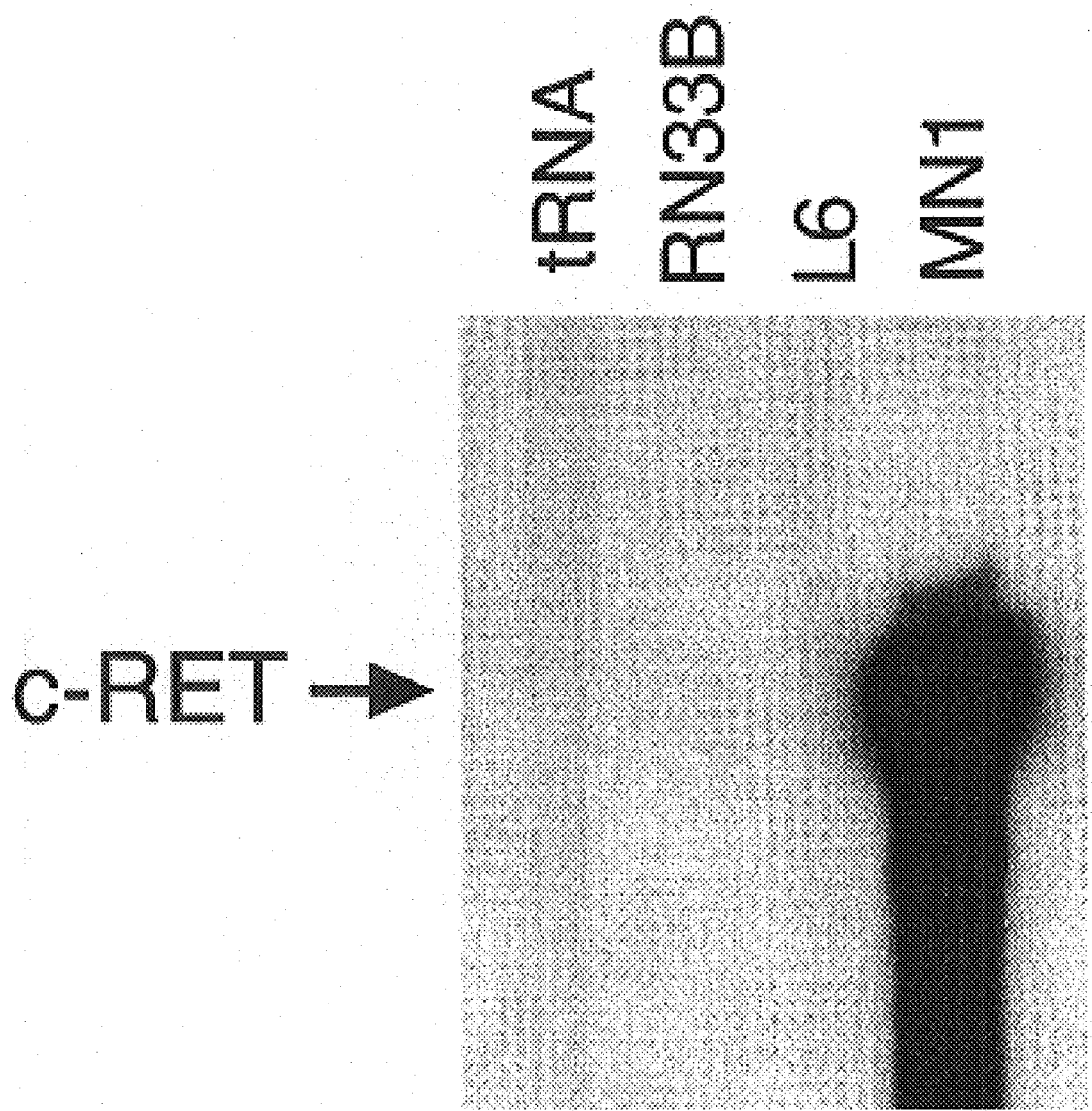
FIG. 6. Expression of mRNA for c-ret in different cell lines.

Expression of c-ret mRNA was investigated in RN33B, L6, and MN-1 cells, using the RNAse protection assay. Ten micrograms of total RNA from the cell lines indicated was analyzed using a riboprobe complementary to 400 nucleotides of coding sequence from the kinase domain of the mouse c-ret mRNA. Although high expression was seen in MN-1 cells, no c-ret mRNA was detected in either the RN33B or L6 cells (FIG. 6). These results indicate that a signaling receptor for GDNF other than c-RET must be present in these cells.

Example 5
Activation of the ERK Signal Transduction Pathway in GDNF Responsive Cell Lines Whether the GDNF binding proteins characterized in cell lines were able to form ligand-dependent signaling complexes was also investigated. Cell monolayers in 10 cm plates were incubated at 37° C. in the presence of 50 ng/ml GDNF for the indicated time periods and immediately lysed with 1 ml of ice cold lysis buffer (as above) with the addition of 1 mM sodium othovanadate. Whole cell lysates were fractionated by SDS-PAGE (10% polyacrylamide) and blotted to nitrocellulose filters. Western blots were probed with an anti-phosphotyrosine antiserum (UBI, Lake Placed, N.Y.), followed by horseradish peroxidase-conjugated goat anti-mouse IgG and developed with the ECL Western Detection System (Amersham, UK). For reprobing, blots were first stripped by a 30 minute incubation at 50° C. in 62.5 mM Tris-HCl pH6.7, 100 mM β-mercaptoethanol, 2% sodium dodecyl sulphate. After removal of antibodies, blots were probed with a rabbit polyclonal antisera raised against recombinant rat ERK2 (a gift of Teri Boulton, Regeneron Pharmaceuticals Inc., Tarrytown, N.Y.) which recognizes both ERKI and ERK2, and developed as above using a horseradish peroxidase-conjugated goat anti-rabbit secondary antibody.

Figure 7A:
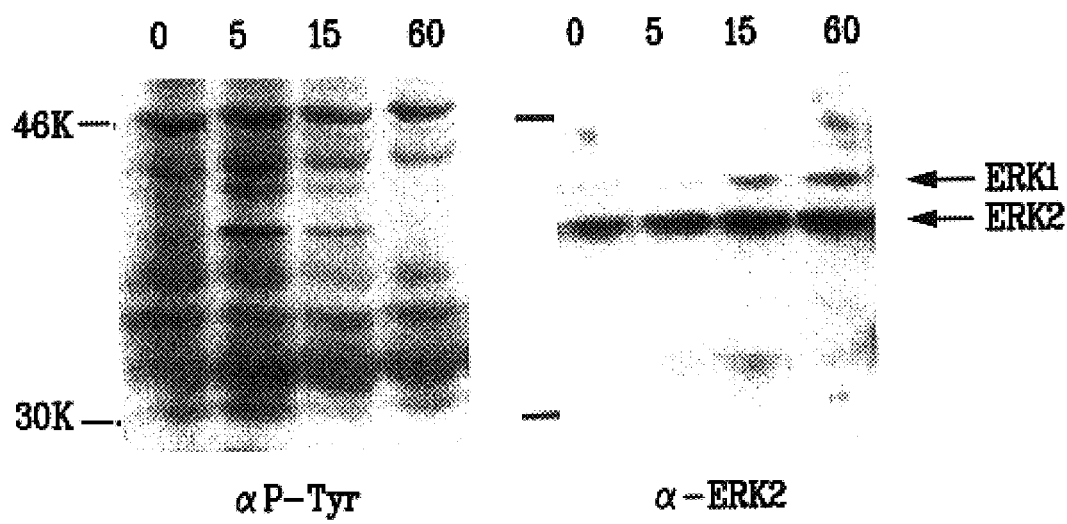
FIGS. 7A–B. GDNF stimulation of tyrosine phosphorylation of ERKs in RN33B and MN−1 cells. RN33B (a) or MN−1 (b) cell monolayers were exposed to 50 ng/ml GDNF during the indicated periods of time (in minutes), cell lysates were fractionated by SDS/PAGE and Western blots probed with an anti-phosphotyrosine antibody (aP-Tyr). The blots were stripped and reprobed with an anti ERK2 antibody (a-ERK2) that recognizes both p42$^{erk}$12 and p44$^{erk1}$ (arrows to the right). Molecular weight markers are indicated in kD.

Because of their distinct patterns of GDNF receptor subunits, intracellular signaling responses were initially characterized in the raphe nucleus cell line RN33B and in the motor neuron cell line MN-1. Changes in the pattern of tyrosine-phosphorylated proteins elicited by GDNF treatment of RN33B or MN-1 cells were investigated. Tyrosine phophorylation is a universal mechanism of regulation of intracellular signaling proteins that is stimulated by numerous cytokines and growth factors. RN33B and MN-1 monolayers were exposed to a saturating concentration of GDNF (5 ng/ml) for different periods of tine, and total cell lysates were analysed for tyrosine phosphorylation by SDS/PAGE and Western blotting with an anti-phosphotyrosine monoclonal antibody. Two proteins with mobilities corresponding to 42 kD and 44 kD, respectively, were phosphorylated on tyrosine within 5 minutes of GDNF treatment of RN33B cells (FIG. 7A). A similar result was obtained in differentiated RN33B cells (not shown) of exposure to GDNF.

Figure 7B:
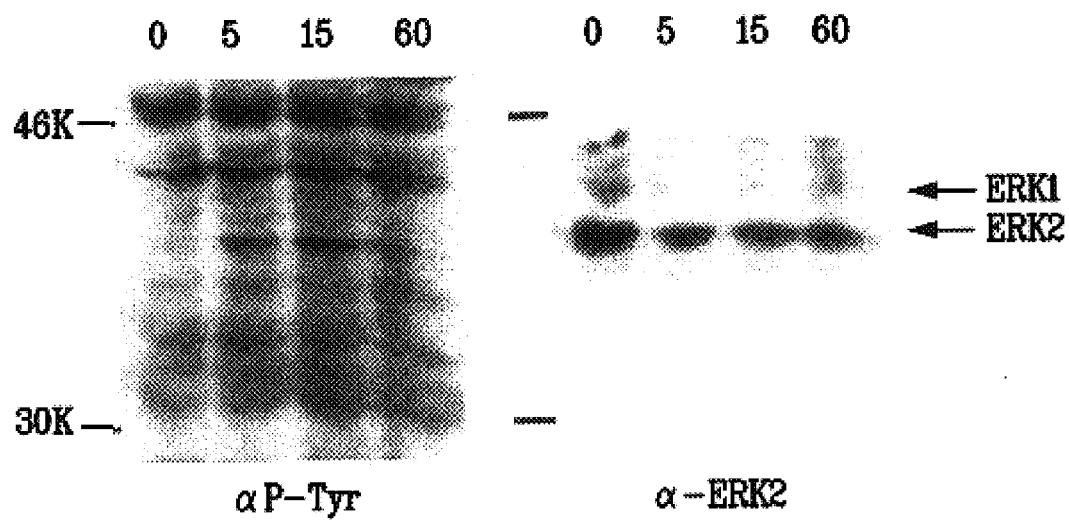

Based on comparison of their size with descriptions of growth factor-induced protein tyrosine phosphorylation elsewhere (Qiu and Green, 9 Neuron 705, 1992), the 42 kD and 44 kD species would appear to be, respectively, p42,k2 and p44,kI, two protein serine-threonine kinases members of the extracellular signal-regulated kinase (ERK, also termed microtubule-associated protein kinase) family (Boulton et al., 65 *Cell* 663, 1991). To confirm the identity of these proteins as ERK2 and ERKI, respectively, protein blots which had been reacted with the anti-phosphotyrosine antibody were stripped and reprobed with a rabbit polyclonal antibody raised against recombinant ERK2 that recognizes both ERKI and ERK2 in protein blots. Comparison of autoradiograms of blots probed with the anti-phosphotyrosine antibody and the anti-ERK2 antibody identified the p42 and p44 proteins as ERK2 and ERKI, respectively (FIG. 7a). Although GDNF treatment of MN-1 cells appeared to only stimulate phosphorylation of ERK2, both ERKI and ERK2 were present in MN-1 cell lysates (FIG. 7b). Thus, GDNF treatment stimulated very rapid and transient tyrosine phosphorylation of ERKI and ERK2 in RN33B cells, but relatively slower and more sustained phosphorylation of ERK2 and MN-1 cells.

Activation of the ERK pathway has previously been shown to induce rapid and transient increase in transcription of immediate early genes, including the c-fos proto-oncogene (Gille et al., 358 *Nature* 414, 1992). Accordingly, the ability of GDNF to induce c-fos mRNA in differentiated raphe nucleus RN33B cells and in motor neuron MN-1 cells was investigated. For analysis of c-fos mRNA expression in cell lines, culture medium was changed 90 minutes prior to addition of 100 ng/ml GDNF to cell monolayers. At the indicated time intervals, media was removed, cells solubilized with guanidine isothiocyanate and β-mercaptoethanol and RNA extracted as previously described (Trupp et al., supra). Twenty micrograms of total RNA was fractionated on 1% agarose gels containing 0.7% formaldehyde and transferred to Hybond-C membranes (Amersham, UK). Northern blots were hybridized with an a-$^{32}$P-dCTP labeled rat c-fos gene fragment (Curran et al., 2 *Oncogene* 79, 1987), washed at high stringency and visualized by autoradiography on x-ray films.

Figure 8A:
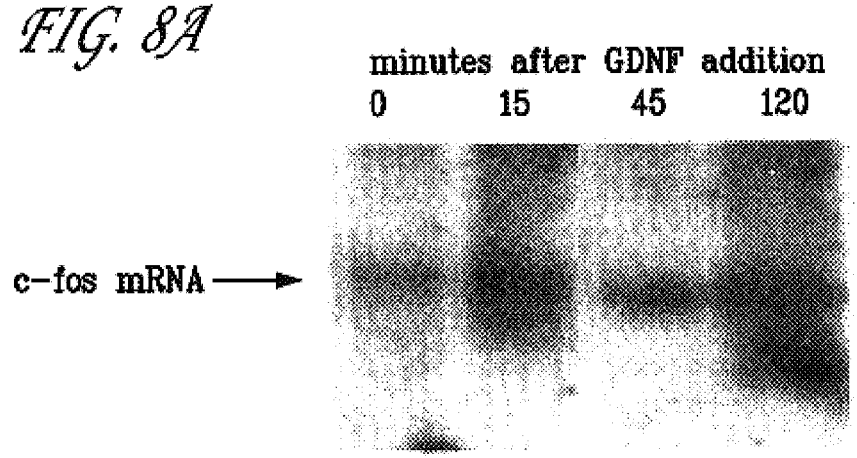
FIGS. 8A–B. GDNF stimulation of c-fos mRNA expression in RN33B and MN−1 cells. RN33B (a) or MN−1 (b) cell monolayers were exposed to 50 ng/ml GDNF during the indicated periods of times, total RNA was extracted and fractionated in agarose gels and Northern blots probed with a $^{32}$P-labeled rat c-fos probe. Shown are x-ray autoradiograms of filters washed at high stringency.
Figure 8B:
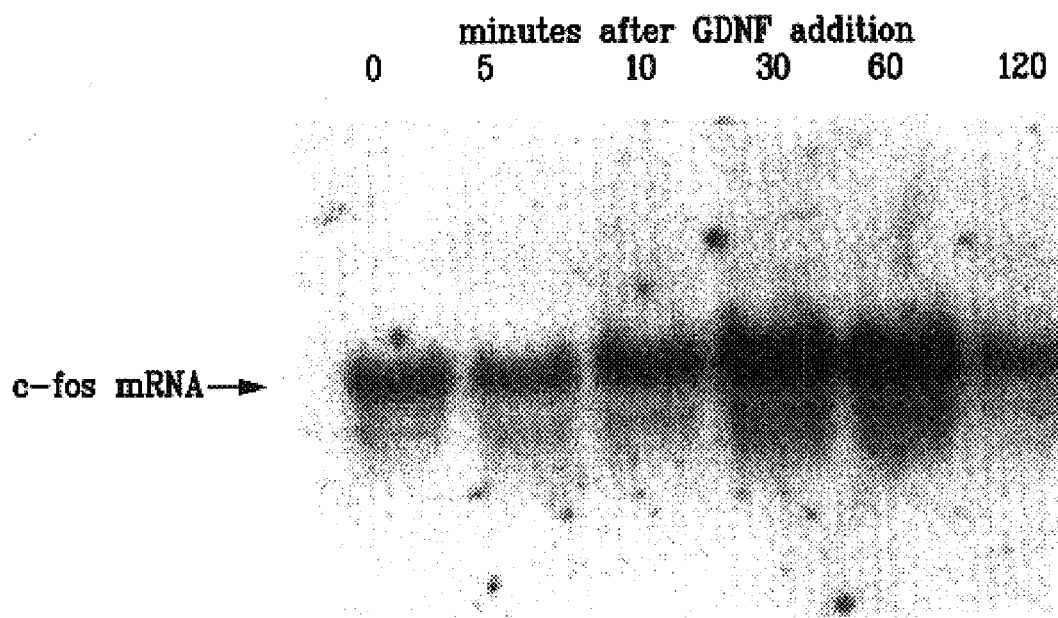

Cell monolayers were exposed to saturating concentrations of GDNF for different periods of time and levels of c-fos mRNA were subsequently analyzed in Northern blots of total RNA (FIG. 8). This analysis revealed transient upregulation of c-fos mRNA 15 minutes after exposure of RN33B cells to GDNF, returning to basal levels 45 minutes after treatment (FIG. 8a). c-fos mRNA was also upregulated in MN-1 cells but not until 30 minutes of GDNF treatment (FIG. 8b). Elevated c-fos mRNA levels persisted for about an hour and returned to basal levels 120 minutes after the initiation of treatment (FIG. 8b). Thus, like tyrosine phosphorylation of ERKS, c-fos mRNA upregulation induced by GDNF treatment was very rapid and transient in RN33B cells, but somewhat slower in MN-1 cells.

Example 6
Survival Responses Promoted by GDNF in Differentiated Raphe Nucleus Cells Advantage was taken of the conditional nature of the immortalization of the raphe nucleus serotonergic cell line RN46A by examining whether GDNF may be a survival factor for differentiated raphe nucleus neurons. Survival assays were performed as previously described (Eaton et al., 1995, supra). Briefly, $10^5$ RN cells were seeded to collagen/fibronectin coated 8-well glass slides and incubated at 33° C. (growth permissive temperature) until 75–90% confluent. The slides were then shifted to 39° (non-permissive temperature) and serum containing medium was replaced by B16 defined medium (Brewer and Cotman, 494 *Brain Res.* 65,1989) containing 1% BSA, 1 μg/ml transferrin, 5 μg/ml insulin, 100 mM putrescine, and nM progesterone plus or minus 0–50 ng/ml rhGDNF (Promega, Madison, Wis.). Media and GDNF were replaced every two days for 8 days after which the cells were fixed in 4% paraformaldehyde/2% glutaraldehyde, rinsed and coated with a glycerol mounting medium containing 1 mM bisbenzamide (Hoechst dye 33342) to stain viable nuclei. Fields of cells were magnified to 40× on a Zeiss Axiophot microscope, examined for fluorescent nuclei (at 355 nM excitation, 465 nM emission), the images video captured, and the cells counted with Imade I™ software. For each condition, 10 fields of cells were counted from each of 3 independent experiments.

RN46A cells were cultured at the non-permissive temperature in defined medium in the presence of increasing concentrations of GDNF. Nine days after plating, surviving cells were counted and compared with cultures established in the absence of GDNF. A 3-fold increase in the number of surviving cells was observed in cultures grown in the presence of GDNF (FIG. 9). The effect of GDNF on the survival of differentiated RN46A cells was dose dependent, with an EC50 at 5 ng/ml.

Example 7
Generation, Cloning and Characterization of Anti-GDNF Monoclonal Antibodies
Immunisation Five young female mice were immunised with 35 ug of insect cell-derived recombinant GDNF emulsified with complete Freund's adjuvant (FA). Second and third immunizations were performed 2 and 4 weeks after the first one in incomplete FA. All the injections were given intraperitoneally (i.p.). Two weeks after the last Immunisation, antibody titer in serum was checked by ELISA and Western Blot analysis using standard methods. The mouse with the highest titer (more than 1:2000) was boosted i.p. with 3 μg of GDNF in incomplete FA 3 days before the cell fusion.
Cell Fusion Cell fusion was done according to the method of Kohler and Milstein (1975), incorporated herein by reference, with some modifications.

a) Day before fusion:

Viable cells from the Sp2/0 murine cell line were adjusted to $2 \times 10^5$ cells /ml with complete DMEM (10% fetal calf serum, 1% L-glutamine, 100 U/ml penicillin and 100 ug/streptomycin sulphate).

Cells from a non-immunised mouse were obtained from the peritoneal cavity by injection of 0.34 M sucrose solution. The cells were resuspended in complete DMEM containing: hypoxanthine 100 μM; aminopterin 0.4 M; and thymidine 16 μM, (HAT medium), to $1 \times 10^5$ cells /ml. 100 μl of the cell suspension was added to the 60 inner wells of 96 well plates and incubated overnight at 37° C. in an atmosphere of 5% $CO_2$ in air. These cells were the source of growth factors.

b) Fusion

Spleen cells from the mouse exhibiting the highest serum titer (see above) were homogenized in 10 ml DMEM removing surface fat and other adhering tissue in a sterile hood.

$4.2 \times 10^7$ Sp2/0 cells were fused with $8.4 \times 10^7$ spleen cells in a solution of melted PEG (3000–3700, Hybri-Max, Sigma). The cells were then grown in HAT medium at 37° C. in an atmosphere of 5% $CO_2$ in air. After one week of culture, the wells were inspected. When hybrids cells covered 10 to 50% of the surface area of the well, the culture supernatants were assayed for antibody by ELISA.

For the ELISA, wells of microplates (Costar, EIA/RIA plate high binding) were coated with 100 ul of 2 ug/ml of GDNF diluted in carbonate/bicarbonate buffer, pH 9.6. After an overnight incubation at 4° C., the wells were washed with 0.05M phosphate buffered saline, pH 7.2, containing 0.05% Tween (PBS-T). Nonspecific binding was blocked with PBS-T containing 3% non-fatty milk and 1% goat normal serum. Supernatant samples were incubated 4 hours at room temperature. Peroxidase goat anti-mouse antibody was used and the substrate was o-phenylenediamine dihydrochloride (OPD). Plates were read at 492 nm in an ELISA reader. Negative controls included completed medium and normal mouse serum.

The hybrids were grown in HAT medium up to two weeks after fusion. Cells were subsequently grown in HT medium until the completion of two cloning procedures, using the limiting dilution method. After each step (when cells reached 10 to 50% confluence), assays for specific antibody in supernatants were done by ELISA. Upon recloning, 5 positive hybridoma clones were chosen and the cells were maintained in complete DMEM for 30 days.
Isotyping of Monoclonal Antibodies The class and subclass of the monoclonal antibodies were determined by ELISA using a DAKO panel for isotyping of mouse monoclonal antibodies. All five 5 monoclonal antibodies were characterized as $IgG_1$.

Purification of Monoclonal Antibodies

Monoclonal antibodies from culture supernatants were purified by Protein G Sepharose fast flow (Pharmacia, Biotech) according to manufacturer's instructions. Culture supernatants were concentrated and filtered through a 0.45 μm membrane (Schleicheer and Schull, Germany) and then pumped overnight through the column previously equilibrated with 20 mM sodium phosphate, pH 7.0. Ig was eluted with 0.05M glycine buffer.

Example 8

A Motor Neuron Cell Line Showing Biological and Biochemical Responses to GDNF

Figure 10A:
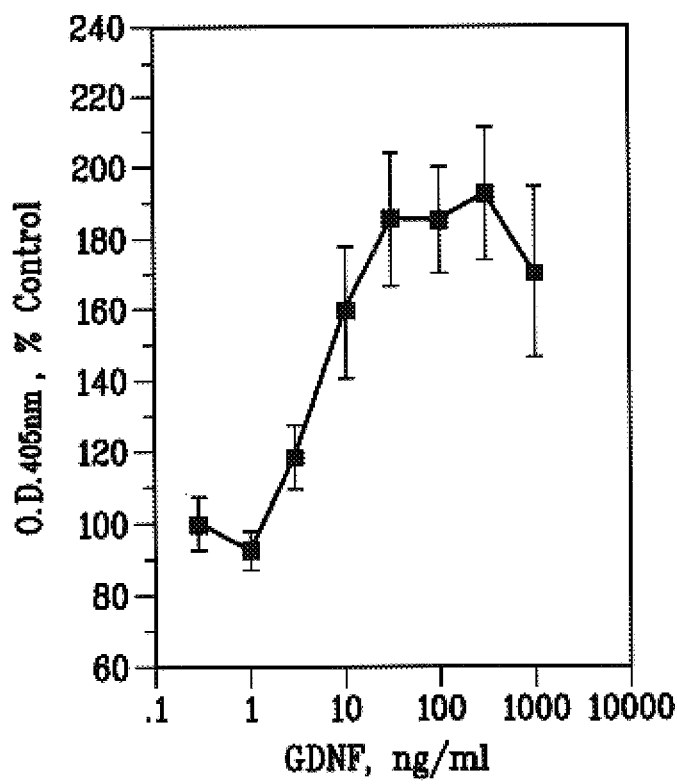
FIGS. 10 a–c. Biological and biochemical responses of MN−1 to GDNF. (a) GDNF stimulates survival of serum-deprived MN−1 cells. (b)GDNF stimulates rapid and transient tyrosine phosphorylation of several proteins (asterisks) in MN−1 cells. Time of GDNF treatment (in minutes), and molecular weight markers are indicated. (c) Rapid and sustained ERKI and ERK2 tyrosine phosphorylation stimulated by GDNF in MN−1 cells.

MN-1 cell monolayers were exposed to increasing concentrations of GDNF in serum-free medium and assayed 3 days later for cell survival and growth by measurement of acid phosphatase activity (Clontech). GDNF was produced and purified from baculovirus infected insect cells as previously described (Trupp et al.,supra). GDNF treatment of serum deprived-MN-1 monolayers increased cell number in a dose-dependent manner (FIG. 10a). The biological response of MN-1 cells correlated with biochemical and transcriptional responses to GDNF treatment. MN-1 cell monolayers were exposed to 50 ng/ml GDNF for increasing periods of time, cell lysates were fractionated by SDS/PAGE and Western blots probed with an anti-phosphotyrosine antibody (UBI).

Figure 10B:
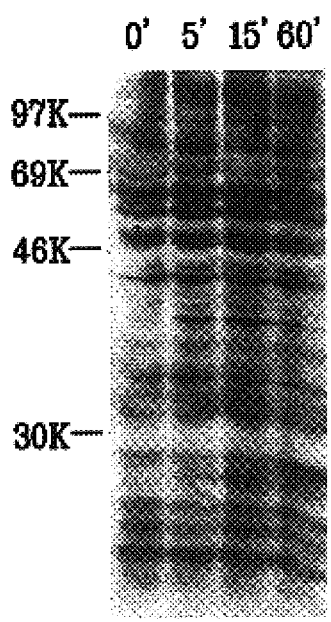
Figure 10C:
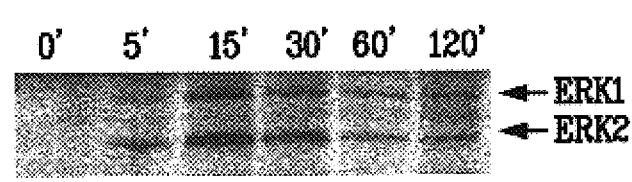

Several proteins were seen to have increased tyrosine phosphorylation after GDNF treatment of MN1 cells, including a protein with an electrophoretic mobility of 42K (FIG. 10b). Based on comparison of its size with descriptions of growth factor-induced protein tyrosine phosphorylation elsewhere (Boulton, T. G., et al. Cell 65, 663–75 (1991), the 42K species would appear to be $p42^{erk2}$, a serine-threonine kinase member of the extracellular signal-regulated kinase (ERK) family. The identity of this protein as ERK2 was confirmed after immunoprecipitation with an antiERK2 polyclonal antiserum followed by analysis of tyrosine phosphorylation (FIG. 10c). Lysates of GDNF-stimulated MN-1 cells were immunoprecipitated with an anti-ERK2 antiserum (Santa Cruz) that also recognizes ERKI followed by antiphosphotyrosine Western blotting. This analysis further revealed that another member of the ERK family, p44erk1, was also phosphorylated on tyrosine after GDNF treatment of MN-1 cells (FIG. 10c). Activation of the ERK pathway has previously been shown to induce a rapid and transient increase in the transcription of immediate early genes, including the c-fos proto-oncogene (Gille et al., Nature 358, 414–7 (1992).

Example 9

Figure 11A:
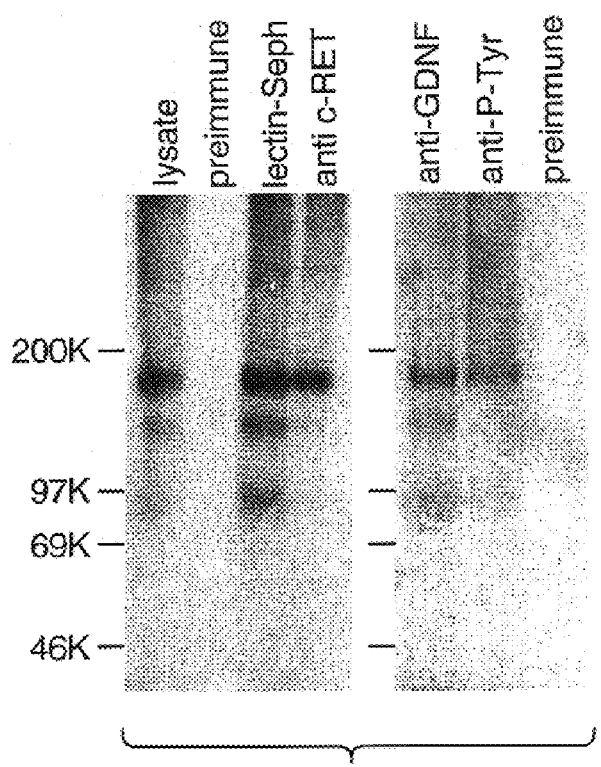
FIGS. 11 a–b. c-RET is a signal transducing receptor for GDNF. (a) Immunoprecipitation analysis of GDNF-receptor complexes in MN−1 cells. GDNF-labeled binding proteins could be precipitated with lectin Sepharose beads, or antibodies against GDNF, phospho-tyrosine (P-Tyr) and c-RET. Control preimmune antibodies did not inumunoprecipitate GDNF receptor complexes. (b) GDNF induces tyrosine phosphorylation of c-RET in MN−1 cells. c-RET tyrosine phosphorylation was detected already 5 minutes after addition of GDNF (upper panel). Saturation was observed at 30 ng/ml GDNF (lower panel).

The Product of the c-ret Proto-oncogene as a Signal Transducing Receptor for GDNF GDNF receptor complexes from MN-1 cells could be recovered by immunoprecipitation with anti-GDNF antibodies or by binding to lectin-Sepharose beads (FIG. 11a). Unexpectedly, the 180 kD receptor complex (i.e., c-RET; 180 kD-23 kD=157 kD, which is approximately equal to the 155 kD receptor identified as c-RET—see Example 2, infra) could also be recovered by immunoprecipitation with anti-phosphotyrosine antibodies (FIG. 11a), indicating that the GDNF binding protein in this complex could be a receptor tyrosine kinase.

The product of the c-ret proto-oncogene is highly expressed in primary motor neurons (Pachnis et al., supra, and Tsuzuki, T., et al. Oncogene 10, 191–8 (1995) and is of similar molecular weight as the major GDNF receptor component detected in MN-1 cells (Takahashi, M., et al. Oncogene 3, 571–578 (1988). We tested whether this species represented a C-RET-GDNF cross-linked complex by immunoprecipitation with anti-c-RET antibodies.

$^{125}$I-GDNF was cross-linked to MN-1 cells using EDAC and receptor complexes were precipitated with antibodies against GDNF (Trupp et al., supra), lectin Sepharose beads (Formica), anti-phosphotyrosine antibodies (UBI), anti-c-RET antibodies (Santa Cruz) and control antibodies from non-immune rabbits. An antipeptide c-RET rabbit antiserum readily immunoprecipitated the major 180 kD ligand-receptor complex in MN-1 cells (FIG. 11a), while a number of unrelated monoclonal and polyclonal antibodies used as controls failed to immunoprecipitate this complex (FIG. 11a and data not shown).

Figure 11B:
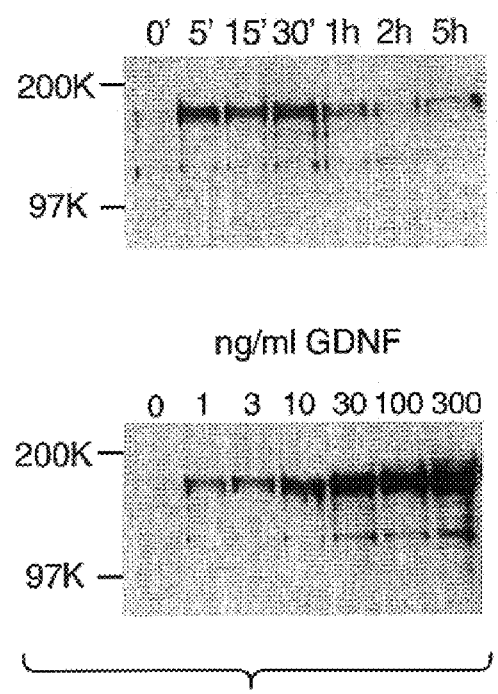

Because the product of the c-ret gene is a receptor tyrosine kinase, we investigated whether GDNF could stimulate tyrosine phosphorylation of the c-RET protein in MN-1 cells. MN-1 cell monolayers were exposed to GDNF at different concentrations or for different periods of time and cell lysates were immunoprecipitated with anti-c-RET antibodies and analyzed by SDS/PAGE and Western blotting with antiphosphotyrosine antibodies as disclosed above. GDNF treatment stimulated rapid c-RET tyrosine phosphorylation in MN-1 cells (FIG. 11b). Maximal phosphorylation was reached 5 minutes after GDNF treatment and lasted for at least 60 minutes. A dose-response analysis of GDNF induced c-RET phosphorylation in MN-1 cells showed maximal phosphorylation at 30 ng/ml of GDNF (FIG. 11b), which is similar to the response of both serum deprived MN-1 cells (FIG. 10a) and embryonic sympathetic neurons (Trupp et al., supra) to GDNF. Taken together, these data indicate that the c-RET receptor may be an important component in the signal transduction mechanism of GDNF.

Example 10 c-ret Transfection Reconstitutes GDNF Binding and Biological Activities to GDNF

Experiments were conducted to determine whether expression of the c-ret gene product could be sufficient to allow binding of GDNF to cells lacking GDNF receptors. To this end, GDNF binding and cross-linking experiments were performed in naive 3T3 fibroblasts, and 3T3 cells stably transfected with either a wild type c-ret or an oncogenic form of this gene found in MEN2a patients (Mulligan et al., Nature, 363:458–460, 1993). For c-ret expression in transfected cells, human wild type c-ret and MEN2a-ret cDNAs were subcloned in pcDNA3 (Invitrogen). Cold GDNF was used at 50×molar excess. For survival/growth assays, cells were cultured for 6 days in serum-free medium supplemented with the indicated concentrations of GDNF; medium and GDNF were replaced every two days. Cell number was quantified by measurement of acid phosphatase activity (Clontech).

Figure 12A:
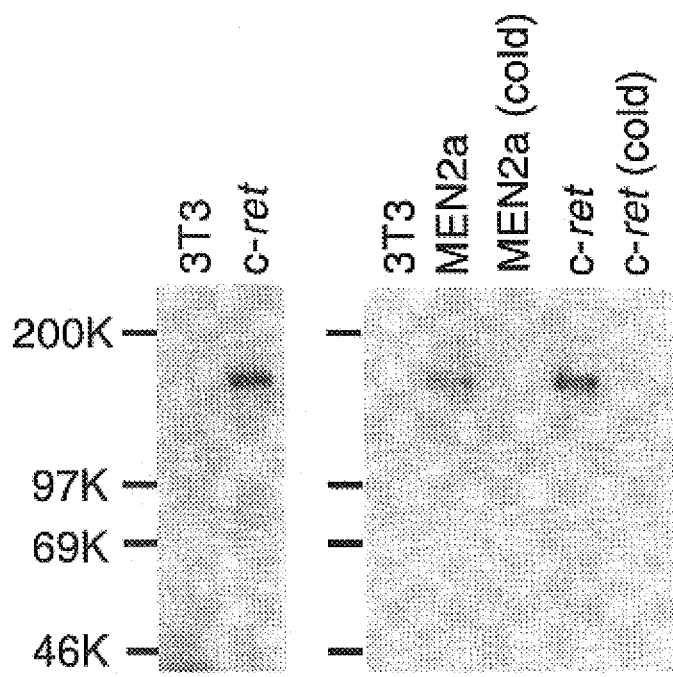
FIGS. 12 a–b. c-ret expression is sufficient to mediate binding and biological responses to GDNF in fibroblasts. (a) Iodinated GDNF could be cross linked to 3T3 cells stably transfected with MEN2a-ret or wild type c-ret expression plasmids. Untransfected 3T3 cells (3T3) did not bind GDNF. The specificity of the binding was demonstrated by displacement of the labeling with 50× excess cold GDNF. (b) GDNF promotes survival and growth responses in 3T3 fibroblasts stably transfected with a c-ret expression plasmid. Untransfected cells did not respond to GDNF.

After immunoprecipitation with c-RET antibodies, GDNF-labeled receptor complexes of approximately 180K were detected in both MEN2a-ret and c-ret transfected 3T3 fibroblasts, but not in untransfected cells (FIG. 12a). The labeling could be displaced by excess cold GDNF, indicating that it represented specific GDNF binding (FIG. 12a).

Figure 12B:
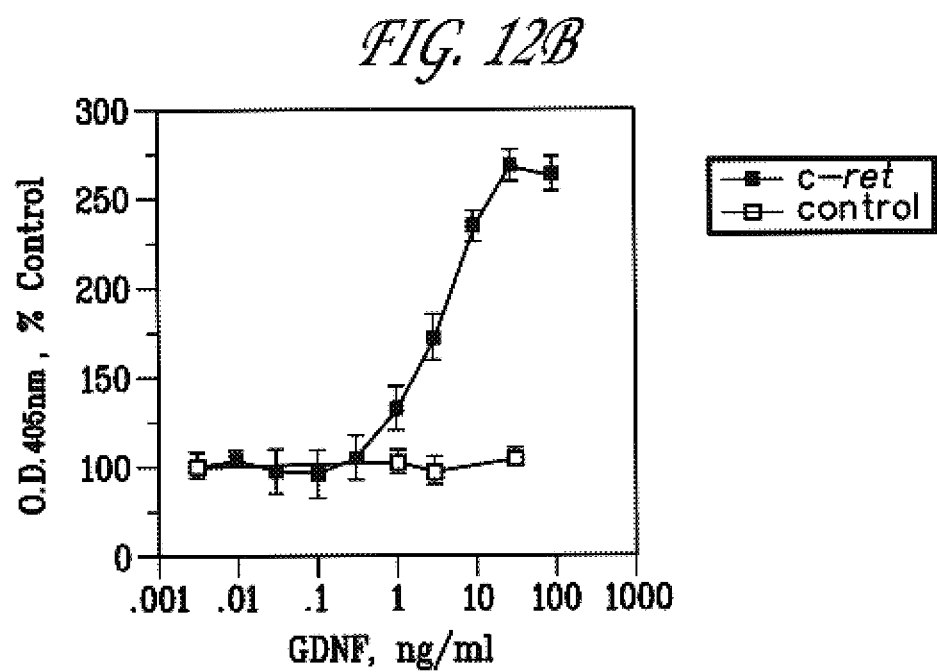

Experiments were also conducted to determine whether c-ret could mediate a biological response to GDNF upon transfection in non-responsive cells. Survival and growth responses to GDNF were investigated in untransfected and c-ret transfected 3T3 fibroblasts cultured in serum-free medium. GDNF elicited a dose-dependent increase in cell number in c-ret transfected, but not in untransfected, 3T3 cells (FIG. 12b) which was comparable to the one previously observed in serum-deprived MN-1 cells. Since naive 3T3 cells did not express any appreciable amount of GDNF receptors prior to transfection (see FIG. 12a), it was concluded that c-ret expression was sufficient for mediating a biological response to GDNF in these cells.

Example 11 c-ret Expression in Adult Brain and Dopaminergic Neurons of the Substantia Nigra Experiments were conducted to determine whether the c-ret product may mediate the neurotrophic effects of GDNF in the brain by examining the expression of c-ret in different regions of the rat central nervous system. A rat c-ret riboprobe was generated using as template a cDNA fragment obtained by PCR with primers based on sequences U22513 and U22514 (Genbank accession numbers). High levels of c-ret mRNA were found in MN-1 cells and in rat spinal cord (data not shown). High c-ret mRNA expression was also found in the adult pons, medulla, locus coeruleus and hypothalamus (FIG. 13a), as well as in thalamus and cerebellum (data not shown). c-ret mRNA was expressed at barely detectable levels in striatum, hippocampus and cerebral cortex (FIG. 13a). In the ventral mesencephalon, containing the cell bodies of GDNF-responsive dopaminergic neurons, c-ret mRNA levels increased progressively during post-natal development (FIG. 13b). A peak of expression was detected between post natal day 6 (P6) and P8, at which time axons of dopaminergic neurons of the substantia nigra begin innervation of the striatum, and coincident with an increase in GDNF mRNA expression in this target region (FIG. 13b). For mRNA quantification, a glyceraldehyde-3-P dehydrogenase (GAPDH) riboprobe was included in the RPA, and values of relative mRNA expression, obtained after densitometric scanning of gel autoradiograms, were normalised using the GAPDH signal of each RNA sample. RPA for GDNF mRNA has been previously described (Trupp et al., supra).

In situ hybridisation and immunohistochemistry were performed as previously described (Arenas, E. & Persson, H. *Nature* 367, 368–371 (1994); Neveu, I & Arenas, E. *J. Cell Biol.* in press (1996). c-RET protein was detected using a hamster monoclonal anti-mouse c-RET antibody which also recognises rat c-RET (Lo, supra) followed by fluorescein-conjugated rabbit anti-hamster secondary antibodies (Southern Biotechnologies). In situ hybridization on sections through the adult substantia nigra revealed strong labelling over neurons throughout this structure (FIGS. 14 a–b). In addition, cells positive for c-RET-like immunoreactivity (c-RET-LI) were found throughout the adult substantia nigra, with strong labelling over cell bodies (FIG. 14c).

In order to establish that c-ret expression in the adult substantia nigra was confined to dopaminergic neurons, these cells were selectively lesioned with a unilateral injection of 6-hydroxydopamine (6-OHDA); the cells were then analyzed for c-ret mRNA expression by in situ hybridisation. Lesions of dopaminergic neurons of the substantia nigra were performed by stereotaxic injections of 8 pig 6-OHDA in the medial forebrain bundle at the following coordinates: 1.6 mm caudal to bregma, 1.3 mm lateral to midline, and 8.4 mm under the dural surface with the incisor bar 5 mm over the interaural line. Animals were pretreated with 25 mg/kg desipramine (i.p.) 30 minutes prior to 6-OHDA injection. $0.75 \times 10^6$ GDNF-expressing fibroblast cells in 3 μl of medium were injected supranigrally at the following coordinates: 3,1 mm from interaural line, 2 mm lateral to midline, and 7 mm under the dural surface, with the incisor bar at −3.3 mm. Lesion and grafting in the locus coeruleus were as previously described (Arenas et al., *Neuron* 15, 1465–1473 (1995). The generation and characterisation of GDNF expressing fibroblasts have been described previously (Arenas et al., supra).

Five hours after the lesion, no difference could be seen between ipsi and contralateral sides in c-ret mRNA expression (FIG. 14d). However, a marked reduction in c-ret mRNA expression was seen in the lesioned substantia nigra already one day after 6-OHDA treatment, and was nearly absent 5 days after the lesion (FIG. 14d). c-ret mRNA expression in the side contralateral to the lesion was, however, not affected (FIG. 14d). This result indicated that in the adult substantia nigra, c-ret mRNA expression was confined to dopaminergic neurons.

Example 12

GDNF Rescues c-RET-Positive Dopaminergic and Noradrenergic Neurons

Experiments were conducted to determine whether c-RET expressing neurons of the adult substantia nigra and locus coeruleus responded to GDNF. For this, nigral dopaminergic neurons lesioned with 6-OHDA, and were then examined to determine whether grafts of GDNF expressing fibroblasts induced responses on c-RET immunoreactive neurons. In lesioned animals that received a graft of control fibroblasts, no c-RET-LI could be detected, indicating a depletion of c-ret-expressing cells by selective lesion of dopaminergic neurons in the adult substantia nigra (FIG. 14e). However, c-RET-LI could be rescued by the GDNF-expressing graft, where c-RET immunopositive fibers could be seen surrounding and penetrating the graft (FIG. 14f). Similar results were obtained in the locus coeruleus, where lesion with 6-OHDA depleted c-RET-immunoreactive cell bodies (FIG. 14g), which could be rescued by exogenous administration of GDNF (FIG. 14h). In both brain regions, the rescue of c-RET-LI positive cells and sprouting in the animals grafted with GDNF-expressing fibroblasts paralleled that of tyrosine hydroxylase immunoreactivity (data not shown), demonstrating that c-RET-expressing adult dopaminergic and noradrenergic neurons respond to GDNF.

Example 13

Identification of GDNF c-RET Receptors

PC12 cells and NB2/a cells were washed three times with serum free RPMI-1640 or DMEM, respectively, plated on noncoated (NB2/a cells) or collagen-coated (PC12 cells) dishes (5000–6000 cells per dish) in the presence or absence of 50 ng/ml of GDNF (Peprotech EC Ltd.) and the number of cells was microscopically counted-after 48 hours. PC12 and NB2/a cells were harvested (100,000 cells, five parallels), incubated with 10 ng/ml human $^{125}$I-GDNF (iodinated by Chloramine T method, 100 μCi/μg) in the presence or absence of 50-fold unlabeled GDNF for 120–150 min on ice, the unbound factor was removed by centrifugation through 30% sucrose cushion, and the cell-associated radioactivity counted on 1271 RIAGAMMA counter (LKB Wallac).

Figure 15A:
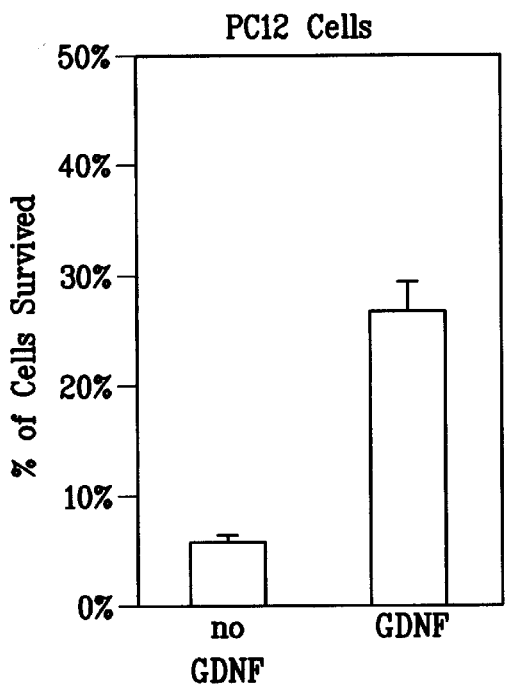
FIGS. 15 a–c. PC12 and NB2/a cells respond to GDNF and bind GDNF. (a) GDNF promotes survival of serum-deprived PC12 cells. (b) GDNF increases the number of NB2/a cells. (c) $^{125}$I-GDNF binds to PC12 and NB2/a cells in the absence (open column) or presence (filled column) of 50-fold unlabeled GDNF.

Recombinant human GDNF promoted survival of about 20% of serum deprived rat pheochromocytoma PC12 cells at concentration of 50 ng/ml (FIG. 15a). Serum-deprived PC12 cells are also maintained by nerve growth factor (NGF). Upon treatment with (NGF), PCI2 cells also stop dividing and differentiate into sympathetic neuron-like cells with long neurites. Thus, GDNF is a survival-promoting factor for PCI2 cells, although less potent than NGF, but it does not induce differentiation of PC12 cells at the concentrations studied, presumably because of the differences in signal transduction of NGFactivated trkA receptors and GDNF receptors.

Figure 15B:
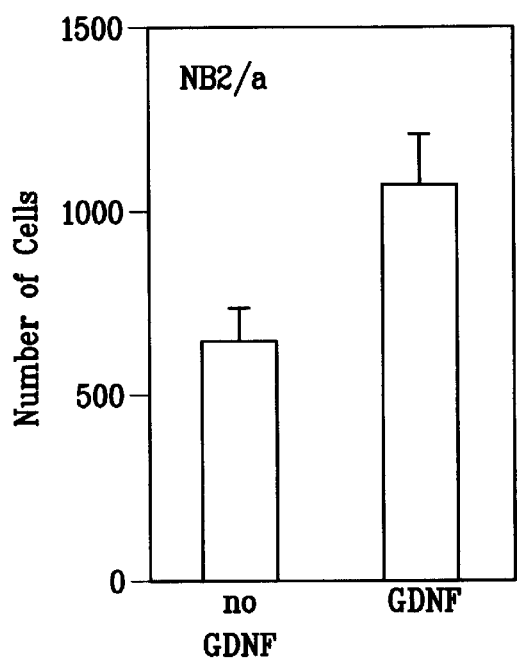

Human neuroblastoma NB2/a cells were plated in serum-free medium in the presence or absence of 50 ng/ml of GDNF and the number of cells was counted after 48 hr of culture. GDNF significantly increased the number of NB2/a cells (FIG. 15b). Monkey COS cells, human SY5Y cells and mouse NIH 3T3 cells showed neither mitogenic nor survival response to GDNF (data not shown). Thus, GDNF exerts biological effects on rat PC12 cells and human NB2/a cells, indicating that both cell lines express functional GDNF receptors.

Figure 15C:
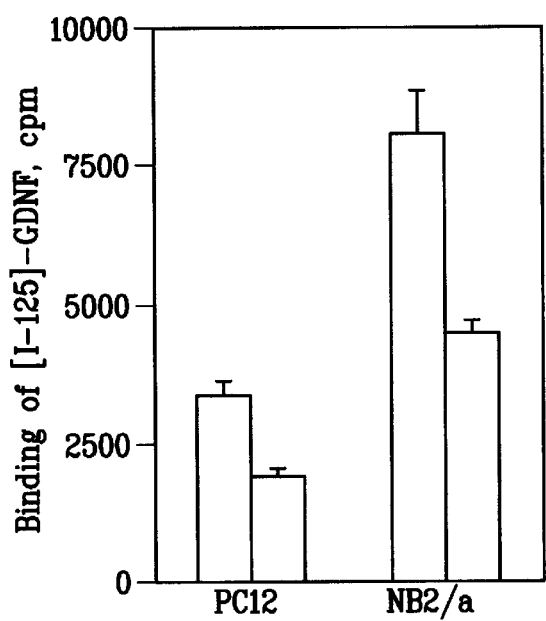

To determine, whether GDNF binds to the responsive cells, PC12 cells and NB2/a cells were incubated with $^{125}$I-labeled human GDNF at 40° C. as indicated in the legend to FIG. 15. As shown in FIG. 15c, both PC 12 and NB2/a cell lines bind GDNF 30 efficiently. More importantly, the binding of $^{125}$I-labeled GDNF could be competed with a 50-fold excess of unlabeled GDNF (FIG. 15b). Thus, the binding of GDNF to the receptors on PCI2 and NB2/a cells appears to be specific.

Example 14
Identification of GDNF c-RET Binding Components

PC12 cells, SY5Y neuroblastoma cells and NB2/a cells where chemically cross-linked to $^{125}$I-GDNF with EDC. 3–5×10$^6$ cells or mechanically dissociated cells from 2 E20 rat kidneys were incubated with 10 ng/ml of $^{125}$I-GDNF for I hour on ice and cross linked with 30 mM EDAC (Pierce) for 30 minutes on ice. Detergent lysates were immunoprecipitated, the precipitates collected by Protein A-Sepharose, separated on 7% SDS-PAGE, and visualized by Phosphorimager SI (Molecular Dynamics).

Figure 16:
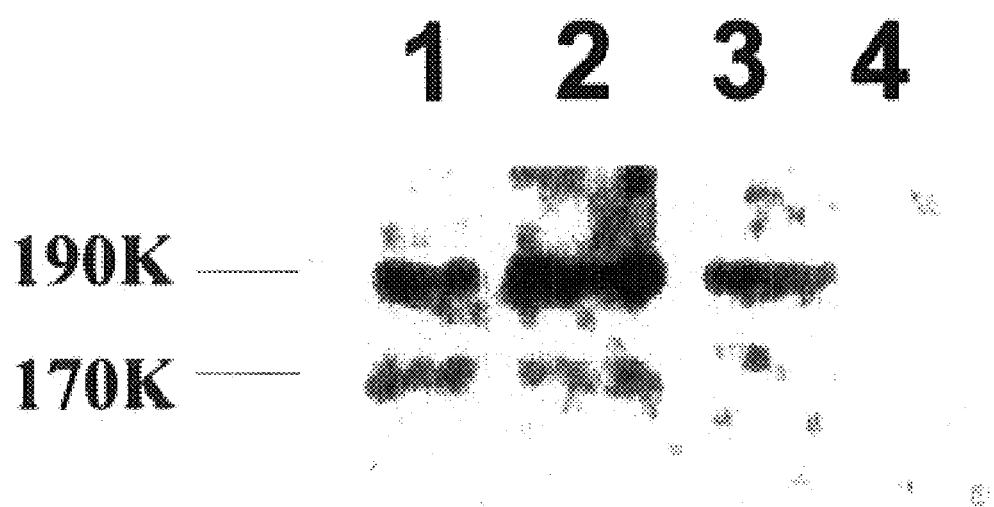
FIG. 16. Affinity crosslinking of $^{125}$I-GDNF to cell lines. $^{125}$I-GDNF was crosslinked to PC12 cells (lane 1), SY5Y cells (lane 2), E20 rat kidney cells (lane 3) and NB2/a cells (lane 4), and the resulting complexes were precipitated from detergent lysates by anti-GDNF antibodies (Santa Cruz).

The resulting complexes were imnmunoprecipitated with rabbit antibodies to GDNF, analyzed by SDS-PAGE and visualized by autoradiography. Embryonic kidney cells were also studied as the source of putative GDNF receptor (Suvanto, P. et. al., *Eur. J. Neurosci.*, 8, 101–107 (1996); Sainio, K. et. al., *Nature*, (1996) submitted). Cross-linked complexes of 170 and 190 kD were obtained from the extracts of PC12 cells, SY5Y cells and NB2/a cells and a 190 kD complex from embryonic kidney extracts. (FIG. 16).

The molecular weights of the cross linked proteins minus GDNF of approximately 25–30 kD, substantially, if not exactly, correspond to the molecular weights of c-RET protooncogene, an orphan receptor tyrosine kinase (Takahashi, M., Ritz, J. & Cooper, G. M. *Cell*, 42, 581–588, 1985; Takahashi, M. et.al., *Oncogene*, 3, 571–578 (1988)) (140 kD and 160 kD, representing differently glycosylated forms of c-RET., Tsuzuki, T., Takahashi, M., Asai, N., lwashita, T., Matsuyama, M. & Asai, J. *Oncogene*, 10, 191–198 (1995).

Example 15
Affinity Cross Linking of GDNF to c-RET

Figure 17A:
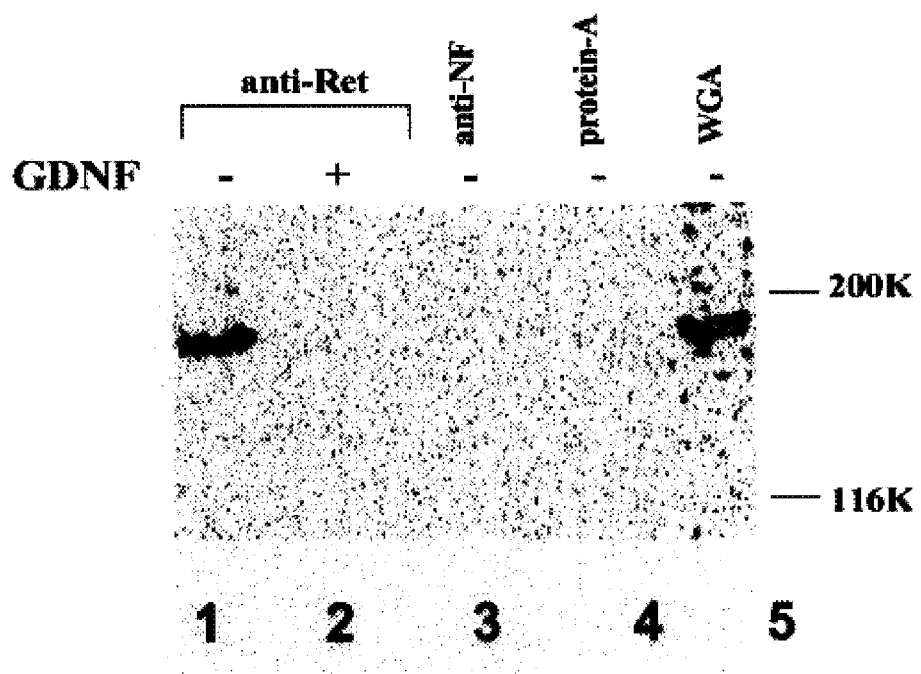
FIGS. 17 a–b. GDNF specifically binds to c-RET. (a) $^{125}$I-GDNF was crosslinked to NB2/a cells in the presence (+) or absence (−) of 1000-fold excess of unlabeled GDNF (PeproTech EC Ltd.), and the resulting complexes were precipitated from detergent lysates by cocktail of monoclonal and polyclonal (Santa Cruz) anti-c-RET antibodies recognizing the extracellular and intracellular domain of cRET, respectively. Lysates were also precipitated by monoclonal anti-neurofilament antibodies 13AA8 (lane 3), by Protein A-Sepharose (lane 4) and by WGA-Agarose (lane 5). (b) $^{125}$I-GDNF binds to COS cells transiently expressing c-RET, but not to mock-transfected (with pBK-CNV plasmid) COS cells. Open column represents binding in the presence, and filled column in the absence of 50-fold excess of unlabeled GDNF.

The cross linked complexes were immunoprecipitated from the NB2/a cells with the cocktail of antibodies recognizing extracellular and intracellular part of the c-RET receptor. As shown in FIG. 17a (lane 1), the complexes of 170 kD and 190 kD were precipitated by anti-c-RET antibodies, which thus correspond to cross linked GDNFc-RET complexes. Binding of $^{125}$I-GDNF to c-RET proteins was completely abolished by 500-fold excess of unlabeled GDNF (lane 2). No proteins were precipitated by monoclonal anti-neurofilament antibodies (lane 3) or by Protein A-Sepharose only (lane 4). No cross linked complexes were obtained from COS cells (not shown). Since c-ret proto-oncogene is a glycoprotein, $^{125}$I-labeled NB2/a cell extracts were also immunoprecipitated with wheat germ agglutinin. Again, proteins of 170 and 190 kD were obtained (lane 5).

To establish further that GDNF specifically binds c-RET, the mouse c-ret cDNA was cloned into the mammalian expression vector PBK-CMV and transiently expressed in monkey COS cells. Mouse c-ret cDNA (Pachnis, V., Mankoo, B, & Costantini, F. *Development*, 119, 1005–1017 (1993)) in pbluescript SK' (Stratagene) was cleaved with SacII and EcoRV and cloned into Sacll and SmaI site of pBK-CNV vector (Strategene). COS cells were transiently transfected with c-ret cDNA or with empty plasmid by electroporation (Bio Rad) with –30% efficiency by fluorescence of cotransfected Red Shift Green Fluorescent Protein in PEF-BOS vector. 48 hours later, 10×10$^6$ transfected COS cells or 3–5×10$^6$ parental COS cells or NB2/a cells were treated With $^{125}$I-GDNF, cross linked and analysed as specified in legends of FIG. 15 and FIG. 16.

Figure 17B:
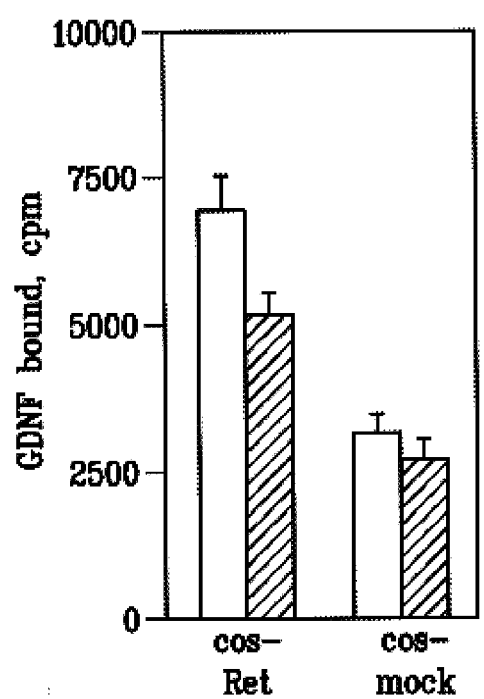

First, the expression of c-RET protein was examined by Western blotting. c-ret-transfected COS cells (FIG. 18a) and NB2/a cells (not shown) expressed detectable amounts of the c-RET protein, whereas no c-RET protein was detected in mock-transfected (with PBK-CMV plasmid) COS cells (FIG. 18a). PC12 cells also express c-RET protein, albeit at considerably lower level than NB2/a cells or c-ret-transfected COS cells (not shown). COS cells, transiently expressing mouse c-ret proto-oncogene were incubated with $^{125}$I-GDNF. As shown in FIG. 17b, those cells bound GDNF, and binding of $^{125}$I-GDNF can be competed with excess of unlabeled GDNF. In contrast, no significant binding-of GDNF was observed in mock-transfected COS cells.

Example 16
Phosphorylation of Tyrosine Residues

10×10$^6$ transfected COS cells (48 hr after transfection) were treated with 50 ng/ml of GDNF (Preprotech EC Ldt.) for 5 minutes in serum-free DMEM, or not treated, and then quickly washed with the same medium. NB2/a cells were similarly treated (results not shown). c-RET proteins were immunoprecipitated from detergent extracts by cocktail of monoclonal (Lo, L. & Anderson, D. J. *Neuron*, 15, 527–539 (1995) and polyclonal (Santa Cruz) anti-c-ret antibodies, separated by 7% SDS-PAGE, transferred to nitrocellulose, probed by anti-c-ret antibodies (Santa Cruz), stripped and reprobed by anti-phosphotyrosine antibodies (Sigma).

Figure 18:
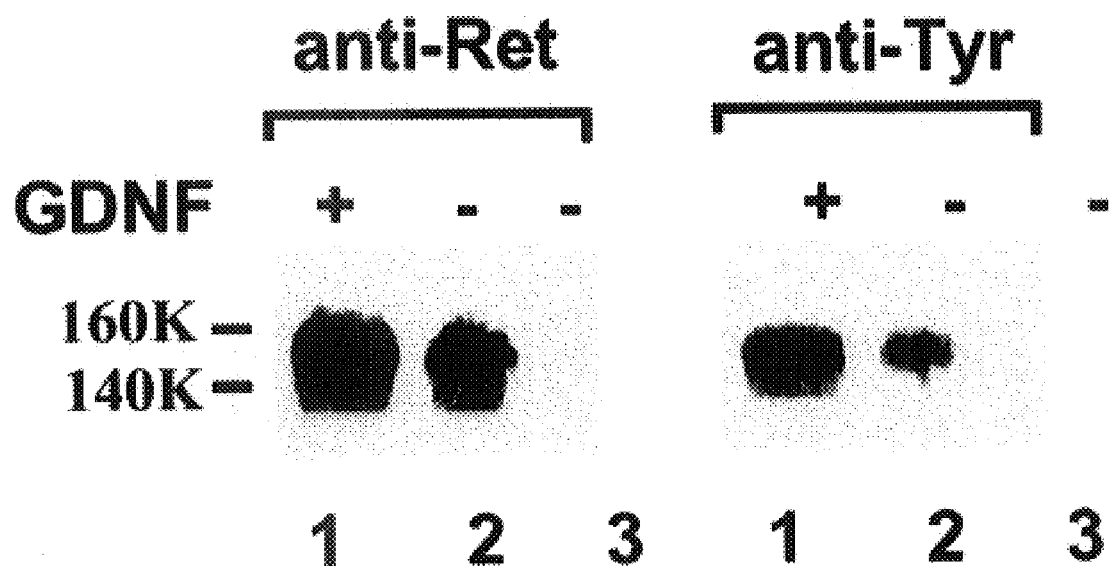
FIG. 18. GDNF increases tyrosine phosphorylation of c-RET in transfected COS cells. c-RET was immunoprecipitated from detergent lysates of GDNF-treated (+) (lane 1) or untreated (−) (lane 2) COS cells transfected (lane 3) with c-ret cDNA or mock-transfected with PBK-CMV plasmid. (a) immunoblot probed with anti-c-RET antibodies (Santa Cruz). (b) the same filter reprobed with anti-phosphotyrosine antibodies.

This treatment resulted in significant increase in tyrosine phosphorylation of 190 kD cRET proto-oncogene, the 170 kD form being less prominently phosphorylated (FIG. 18b). In both cell lines, relatively high c-RET phosphorylation was detected also in the absence of GDNF (FIG. 18), most probably via endogenous GDNF secreted by these cells and/or ligand-independent receptor dimerization.

Example 17
$^{125}$1-GDNF Binds to c-ret-positive Enteric Neurons $^{125}$I-GDNF was bound to developing rat tissue explants in situ. In situ binding of human $^{125}$I-GDNF (PeproTech. EC Ltd.), iodinated by Chloramine T Method, was carried out essentially as described (Partanen and Thesleff, 1987). Briefly, explants of E15 rat gut were incubated with 10 ng/ml of $^{125}$I-GDNF in Eagle's minimal essential medium on the Nuclepore filter (Costar) for 90 min at room temperature. 250-fold excess of unlabeled GDNF was applied as a competitor to control explants. After careful washing, the explants were fixed with 3.5% paraformaldehyde in PBS, sectioned and exposed to NTB-2 emulsion (Kodak).

The gastrointestinal tract was chosen as it strongly expresses GDNF mRNA (Suvanto et al., 1996); FIG. 19a and b) and c-RET-positive neurons are absent in the gastrointestinal tract in c-ret-deficient mice (Schuchart et al., 1994; Durbec et al., 1996). $^{125}$I-GDNF binds to a group of cells within the muscle layer of embryonic day (E)15 rat gut (FIGS. 19c and d). This binding was specific as it was totally competed with 250-fold excess of unlabeled GDNF (FIG. 19h). The cells that bind GDNF were the enteric neurons of the myenteric plexus, as revealed by peripherin immunoreactivity (FIG. 19f).

Moreover, these neurons also expressed c-ret mRNA, as demonstrated by in situ hybridization (FIG. 19e). Cloning of the GDNF cDNA and in situ hybridization with GDNF probe was performed exactly as described (Suvanto et al., 1996). A 646 bp long fragment of mouse c-ret cDNA (Pachnis et al., 1993) covering the 3'-region of the shorter form (Takahashi et al., 1988) of c-ret was cloned into NotI-XhoI site of pBSK+vector (Stratagene). cRNAs in antisense and sense orientation were labeled with digoxigenin-UTP (Boehringer-Mannheim), hybridized to cryosections through E15 rat gut and visualized with alkaline phosphatase-conjugated anti-digoxigenin antibodies according to manufacturers instructions. In both cases, only background labeling was obtained with hybridization of corresponding probes in sense orientation (FIG. 19g). Polyclonal anti-peripherin antibodies (Bio-Rad) were applied to cryosections of E15 rat gut at a dilution of 1:100 for 1 hr and visualized by FITC-conjugated secondary antibodies (Jackson). Thus, GDNF specifically binds to c-RET-expressing enteric neurons of developing rat.

Example 18
Affinity-cross Linking of GDNF to c-RET

PC12 cells and NB2/a cells were washed three times with serum-free RPMI-1640 or DMEM, respectively, plated on uncoated (NB2/a cells) or collagen-coated (PC12 cells) dishes (5000–6000 cells per dish in triplicate) in the presence or absence of 50 ng/ml of GDNF (PeproTech EC Ltd.), and the number of cells microscopically counted after 48 h.

For c-RET expression in transfected cells, the shorter form (Takahashi el al., 1988) of human wild-type c-ret cDNA was subcloned in pcDNA3 (Invitrogen). 3T3 fibroblasts were stably transfected with c-ret expression plasmid or with empty vector (mock-transfected cells) and positive cells lines selected with G418.

Transient transfection of trkC 3T3 fibroblasts (Ip et al. (1993) Neuron, 10,137–149) with human c-ret cDNA in pcDNA3 vector or with empty vector was performed by the lipofectin method (Gibco-BRI.). c-ret and mock-transfected cells (10.000–15.000 cells per well) in five parallels were treated with rat GDNF (Trupp et al. (1995) J. Cell. Biol. 130, 137–148) at indicated concentrations for five days. NT-3 was used as positive control at 30 ng/ml. Cell number was quantified by measurement of acid phosphatase activity using Abacus™ Cell Proliferation Kit (Clontech).

$3-5 \times 10^6$ PC12 cells, NB2/a cells, COS cells or c-ret-3T3 as well as mock-3T3 cells or mechanically dissociated cells from two F20 or from 17 E15 rat kidneys were incubated with 10 ng/ml of $^{125}$I-GDNF (human GDNF from Pepro-Tech EC Ltd. or rat GDNF from C. F. Ibanez) (Trupp et al., 1995), iodinated by Chloramine T method, for 1 hour on ice. 250-fold excess of unlabeled GDNF (PeproTech EC) or TGF-β1 (kindly provided by Dr. M. Laiho) was applied to control sample. $^{125}$I-GDNF was then crosslinked to the cells with 30 mM of ethyl-dimethylaminopropyl carbodiimide (EDAC) (Pierce) for 30 minutes on ice. Detergent lysates of the cells were immunoprecipitated with polyclonal anti-GDNF antibodies (Santa Cruz) or with the cocktail of monoclonal (kindly provided by Dr. D. Anderson, Lo and Anderson, 1995) and polyclonal (Santa Cruz) anti-c-RET antibodies to neurofilament proteins (a gift of Dr. I. Virtanen) were used as control antibodies. The precipitates were collected by Protein A-Sepharose (Pharmacia) or by WGA-agarose (a gift from Dr. O Renkonen), separated on 7% SDS-PACE, and visualized with a Phosphorimager SI (Molecular DynanLics).

First, $^{125}$I-GDNF was cross linked to PC12 cells, NB2/a cells and COS cells with ethyl-dimethyiaminopropyl carbodiimide (EDAC), and the complexes were precipitated with anti-GDNF antibodies. As shown on FIG. 20a, complexes with molecular weight of 190 kD and 170 kD were obtained from PC12 and NB2/A cells, but not from COS cells. The molecular weights of the cross linked proteins (minus GDNF monomer of ~25K) correspond to those of c-RET, (140 kD and 160 kD, representing partially and fully glycosylated isoforms of c-RET, respectively) (Takahashi et al., 1988).

Next, $^{125}$I-GDNF was cross linked to PC12 and NB2/a cells by EDAC and immunoprecipitated formed complexes with anti-c-RET antibodies. The bands with molecular weight of 190 kD were obtained from both cell lines (FIGS. 20a and b). Formation of the complexes was abolished by 500-fold excess of unlabeled GDNF. The reason why both fully and partially glycosylated forms of c-RET were precipitated by anti-GDNF antibodies, but only the larger isoform by anti-c-RET-antibodies, is unclear. The same complexes, although much weaker, were also obtained when dithiobis(succinimidylpropionate) was used as a crosslinker (data not shown).

The EDAC-crosslink approach was also used to reveal GDNF-c-RET complexes from E15 embryonic kidney cells, where c-ret mRNA is strongly expressed in the tips of growing ureter branches. With both anti-GDNF and anti-c-RET antibodies, a band of 190 kD was obtained (FIG. 20a and b) that was competed with excess of unlabeled GDNF. Thus, only the fully glycosylated form of c-RET is expressed in embryonic kidney cells.

Cross linked $^{125}$I-GDNF-c-RET complexes from the cells ectopically expressing c-ret were also demonstrated. 3T3 cells were transfected with c-ret cDNA or with empty plasmid, and established stable transfected cell lines (c-ret-3T3 cells or mock-3T3 cells). Cross linking of $^{125}$I-GDNF to these cells followed by anti-RET-precipitation revealed a 190 kD band that was abolished with 250-fold excess of unlabeled GDNF (FIG. 20b). As GDNF is a distant member of TGF-β family, we also used a 250-fold excess of TGF-β1 as a competitor. No competition was observed with TGF-β1 (FIG. 20b) Taken together, these data show that GDNF directly and specifically binds to c-RET.

Example 19
GDNF Specifically Increases Tyrosine Phosphorylation of c-RET c-ret-3T3 cells and mock-3T3 cells were treated with GDNF and the proteins from these cells were immunoprecipitated with anti-c-RET antibodies. The precipitated proteins were then analyzed by Western blotting with anti-phosphotyrosine antibodies.

$10 \times 10^6$ c-ret-3T3 cells were treated with different doses of GDNF (PeproTech LC Ltd. or from C. F. Ibanez) (Trupp et al., 1995) for 5 min, or with 50 ng/ml of GDNF for indicated times in serum-free Dulbecco's modified Eagle's medium containing 1 mM $Na_3 VO_4$ and then quickly washed with the same medium. c-RET proteins were immunoprecipitated from detergent extracts, containing 1 mM $Na_3 VO_4$ by cocktail of monoclonal (Lo, L. and Anderson, D. J. (1995) Neuron, 15 527–539) and polyclonal (Santa Cruz) anti-c-RET antibodies, separated by 7% SDS-PAGE and transfected to nitrocellulose which were probed by anti-phosphotyrosine antibodies to nitrocellulose with was probed by anti-phosphotyrosine antibodies PY20 (Transduction Laboratories), then stripped and reprobed by anti-c-RET antibodies (Santa Cruz).

Figure 21A:
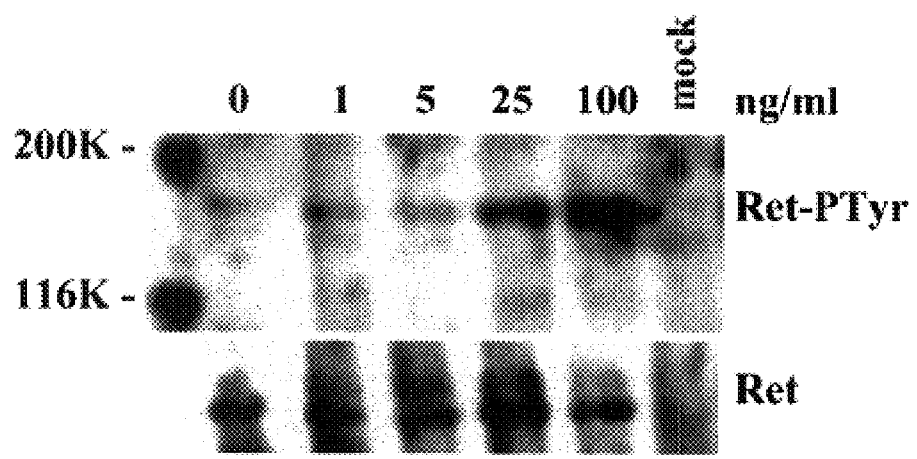
FIGS. 21 a–b. GDNF increases c-RET autophosphorylation in stably transfected 3T3 cell line. (a) GDNF dose-dependently increases tyrosine phosphorylation of 160 kD isoform of c-RET in c-ret-transfected (ret-3T3) but not in mock-transfected (mock) cells. (b) GDNF time-dependently increases tyrosine phosphorylation of 160 kD isoform of cRET in c-ret-transfected 3T3 cells. Upper panels (Ret.-PTyr) are the immunoblots stained with anti-phosphotyrosine antibodies, and lower panels (Ret.) show the reprobing of the corresponding filters with anti-c-RET antibodies.
Figure 21B:
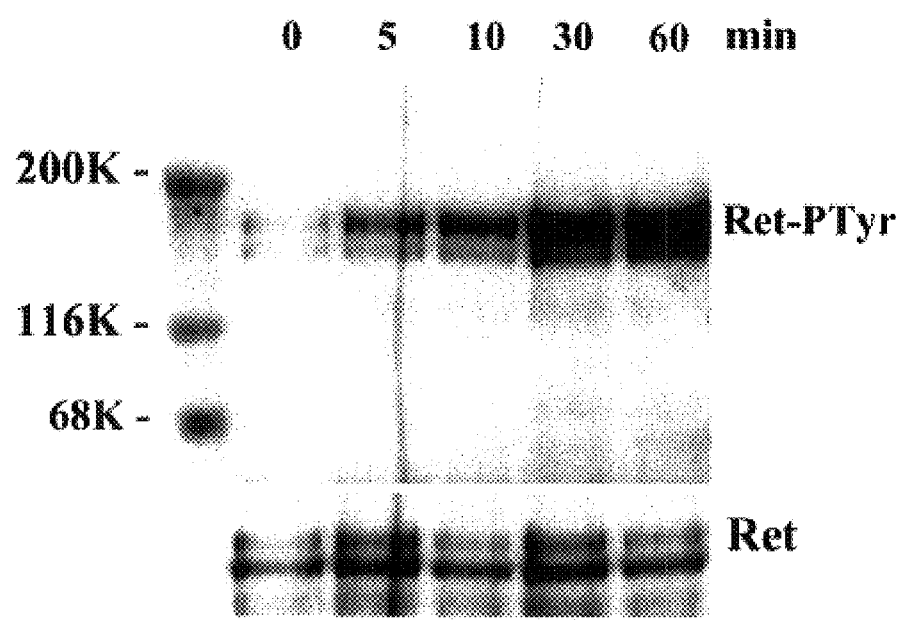

As shown on FIG. 21a, a short treatment of c-ret-3T3 cells with GDNF dose-dependently (beginning at 25 ng/ml) increased tyrosine phosphorylation of the 160 kD c-RET isoform, whereas the phosphorylation of the 140 kD isoform remained unchanged. An increase in c-RET phosphorylation was evident at 25 ng/ml of GDNF and above it. No c-RET proteins were detected in mock-3T3 cells. c-ret-3T3 cells were also treated with GDNF (50 ng/ml) for different times. An increase in c-RET tyrosine phosphorylation was evident after 5 minutes of treatment and continued at least for one hour (FIG. 21b). With prolonged exposition, the increase in phosphorylation of lower c-RET isoform also became evident. A basal level of c-RET phosphorylation was detected in the absence of GDNF, possibly via a ligand-independent dimerization of that receptor. To reveal the amounts of c-RET protein in these experiments, the filters were stripped from antibodies and reprobed with anti-c-RET antibodies. The level of c-RET protein was not changed by GDNF treatment in c-ret-3T3 cells (FIGS. 21a and b, lower panels). The finding that GDNF specifically activates c-RET indicates that c-RET is a signaling receptor for GDNF.

Example 20
c-RET Expression Confers GDNF-responsiveness to 3T3 Cells

Figure 22:
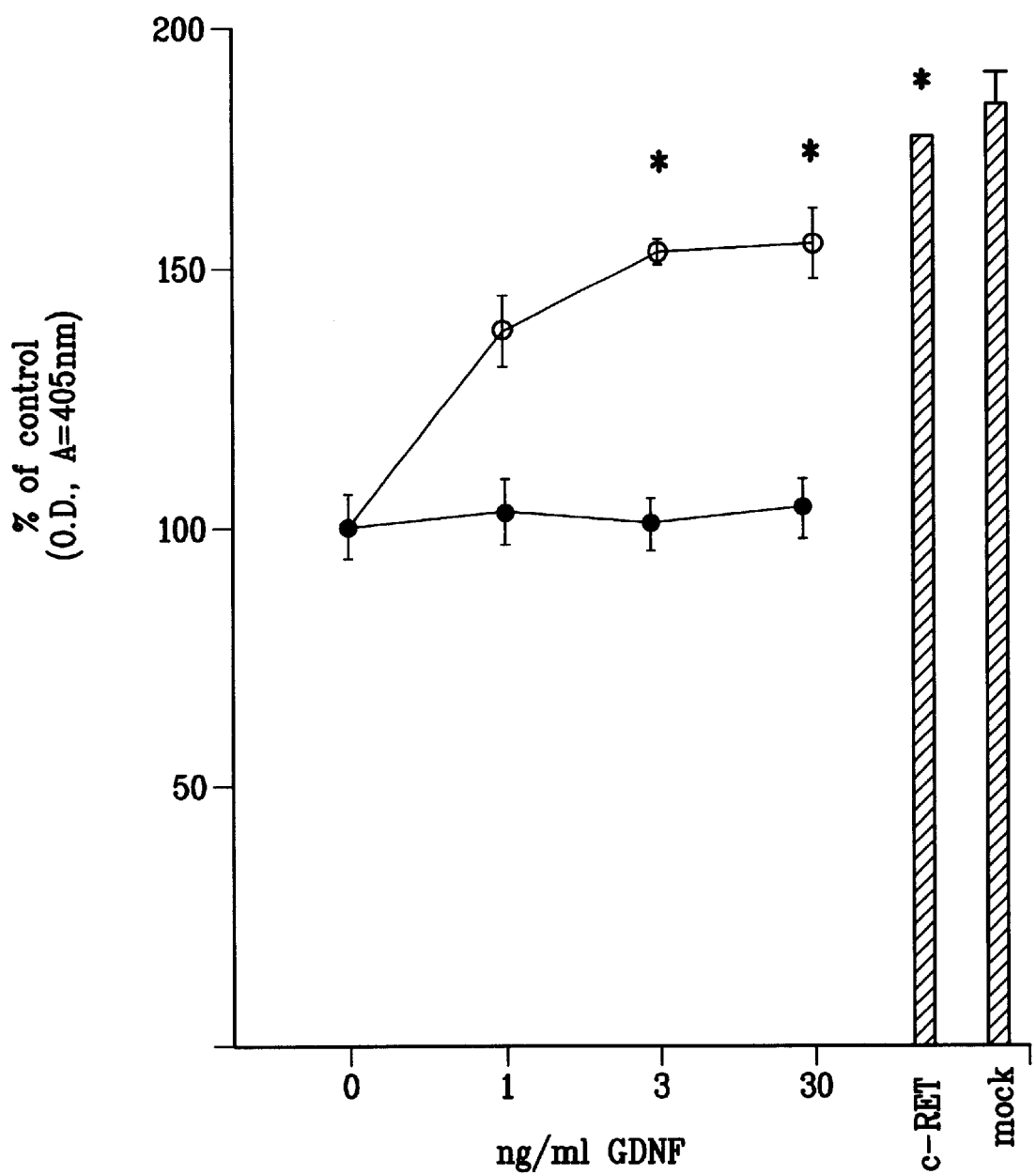
FIG. 22. GDNF increases the number of trkC-3T3 fibroblasts transiently expressing c-RET (open squares), but not mock-transfected cells (filled squares). c-ret and mock-transfected cells in five parallels were treated with rat GDNF at indicated concentrations, or with NT-3, for five days. Cell number, quantified with Abacus™ Cell Proliferation Kit (Clontech), is expressed as a percent of the control cells without growth factors. *, p<0.001 compared to mock transfected cells.

Mouse 3T3 fibroblast cell line expressing trkC (trkC-3T3) (Ip et al, 1993) were transiently transformed with c-ret expression plasmid. trkC-3T3 cells die within 2–3 days in serum-free medium in the absence of trkC ligand neurotrophin-3 (NT-3) (Ip et al., 1993) and do not express detectable amounts of c-ret. GDNF dose-dependently increased the number of c-ret-transfected but not of mock-transfected trkC-3T3 cells (FIG. 22), which was comparable to the response elicited by NT-3. Whether this is a proliferative or survival-promoting response could not be distinguished based upon the data. Thus, introduction of c-RET to GDNF-nonresponsive cells is sufficient to bring about the biological response to GDNF.

Example 21
Isolation of GDNF Receptor

Figure 23A:
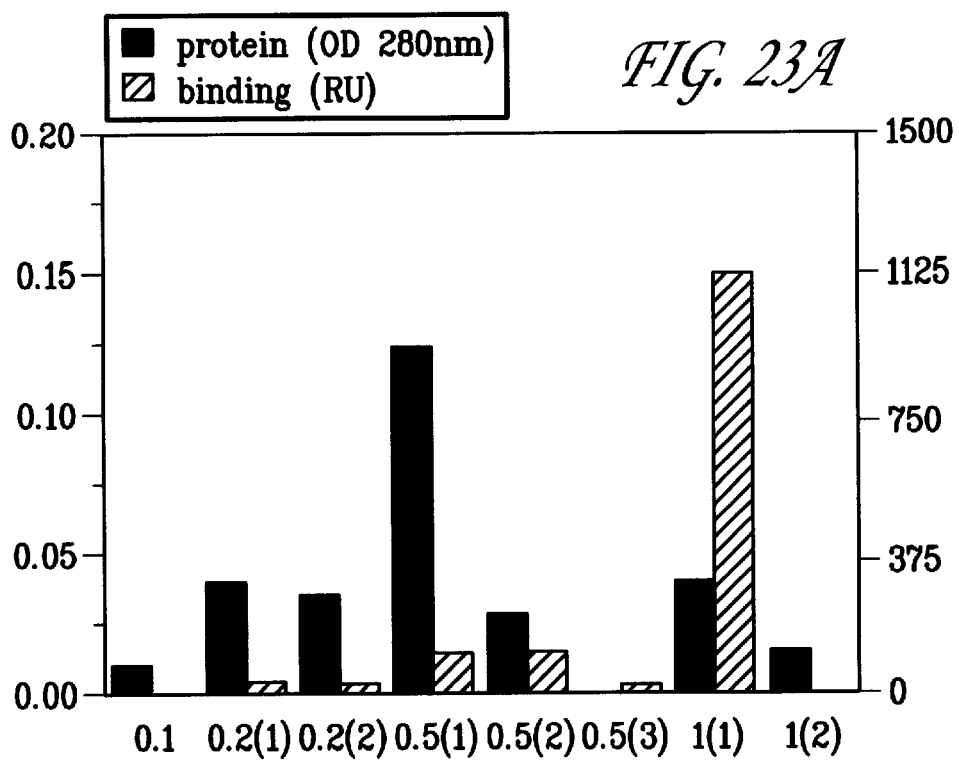
FIGS. 23 a–b. Purification of receptor from L6 myeloblast cells. (a) Plasmon resonance analysis of fractions obtained from anion exchange chromatography of L6 cell lysates. Total protein of fractions is also depicted. (b) Further purification of 1M fraction obtained from (a) by hydrophobic interaction chromatography.

L6 myoblast cells were lysed with 1% NP40 and cell lysates were fractionated by anionic exchange on a Q-Sepharose column. Fractions eluted at different ionic strength were dialyzed and assayed for binding to GDNF immoliblized on a chip in a Biacore device (Pharmacia). A distinct binding component was detected in a fraction of L6 cell lystaes (FIG. 23a). In the Figure, solid bars indicate total protein (as absorbance at 280 nm); hatched bars indicate GDNF finding (in resonance units). This fraction was not particularly rich in protein, indicating a substantial purification over the total protein mixture. The equivalent fraction of a COS cell lysate did not show binding under the same conditions (data not shown).

Figure 23B:
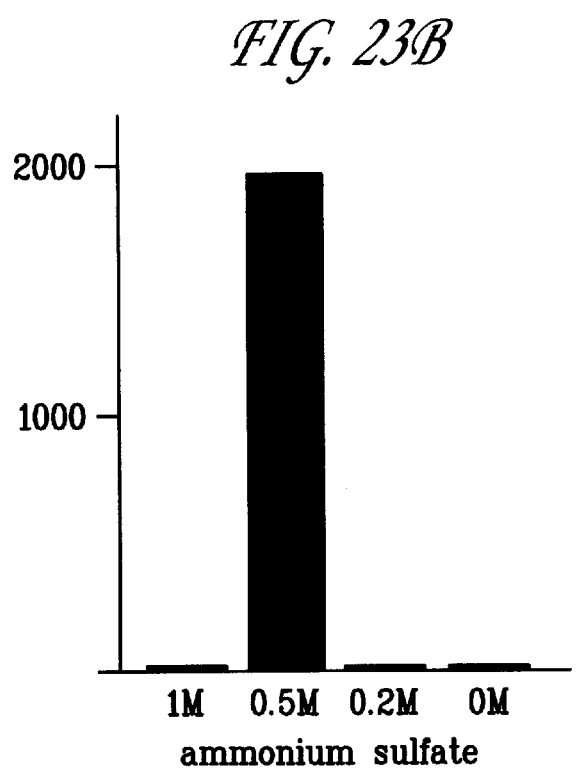

Further purification of the GDNF binding activity in the first 1 M salt fraction was obtained after hydrophobic interaction chromatography (FIG. 23b). The data represents the ratio between GDNF binding (in resonance units) and protein concentration (OD at 280 nm). Fractions were eluted with a step-wise gradient of ammonium sulfate.

Alternatively, purification may be effected by cross linking GDNF to cells in the presence of tracer amounts of radiolabeled ligand, and ligand/receptor complexes can by fractionated through ion exchange chromatography followed by hydrophobic interaction chromatography and SDS/PAGE. Bands corresponding to the molecular weights of GDNF-receptor complexes can by excised, dissociated, and then sequenced by mass spectrometry or Edman degradation, depending upon the yield of recovery.

Example 22
A Novel GDNF-binding Protein in Brain

By ligand blotting, we have identified another GDNF-binding protein from total brain extract. We bound $^{125}$I-GDNF to the filters carrying protein from the total extracts of brain and liver (a ligand blot assay). A major band with MW of about 50 kD was obtained from brain extract, but not from liver (FIG. 24). This binding is specific as $^{125}$I-GDNF did not bind to other proteins from total lysates, it is not found in liver lysates (nor in some other tissues), and it can be competed with excess of unlabeled GDNF.

Binding of $^{125}$I-GDNF to c-RET was not revealed in the ligand blots. The reason for this may be the very low share of c-RET in total brain extract. Alternatively, by analogy with other receptors for GDNF, c-RET might not bind GDNF directly, but might first bind to another nonsignalling receptor that thereafter presents the ligand to c-RET, a signaling receptor. A 50 kD GDNF-binding protein is a good candidate for the putative presenting receptor.

Example 23
Protocol for Isolating Novel Signaling Receptors for GDNF

In the absence of serum, 3T3 fibroblasts can be made dependent on a given exogenous growth factor provided appropriate receptors are expressed on the cell surface. An expression library can be made using RN33B cDNA, which can then be transfected into 3T3 fibroblasts by procedures well known in the art (Maniatis et al., supra). Stable transfectants can be selected in serum-free media supplemented with GDNF. Fibroblast clones that express signaling GDNF receptors will selectively grow in the presence of GDNF in serum-free media. The selection step may allow detection of even very reare clones due to their differential growth advantage. Further analysis of the recovered clones in media with or without GDNF would help to distinguish GDNF-dependent from GDNF-independent survival of clones.

Example 24
Cloning and Sequencing of GDNFR-β
Rat

A BLAST search of the publicly available genomic database at NCBI (National Center for Biotechnology Information) was performed using the amino acid sequence for GDNFR-α as reported in Jing et al. (1996) Cell 85:1113–1124 (hereby incorporated by reference). The search revealed several human ESTs with homology to the GDNFR-α. Primers were designed from these sequences and a partial cDNA clone was amplified from human fetal brain RNA. The upstream PCR primer was 5'ATGGATC-CGCAACCTGAATGACAACTGC3' [SEQ ID NO: 3]. The downstream PCR primer was 5'CCGAATTCAGT-TGGGCTTCTCCTTGTC3' [SEQ ID NO: 4]. This cDNA clone was used to screen a rat brain cDNA library from which a nearly complete cDNA was isolated. Additional PCRs were used to clone the most 5' of this cDNA. The complete cDNA sequence is depicted in FIG. 32 (SEQ ID NO:5). The amino acid sequence of the complete cDNA clone was determined and is depicted in FIG. 25. It is 464 amino acids long. A putative signal peptide and a GPI anchoring motif were identified in the N-terminal 15 and C-terminal 17 amino acid residues, respectively.

Human

Rat GDNFR-α sequence (6 GenBank™ accession number U59486) was used to screen the human EST database and 8 human sequences from 6 different clones (GenBank™ accession numbers H12981, H05619, R02135, R02249, T03342, W73681, W73633 and Z43761) with high similarity (identity >70% over 200 bp) were identified. Full sequence analysis of three EST clones revealed a 3'-terminal consensus sequence which we designated human EST GDNFR-β cDNA (nucleotides 469–1490 in FIG. 33).

To obtain complete cDNA, human EST GDNFR-β cDNA was used for screening an adult rat hippocampus cDNA library (λZap, Stratagene). Two identical clones out of one million contained a 2002 base pair long sequence with 91% identity to the probe. With a forward primer designed from rat GDNFR-β sequence, the 5' end of human GDNFR-β was amplified by PCR from human total brain cDNA. Human total RNA was extracted by standard methods and reverse transcribed in a random-primed reaction as described in Superscript II (Life Technologies) protocol. The human GDNFR-β gene was amplified from cDNA under the following PCR conditions: dNTP's in 200 μM concentration and primers (forward) 5'-ATGATCTTGGCAAACGCCTTCTG-3 [SEQ ID NO: 6] and (reverse) 5'-TTGCAGTTGTCATTCAGGTTGC-3' [SEQ ID NO: 7] in 1 μM concentration, approximately 5 ng of human brain cDNA, 1 u of Dynazyme (Finnzymes) Taq polymerase in 50 μl. The 30 cycles after initial 5 minutes at 94° C. consisted of 30 s at 94°, 30 s at 57° C. and 1 min at 72° C. with a final 5 minute extension at 72° C. The PCR fragments were cloned into pGEM-T vector (Promega) and four different clones were sequenced. With several primer pairs complete GDNFR-β cDNA sequence was amplified by PCR from the same human brain cDNA. This sequence was identical to the EST-derived sequence. The overlapping inserts of EST and PCR fragments were combined and cloned to get the contig of the full-length human cDNA. The human GDNFR-β cDNA sequence (GenBank™ accession number U93703) contains a 1395 base pair long open reading frame (FIG. 33).

At amino acid level, human and rat GDNFR-β orthologues were 96% identical. The predicted 47 kD (unglycosylated) mature protein, consists of 464 amino acids that are 48% identical and up to 63% similar to the published sequence of human and rat GDNFR-α proteins (Jing et al., supra) (FIG. 26). Alignment was performed using MAP (multiple alignment program). (Huang, X, Comp. Appl. BioSci., 10: 227–235, 1994. The putative signal sequence was predicted according to von Heijne, Nucl. Acids. Res., 14:4683–4699, 1986). The amino acid sequence of GDNFR-β has a putative signal sequence, three N-glycosylation sites, and a putative GPI-anchor site similar to GDNFR-α. Completely conserved cystein residues and strong overall resemblance to GDNFR-α predict high similarity in the spatial structures of the GDNF-receptors α and β (FIG. 26).

Amino acid identity as used herein means the same amino acid residue. Amino acid similarity as used herein means the same or chemically similar amino acid residue (e.g., Lys is identical to Lys, but is similar to Arg).

Example 25

GDNFR-α and GDNFR-β Expression

Figure 27:
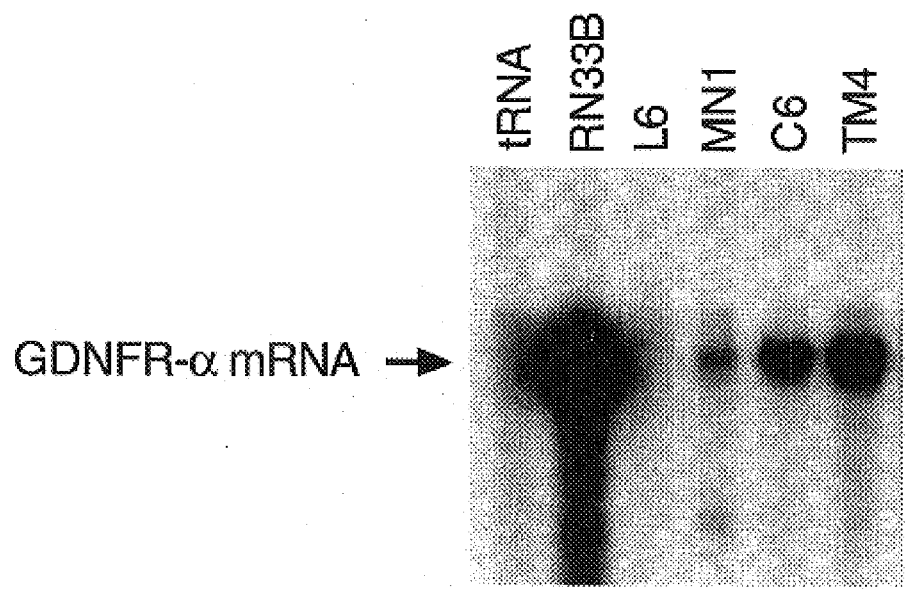
FIG. 27. Expression of GDNFR-α mRNA using RNAse protection analysis.
Figure 28:
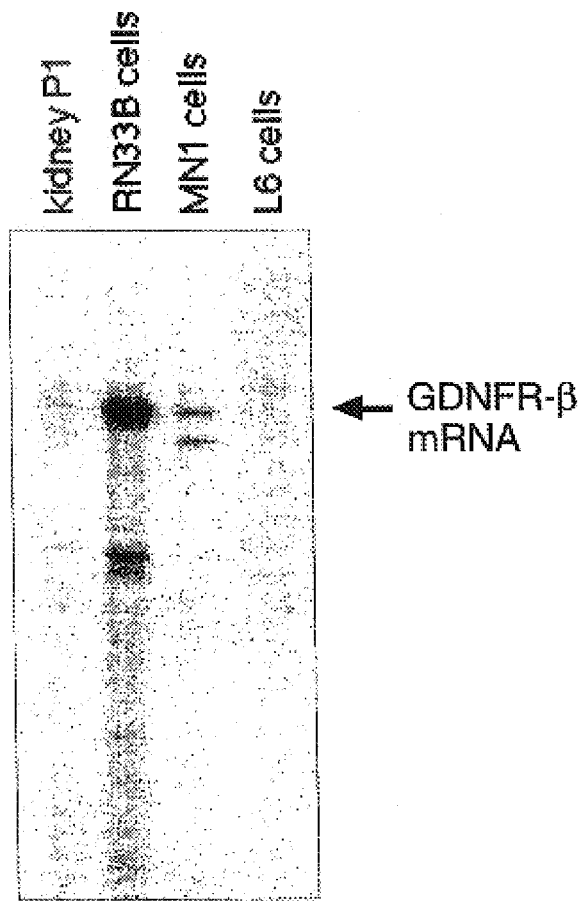
FIG. 28. Expression of GDNFR-β mRNA using RNAse protection analysis.

Expression of mRNA for GDNFR-α and GDNFR-β was investigated by RNAse protection analysis, as disclosed in Example 4 above, in cells known to express GDNF receptors as determined from chemical cross linking studies. GDNFR-α mRNA was found in RN33B and MN1 cells (FIG. 27). High levels of GDNFR-β mRNA were detected in RN33B cells. Lower levels were found in post-natal (P1) kidney and in MN1 cells. (See FIG. 28.) No GDNFR-α or GDNFR-β mRNA could be detected in L6 cells (FIGS. 27 and 28).

Figure 37M:
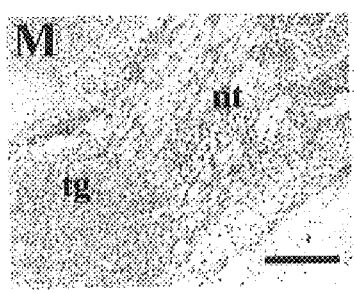
FIGS. 37A–O. Bright and dark field images of consecutive sections through adrenal gland (A, B,C,), kidney (D, E, F), small intestine (G, H, I), spinal cord (J, K, L), and trigeminal ganglia (M, N, O ) of E17 rat, hybridized with probes to rat GDNFR-β (B, E, H, K, N) or GDNFR-α (C, F, I, L, O ). Arrows indicate low GDNFR-β mRNA expression in the undifferentiated mesenchyme of kidney (E) and enteric neurons of gut (H). Abbreviations: ac=adrenal cortex, am=adrenal medulla, drg=dorsal root ganglion, en=enteric nervous layer, mn=ventral motoneuron column, nt=neural trunk of trigeminal secretory tubules, tg=trigeminal ganglion, u=tip of ureter bud, vr=ventral root of spinal cord. Bar=200 μm.
Figure 37N:
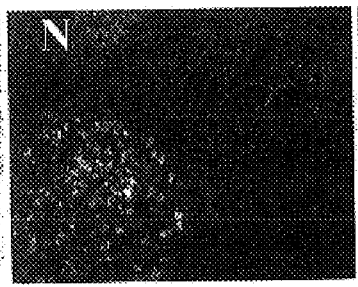
Figure 37O:
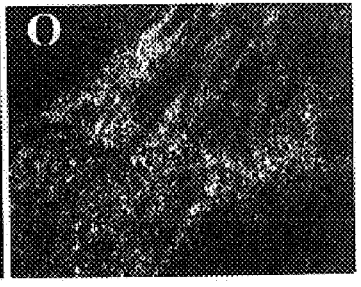

The mRNA expression patterns of GDNFR-α and GDNFR-β mRNAs were also determined and compared in E17 rat embryo by in situ hybridization. In situ hybridization on E17 rat sections was performed exactly as described previously (Suranto et al. Eur. J. Neurosc., 8:816–822, 1996; Wilkinson et al. in Post Implantation Mammalian Embryos a Practical Approach, IRL Press, Oxford, Copp., A. J. and Cockroft, D. L., eds. pp. 151–171, 1990, both incorporated herein by reference). The antisense cRNA probes for rat GDNFR-α and rat GDNFRβ covered nucleotides 294–1039 of GenBank™ sequence U59486 and nucleotides 1231–1394 of the rat GDNFR-β sequence, respectively. In several organs, GDNFR-α and GDNFR-β mRNAs showed distinct, non-overlapping distributions. Strong GDNFR-β mRNA expression was seen in the capsule and cortex of adrenal gland (FIG. 37B), whereas GDNFR-α mRNA was detected in adrenal medulla (FIG. 37C). In kidney, GDNFR-α transcripts were seen in the tips of ureter bud, condensed mesenchyme and early epithelial tubules (FIG. 37F), whereas GDNFR-β mRNA was present in undifferentiated nephrogenic mesenchyme and in the muscle wall of renal pelvis (FIG. 37E). Strong expression of GDNFR-α mRNA was present in the muscle and nervous layers along gastrointestinal tract (FIG. 37I). In stomach, GDNFR-β mRNA was moderately expressed in nervous layers (not shown), while in enteric plexus of small intestine only low amounts of transcripts were detected (FIG. 37H). In embryonic (E)17 rat nervous system, GDNFR-α mRNA was abundantly expressed in spinal cord, especially in ventral motoneurons (FIG. 37J). Also GDNFR-β mRNA was present in many areas of spinal cord including ventral motoneurons (FIGS. 5J, K), though the levels were moderate. In dorsal root and trigeminal ganglia, GDNFR-β mRNA expression was restricted to subpopulations of neuronal cells (FIGS. 37K,M,N), resembling Ret mRNA distribution (Pachnis et al., Development, 119:1005–1017, 1993). In contrast, varying amounts of GDNFR-α transcripts could be detected throughout the ganglia (FIGS. 37J,L,M,O) and also in the cells covering trigeminal and spinal nerves (FIGS. 37 M,O), suggesting expression in both neuronal and glial cells.

Example 26

Affinity Cross Linking of GDNF to GDNFR-α and GDNFR-β

Figure 29:
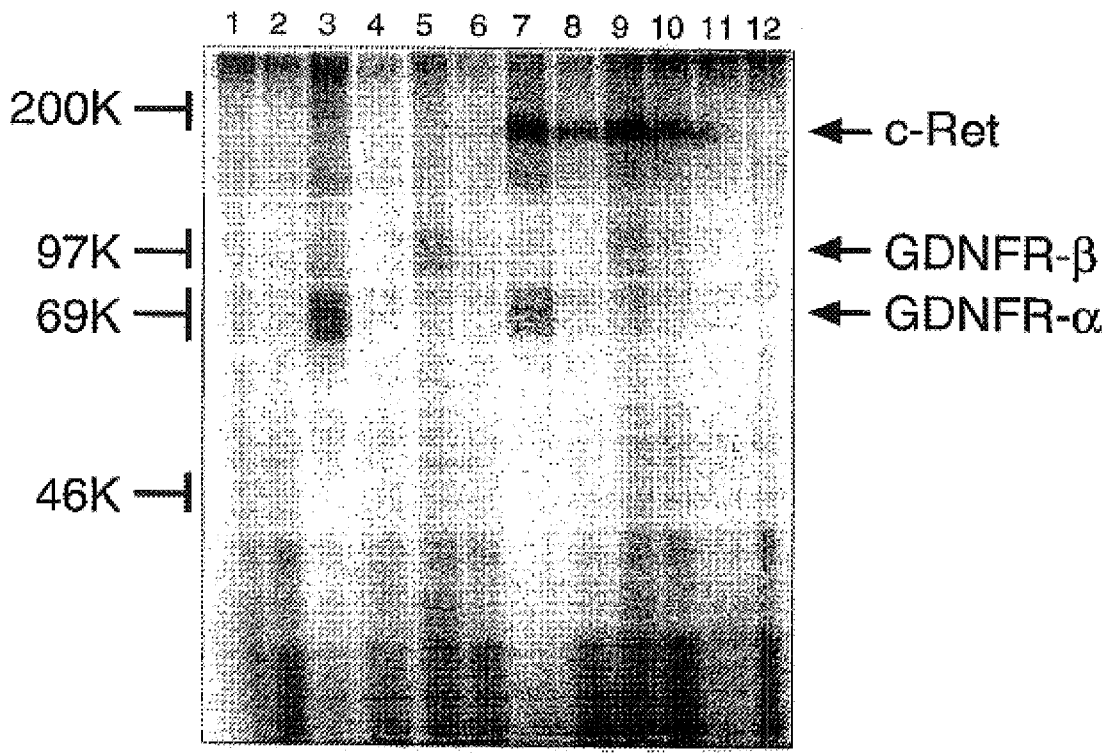
FIG. 29. Chemical cross linking of $^{125}$I-GDNF to GDNFR-α and GDNFR-β in transfected COS cells.

COS cells were transfected with GDNFR-α, GDNFR-β, c-RET, and a control plasmid and affinity cross linking studies were performed as disclosed in Example 15 above. The results are depicted in FIG. 29. COS cells transfected with a control plasmid did not bind GDNF (lanes 1 and 2). Transfection with a GDNFR-α cDNA followed by incubation with $^{125}$I-GDNF generated a GDNF binding complex with an approximate molecular weight of 70 kD (lane 3). The formation of this complex could be prevented by incubation with cold GDNF (lane 4).

Transfection with a GDNFR-β cDNA generated a GDNF binding complex with an approximate molecular weight of 100 kD (lane 5). The formation of this complex could also be prevented by incubation with cold GDNF (lane 6). Both GDNFR-α and GDNFR-β facilitated specific cross linking of $^{125}$I-GDNF to c-RET (lanes 7 to 10). COS cells transfected with a c-Ret cDNA alone did not bind GDNF (lanes 11 and 12). Molecular weight markers and the positions of the different GDNF receptor complexes are indicated.

Example 27

Comparison with Complexes from Cross Linking Studies with RN33B Cells

Figure 30:
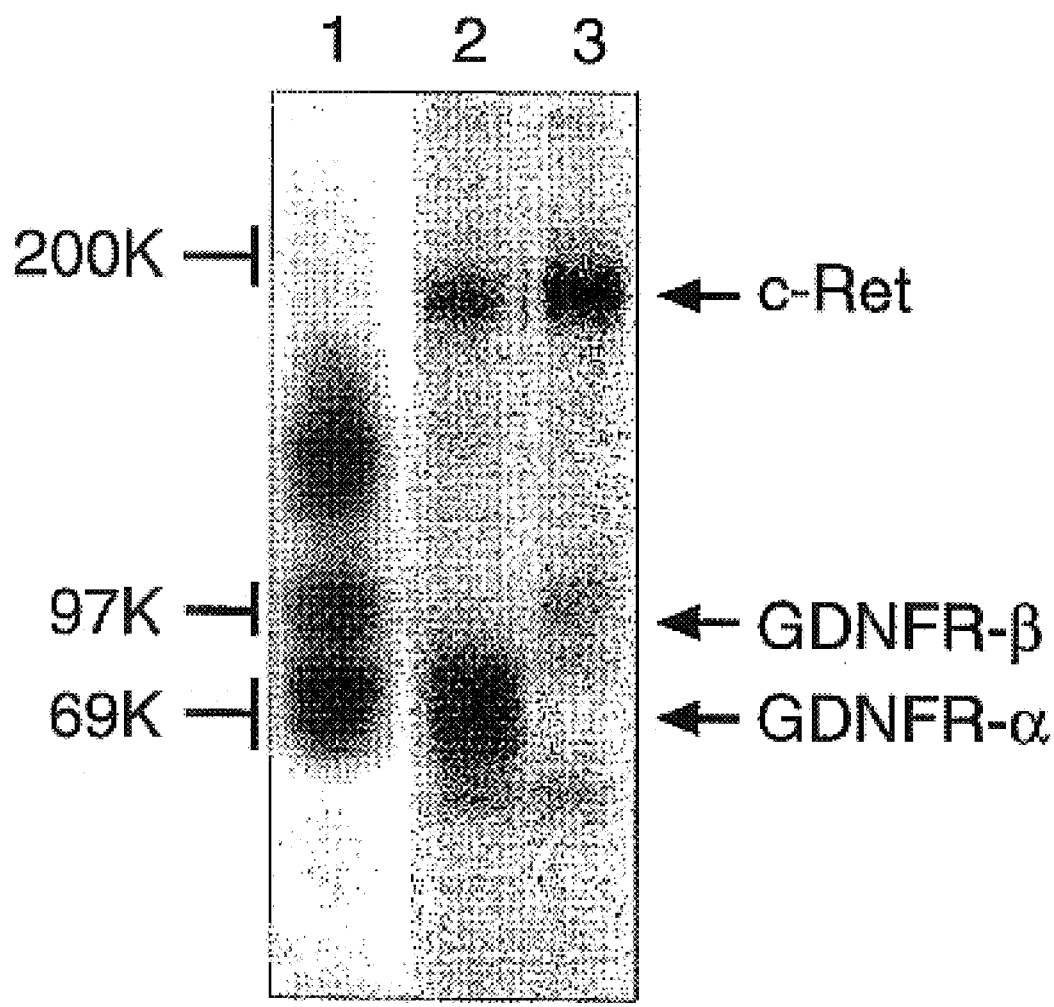
FIG. 30. Comparison of complexes obtained upon cross linking of $^{125}$I-GDNF to GDNFR-α and GDNFR-β in COS transfected cells with complexes obtained upon cross linking of $^{125}$I-GDNF to receptors on RN33B cells.

When compared side-by-side, the complex of GDNFR-α and GDNF formed in the transfected COS cells ran at the same molecular weight as the 70 kD complex detected in RN33B cells after GDNF cross linking with EDAC performed as disclosed in Example 2 (FIG. 30, compare lanes 1 and 2). The complex of GDNFR-β and GDNF formed in the transfected COS cells ran at the same molecular weight as the 100 kD complex detected in RN33B cells (compare lanes 1 and 3). The identity of the receptor component in the 155 kD binding complex is unknown, but it is formed by binding to the 135 k GDNF-binding protein identified above.

Example 28
Phosphorylation of cRET

Upon transfection into COS cells, cRET is highly phosphorylated on tyrosine residues independent of the presence or absence of GDNF (FIG. 31, upper panel). COS cells were transfected with 4 μg of c-Ret plasmid and 16 μg control plasmid. Transfected COS cells were exposed to different concentrations of GDNF using the procedure disclosed in Example 16, and cytoplasmic cell lysates were immunoprecipitated with anti-c-RET antibodies. Precipitated c-RET receptors were analyzed for tyrosine phosphorylation by Western blotting using anti-P-tyrosine monoclonal antibodies.

Co-transfection with plasmids encoding GDNFR-α or GDNFR-β (in place of the control plasmid), although allowing for ligand stimulation of receptor tyrosine phosphorylation in a dose-dependent manner, resulted in a dramatic attenuation of the steady-state levels of tyrosine phosphorylation of c-RET, i.e., in the absence of GDNF (FIG. 31, upper panel). Reprobing of the same blot with anti-c-RET antibodies revealed that all lanes contained equal amounts of c-RET (data not shown).

Figure 36:
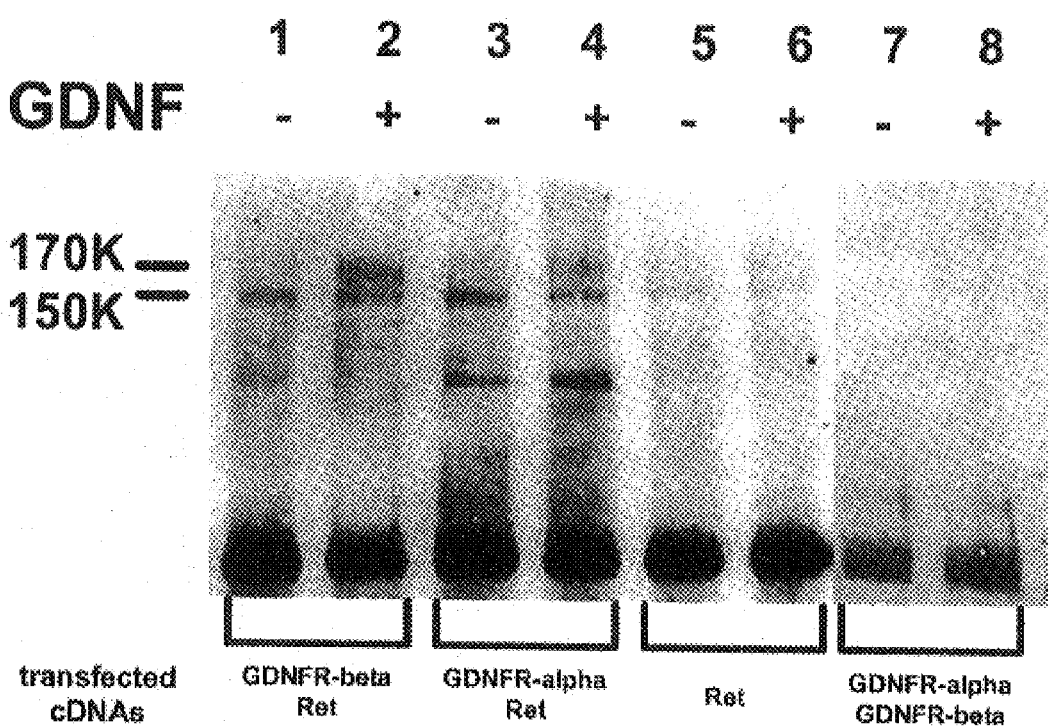
FIG. 36. GDNFR-β mediates GDNF-induced c-Ret autophosphorylation in transiently transfected COS-7 cells.

When COS-7 cells were transiently transfected with cDNAs encoding GDNF receptors in different combinations and treated with GDNF (100 ng/ml), it induced phosphorylation of the 170 kD form of Ret only in the presence of either GDNFR-α or GDNFR-β (FIG. 36, lanes 1–4), but not without these receptors (FIG. 36, lanes 5–6). The 170 kD from of Ret represents the fully glycosylated mature receptor on the plasma membrane (Takahashi et al. *Oncogene*, 3:571–578, 1988). In control cells cotransfected with GDNFR-α and GDNFR-β but without Ret, no tyrosine phosphorylated proteins were precipitated by anti-Ret antibodies (FIG. 36, lanes 7–8). Identical results were gained when a GDNFR-α construct lacking GPI-anchor was used (data not shown). Tyrosine phoshorylation of immature, partially glycosylated 150 kD form of Ret was not increased by GDNF treatment. The nature of the 85 kD bands in GDNFR-α transfected cells is not known. The major 50 kD band in all lanes is the heavy chain of IgG.

Human full-length GDNFR-β cDNA was cloned into pCDNA3 (Invitrogen) and pBk-CMV (Stratagene) mammalian expression vectors. Rat GDNF-β cDNA was cloned into the same expression vectors. In one rat construct, the 3' end of human GDNFRβ cDNA was added using a unique BclI restriction site and in another construct, an artificial stop codon was inserted instead of GPI-tail, producing an apparent soluble form of rat GDNFR-β.

COS-7 cells (5×10$^6$ cells per experimental point) were cotransfected by electroporation (Bio-Rad) with cDNAs (5 μg each) of Ret and GDNFR-α, Ret and GDNFR-β, GDNFR-α, and GDNFR-β, or with cDNA of Ret alone and cultured for 48 hours. Cellular phosphatases were inhibited by 1 mM Na$_3$, Vo$^4$ for one hour, the cells were treated with 100 ng/ml of GDNF (Promega or PeproTech Ltd) for 30 minutes and lysed in Tris-balanced saline. pH 7.5, containing 2 mM EDTA, 10% glycerol, 1% Nonidet P-40, 1% Triton x-100 and protease inhibitors. Proteins immunoprecipitated by anit-RET antibodies (Santa Cruz) were analysed by Western blotting with anti-phosphotyrosine antibodies PY20 (Transduction Laboratories). In experiments with the secreted form of GDNF-β lacking an GPI anchor, the cells were not washed before GDNF treatment.

Neuro-2A cells express c-RET endogenously, but show low levels of constitutive receptor tyrosine phosphorylation (FIG. 31, lower panel). However, transfection of the Neuro-2A cells using procedures disclosed above resulted in stimulation of tyrosine phosphorylation of the c-RET receptor in the presence of GDNF in a dose-dependent manner (FIG. 31, lower panel).

Example 29
Tissue Distribution of GDNFR-β

Figure 34:
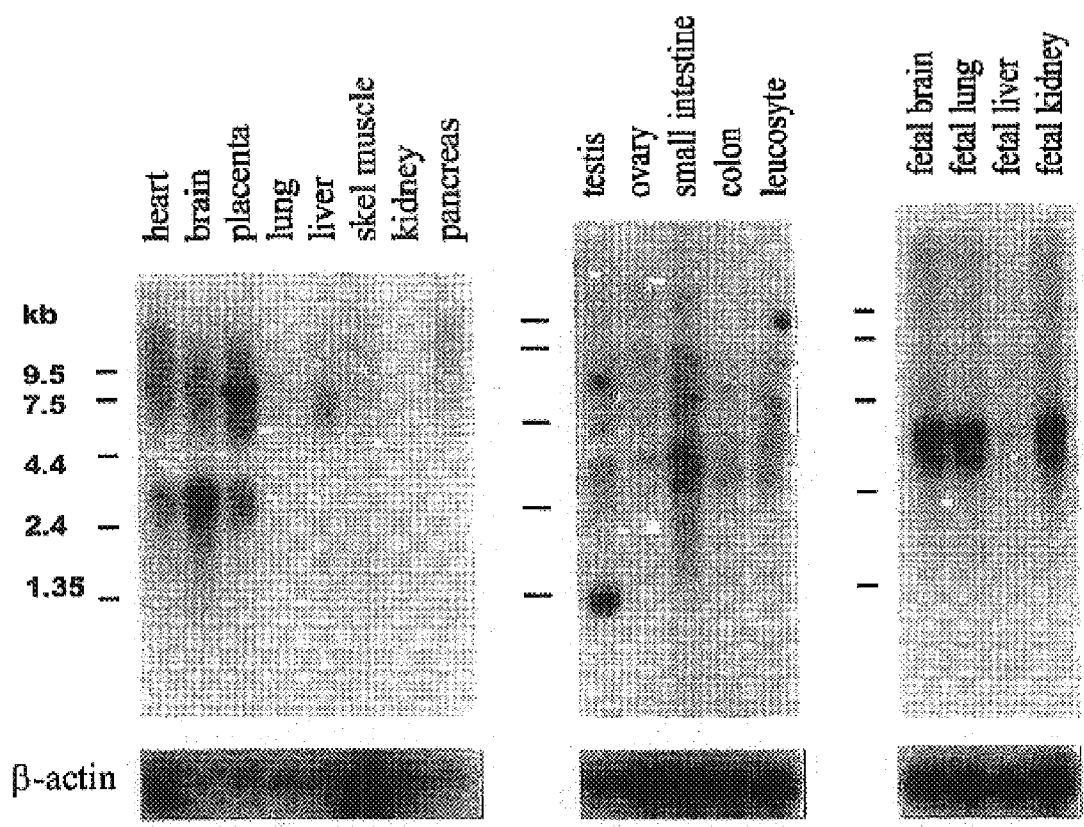
FIG. 34. Northern blot showing the expression of GDNFR-β mRNA in multiple human tissues. The molecular weight marker sizes are the same in all the filters. The lower panels present the same filters rehybridized with human β-actin probe.

The tissue distribution of human GDNFR-β was studied by Northern hybridisation of mRNA extracted from different adult and fetal tissues. The expression of GDNFR-β mRNA was abundant in adult brain, intestine and placenta, as well as in fetal brain, lung and kidney. Two major transcripts of 2.9 and 3.5 kb were visible in all tissues, and additional transcripts of 7.5 kb in placenta and 1.4 kb in testis (FIG. 34) were found.

For Northern Hybridization, 100 ng of the human EST GDNFR-β insert was labeled with $^{32}$P-dCTP (Amersham) by Prime-a-Gene-Kit (Promega). The specific activity of the final probe was 2×10$^7$ cpm/μg and the hybridization of Human and Human Fetal Multiple Tissue Northern Blot filters (Clontech) was performed in ExpressHyb solution at 65° for 2 hours. The filters were washed two times for 30 minutes at 50° C. in 2× saline sodium citrate (SSC)+0.1% SDS and 0.1% SSC+0.1% SDS and then analysed by phosphoimager (Fuji BAS 1500). As a control, the same filters were hybridized with human β-actin probe (Clontech).

Example 30
GDNFR-β Locus

Figure 35:
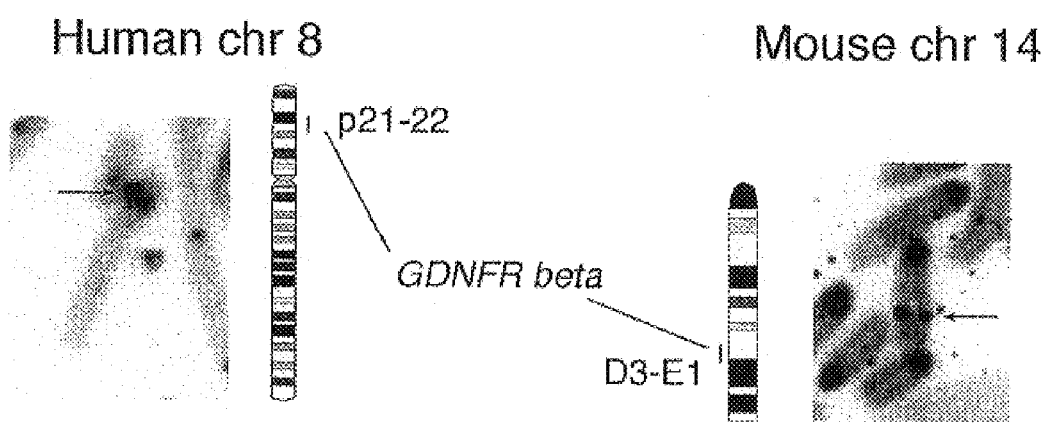
FIGS. 35A–B. Grayscale image of fluorescent in situ hybridization of the human (a) and mouse (b) GDNFR-β genes on metaphase chromosomes.

The chromosomal locus of GDNFR-β was assigned to human chromosome 8p21–22 by fluorescent in situ hybridization (FISH) with the 1.49 kb human GDNFR-β cDNA probe. In addition, the locus for mouse GDNFR-β gene was assigned to the mouse chromosome 14D3-E1 that corresponds to the human locus 8p21–22 (FIG. 35).

Human peripheral blood lymphocytes were cultured and the cell culture from a mouse fetal tissue was established according to standard protocols (Fresney, I. R., Culture of Animal Cells, Manual of Basic Techniques, Allan R. Lisa, Inc. New York, 1983) and used as a source of metaphases chromosomes. Both human lymphocytes and mouse monolayer cells were treated with 5-bromeoxyuridine at early replicating phase to induce a banding pattern (Takanashi, et al. *Hum. Gene*, 86:14–16, 1990; Lemieux et al., *Cell Gene*, 59:311–312, 1992). The slides were stained with Hoechst 33258 (1 μg/ml) and exposed to UV-light. (302 nm) for 30 min. The probes were labeled by a nick translation kit (BRL) with biotin-11-dUTP (Sigma) and the FISH procedure was carried out in 50% formamide, 10% dextran sulphate in 2×SSC as described earlier (Lichter et al., *Proc. Natl. Acad. Sci. USA*, 85:9664–9665, 1988; Pinkel et al, *Proc. Natl. Acad. Sci., USA*, 83:2934–2938, 1986, both incorporated herein by reference). Repetitive sequences were suppressed with 10-fold excess of Cot-1-DNA (BRL) and after overnight incubation unspecific hybridization signals were eliminated by washing the slides with 50% formamide/2×SSC, 2×× SSC and 0.5×SSC at 45° C. Specific hybridization signals were visualized using FITC-conjugated avidin (Vecotr Laboratories) and slides were counterstained with 4'-6'-diamino-2-phenylindole (25 ng/ml). The image analysis for acquisition, display and quantification of hybridization signals was performed with a PXL camera (Photometrics) attached to a PowerMac 7100/AV workstation. IPLab software controls the camera operation, image acquisition and Ludl wheel (Heiskanen, et al. *Genet. Anal. Biol. Eng.*, 12:179–184, 1996). The probe for human GDNFR-β gene was 1490 bp long cDNA and the hybridization showed specific double spot signal in 30 out of 100 metaphase chromosomes that were identified based on their G-banding pattern. The hybridization signal of the 10 kb genomic mouse probe showed specific localization in 27 out of 30 mouse metaphase chromosomes (Cowell, et al., *Chromosome*, 89:294–320, 1984). All references cited herein are hereby incorporated by reference in their entireties.

What is claimed is:

1. A method for identifying compounds which are GDNF homologs comprising
   a) incubating said compounds with cells which express c-RET receptors which bind GDNF; and
   b) determining whether said compound induces tyrosine phosphorylation of said c-RET receptors, whereby tyrosine phosphorylation of said c-RET receptors identifies said compound as a GDNF homolog.

2. The method of claim 1 wherein said cells are selected from the group consisting of PC12, MN-1, and NB2/a.

* * * * *